(12) United States Patent
Mogler et al.

(10) Patent No.: US 12,290,556 B2
(45) Date of Patent: May 6, 2025

(54) SWINE INFLUENZA A VIRUS VACCINE

(71) Applicant: Intervet Inc., Rahway, NJ (US)

(72) Inventors: Mark A. Mogler, Ames, IA (US);
Pravina Kitikoon, Overland Park, KS (US); Supraja Puttamreddy, Ames, IA (US); Erin Strait, Spring Hill, KS (US); Ruud Philip Antoon Maria Segers, Boxmeer (NL); Basav Nagaraj, Wageningen (NL)

(73) Assignee: Intervet Inc., Rahway (JE)

( * ) Notice: Subject to any disclaimer, the term of this patent is extended or adjusted under 35 U.S.C. 154(b) by 41 days.

(21) Appl. No.: 16/954,583

(22) PCT Filed: Dec. 17, 2018

(86) PCT No.: PCT/EP2018/085198
§ 371 (c)(1),
(2) Date: Jun. 17, 2020

(87) PCT Pub. No.: WO2019/121513
PCT Pub. Date: Jun. 27, 2019

(65) Prior Publication Data
US 2020/0330585 A1    Oct. 22, 2020

Related U.S. Application Data

(60) Provisional application No. 62/607,101, filed on Dec. 18, 2017.

(51) Int. Cl.
| *A61K 39/145* | (2006.01) |
| *A61K 49/00* | (2006.01) |
| *A61P 31/16* | (2006.01) |
| *C12N 9/24* | (2006.01) |
| *A61K 39/00* | (2006.01) |

(52) U.S. Cl.
CPC ............ *A61K 39/145* (2013.01); *A61K 49/00* (2013.01); *A61P 31/16* (2018.01); *C12N 9/2402* (2013.01); *A61K 2039/5256* (2013.01); *A61K 2039/53* (2013.01); *A61K 2039/552* (2013.01); *A61K 2039/55566* (2013.01); *A61K 2039/70* (2013.01)

(58) Field of Classification Search
None
See application file for complete search history.

(56) References Cited

U.S. PATENT DOCUMENTS

| 8,460,913 | B2 | 6/2013 | Kamrud et al. |
| 8,597,662 | B2 | 12/2013 | Jacobs et al. |
| 8,678,184 | B2 | 3/2014 | Kraus et al. |
| 8,808,686 | B2 | 8/2014 | Del Giudice et al. |
| 9,084,768 | B2 | 7/2015 | Jacobs et al. |
| 9,441,247 | B2 | 9/2016 | Rayner et al. |
| 9,730,997 | B2 | 8/2017 | Perri et al. |
| 9,764,024 | B2 | 9/2017 | Fomsgaard et al. |
| 10,619,169 | B2 | 4/2020 | Mundt et al. |
| 10,905,756 | B2 | 2/2021 | Eichmeyer et al. |
| 2009/0104226 | A1 | 4/2009 | Perri et al. |

FOREIGN PATENT DOCUMENTS

| JP | 2008500399 | A | | 1/2008 |
| WO | 2005007689 | A1 | | 1/2005 |
| WO | WO06078294 | | * | 7/2006 |
| WO | 2006082398 | A2 | | 8/2006 |
| WO | 2008033966 | A2 | | 3/2008 |
| WO | 2009014919 | A2 | | 1/2009 |
| WO | 2014005958 | A1 | | 1/2014 |
| WO | 2016137929 | A1 | | 9/2016 |
| WO | 2017123976 | A1 | | 7/2017 |
| WO | 2018054822 | A1 | | 3/2018 |
| WO | 2019179966 | A1 | | 9/2019 |
| WO | 2019191257 | A1 | | 10/2019 |
| WO | 2020035609 | A2 | | 2/2020 |

OTHER PUBLICATIONS

Walker et al., H1N1 Antibody Persistence 1 Year After Immunization With an Adjuvanted or Whole-Virion Pandemic Vaccine and Immunogenicity and Reactogenicity of Subsequent Seasonal Influenza vaccine: A multicenter follow-on study, 2012, CID, vol. 54, No. 5, pp. 661-669.*
Friedewald, Adjuvants in Immunization with Influenza virus vaccines, J Exp Med. 1944, vol. 80, No. 6, pp. 477-491.*
Anderson, Tavis K. et al., A Phylogeny-Based Global Nomenclature System and Automated Annotation Tool for H1 Hemagglutinin Genes from Swine Influenza A Viruses, mSphere, 2016, 1-14, 1(6) e00275-16.
Anderson, Tavis K. et al., Population dynamics of cocirculating swine influenza A viruses in the United States from 2009 to 2012, Influenza and Other Respiratory Viruses, 2013, 42-51, 7 (Suppl. 4).
Bodewes, Rogier et al., Animal models for the preclinical evaluation of candidate influenza vaccines, Expert Rev. Vaccines, 2010, 59-72, 9(1).
Bosch, et al., Recombinant Soluble, Multimeric HA and NA Exhibit Distinctive Types of Protection against Pandemic Swind-Origin 2009 A(H1N1) Influenza Virus Infection in Ferrets, Journal of Virology, Oct. 2010, pp. 10366-10374, vol. 84, No. 19.
Bredenbeek, Peter J. et al., Sindbis Virus Expression Vectors: Packaging of RNA Replicons by Using Defective Helper RNAs, Journal of Virology, 1993, 6439-6446, 67(11).

(Continued)

*Primary Examiner* — Benjamin P Blumel
(74) *Attorney, Agent, or Firm* — Susanna C. Benn

(57) ABSTRACT

The present invention provides vectors and/or nucleic acid constructs that encode one or more influenza A virus neuraminidase (NA) antigens. The present invention also provides vaccine against influenza A virus comprising such vectors and/or nucleic acid constructs. The present invention further provides methods of making and using the vaccines alone, or in combination with other protective agents.

20 Claims, 9 Drawing Sheets
Specification includes a Sequence Listing.

(56) References Cited

OTHER PUBLICATIONS

Brett, Ian C. et al., Immunization against influenza A virus: Comparison of conventional inactivated, live-attenuated and recombinant baculovirus produced purified hemagglutinin and neuraminidase vaccines in a murine model system, Virology, 2005, 273-280, 339(2).
Gao, Shibo et al., The genomic evolution of H1 influenza A viruses from swine detected in the United States between 2009 and 2016, Journal of General Virology, 2017, 2001-2010, 98(8).
Hessel, Annett et al., A Pandemic Influenza H1N1 Live Vaccine Based on Modified Vaccinia Ankara Is Highly Immunogenic and Protects Mice in Active and Passive Immunizations, PLoS One, 2010, 1-11, 5(8):e12217.
Holtkamp, Derald et al., The economic cost of major health challenges in large US swine production systems, The American Association of Swine Veterinarians Annual Meeting, 2007, 85-89, N/A.
Johansson, B.E. et al., Immunization with purified N1 and N2 influenza virus neuraminidases demonstrates cross-reactivity without antigenic competition, Proc. Natl. Acad. Sci. USA, 1994, 2358-2361, 91(6).
Kamrud, K.I. et al., Development and characterization of promoterless helper RNAs for the production of alphavirus replicon particle, Journal of General Virology, 2010, 1723-1727, 91(Pt 7).
Katoh, Kazutaka et al., MAFFT Multiple Sequence Alignment Software Version 7: Improvements in Performance and Usability, Mol. Biol. Evol., 2013, 772-780, 30(4).
Katoh, Kazutaka et al., MAFFT: a novel method for rapid multiple sequence alignment based on fast Fourier transform, Nucleic Acids Research, 2002, 3059-3066, 30(14).
Kilbourne, Edwin D. et al., Protection of Mice with Recombinant Influenza Virus Neuraminidase, The Journal of Infectious Diseases, 2004, 459-461, 189(3).
Kitikoon, Pravina et al., Hemagglutinin Inhibition Assay with Swine Sera, Methods in Molecular Biology, 2014, 295-301, 1161.
Klingbeil, Katharina et al., Protection of pigs against pandemic swine origin H1N1 influenzaA virus infection by hemagglutinin- or neuraminidase-expressingattenuated pseudorabies virus recombinants, Virus Research, 2015, 20-30, 199.
Krueger, Whitney S. et al., Swine Influenza Virus Infections in Man, Curr Top Microbiol Immunol, 2013, 201-225, 370.
Kumar, Sudhir et al., MEGA-CC: computing core of molecular evolutionary genetics analysis program for automated and iterative data analysis, Bioinformatics, 2012, 2685-2686, 28.
Kuntz-Simon, G. et al., Genetic and Antigenic Evolution of Swine Influenza Viruses in Europe and Evaluation of Their Zoonotic Potential, Zoonoses and Public Health, 2009, 310-325, 56(6-7).
Kyriakis, C.S. et al., Efficacy of commercial swine influenza vaccines against challenge with a recent European H1N1 field isolate, Veterinary Microbiology, 2010, 67-74, 144(1-2).
Lee, Jee Hoon et al., Efficacy of swine influenza A virus vaccines against an H3N2 virus variant, The Canadian Journal of Veterinary Research, 2007, 207-212, 71(3).
Liljestrom, P. et al., A new generation of animal cell expression vectors based on the semliki forest virus replicon, Biotechnology, 1991, pp. 1356-1361, 9.
Mehle, Andrew, Unusual Influenza A Viruses in Bats, Viruses, 2014, 3438-3440, 6(9).
Memoli, Matthew J. et al., Evaluation of Antihemagglutinin and Antineuraminidase Antibodies as Correlates of Protection in an Influenza A/H1N1 Virus Healthy Human Challenge Model, mBio, 2016, 1-12, 7(2):e00417-16.
Monto, Arnold S. et al., Antibody to Influenza Virus Neuraminidase: An Independent Correlate of Protection, The Journal of Infectious Diseases, 2015, 1191-1199, 212(8).
Murphy, Brian R. et al., Association of Serum Anti-Neuraminidase Antibody with Resistance to Influenza in Man, The New England Journal of Medicine, 1972, 1329-1332, 286(25).

Nayak, Baibaswata et al., Contributions of the Avian Influenza Virus HA, NA, and M2 Surface Proteins to the Induction of Neutralizing Antibodies and Protective Immunity, Journal of Virology, 2010, 2408-2420, 84(5).
Nelson, M, Evolution of Novel Reassortant A/H3N2 Influenza Viruses in North American Swine and Humans, 2009-2011, Journal of Virology, 2012, 8872-8878, vol. 86, No. 16.
Nelson, Martha I. et al., Reverse zoonosis of influenza to swine: new perspectives on the human-animal interface, Trends in Microbiol., 2015, 142-153, 23(3).
Pavlova, S.P. et al., Protection of chickens against H5N1 highly pathogenic avian virus infection by live vaccination with infectious laryngotracheitis virus recombinants expressing H5 hemagglutinin and N1 neuraminidase, Vaccine, 2009, pp. 773-785, vol. 27.
Price, Morgan N. et al., FastTree 2—Approximately Maximum-Likelihood Trees for Large Alignments, PLoS One, 2010, 1-10, 5(3): e9490.
Pushko, Peter et al., Replicon-Helper Systems from Attenuated Venezuelan Equine Encephalitis Virus: Expression of Heterologous Genes in Vitro and Immunization against Heterologous Pathogens in Vivo, Virology, 1997, 389-401, 239.
Sandbulte, Matthew R. et al., Analyzing Swine Sera for Functional Antibody Titers Against Infl uenza A Neuraminidase Proteins Using an Enzyme-Linked Lectin Assay (ELLA), Methods in Molecular Biology, 2014, 337-345, 1161.
Sylte, Matthew J. et al., Influenza neuraminidase antibodies provide partial protection for chickens against high pathogenic avian influenza infection, Vaccine, 2007, 3763-3772, 25(19).
Tong, Suxiang et al., A distinct lineage of influenza A virus from bats, PNAS, 2012, 4269-4274, 109(11).
Tripp, Ralph A. et al., Animal Models for Evaluation of Influenza Vaccines, Current Topics in Microbiology and Immunology, 2009, 397-412, 333.
Vander Veen, RL et al., Alphavirus replicon vaccines, Animal Health Research Reviews, 2012, 1-9, vol. 13, No. 1.
Vander Veen, RL et al., Safety, immunogenicity, and efficacy of an alphavirus replicon-based swine influenza virus hemagglutinin vaccine, Vaccine, 2012, 1944-1950, vol. 30, No. 11.
Vincent, Amy L. et al., Efficacy of inactivated swine influenza virus vaccines against the 2009 A/H1N1 influenza virus in pigs, Vaccine, 2010, 2782-2787, 28(15).
Watson, Simon J. et al., Molecular Epidemiology and Evolution of Influenza Viruses Circulating within European Swine between 2009 and 2013, Journal of Virology, 2015, 9920-9931, 89(19).
Webster, Robert G. et al., Evolution and Ecology of Influenza A Viruses, Microbiological Reviews, 1992, 152-179, 56(1).
Kuznetsov, V.I., et al., Guideline for Diagnosis and Treatment of Swine Influenza, Peoples' Friendship University of Russia, 2009, 3-16, N/A.
Kuznetsov, V.I., et al., Guideline for Diagnosis and Treatment of Swine Influenza, Peoples' Friendship University of Russia, 2009, 3-16, N/A; English translation.
Abstract corrected by the examiner on 1 page.
Abstract corrected by the examiner on 1 page, machine translation.
Jagadesh, Anitha et al., Influenza virus neuraminidase (NA): a target for antivirals and vaccines, Arch Virol, 2016, 2087-2094, 161.
Kitikoon et al, Swine influenza matrix 2 (M2) protein contributes to protection against infection with different H1 swine influenza virus (SIV) isolates, Vaccine, 2010, 523-531, 28.
Li et al., The epidemiology of swine influenza, Animal Diseases, 2021, 1-14.
Li, Haozhou et al., Novel Capsid-Specific Single-Domain Antibodies with Broad Foot-and-Mouth Disease Strain Recognition Reveal Differences in Antigenicity of Virions, Empty Capsids, and Virus-Like Particles, Vaccines, 2021, 1-20, 9:620.
Rajao, et al., Pathogenesis and Vaccination of Influenza A Virus in Swine, Influenza Pathogenesis and Control—vol. I, 2014, 307-326, 385.
Rose, et al., Dynamics of influenza A virus infections in permanently infected pig farms: evidence of recurrent Infections, circulation of several swine influenza viruses and reassortment events, Veterinary Research, 2013, 72-86, 44.

(56) References Cited

OTHER PUBLICATIONS

Vincent, Amy I. et al., Influenza A virus vaccines for swine, Veterinary Microbiology, 2017, 35-44, 206.
Eichelberger, Maryna C. et al., Influenza Neuraminidase as a Vaccine Antigen, Influenza Pathogenesis and Control-vol. II, II, 275-299, 2014.
Sylte, Matthew J. et al., Influenza neuraminidase as a vaccine antigen, Curr Top Microbiol Immunol, 333, 227-241, 2009.

* cited by examiner

SWINE INFLUENZA A VIRUS VACCINE

CROSS-REFERENCE TO RELATED APPLICATIONS

This application is a U.S. National Phase application under 35 U.S.C. § 371 of PCT/EP2018/085198, filed on Dec. 17, 2018, which claims the benefit of U.S. Provisional Application No. 62/607,101, filed on Dec. 18, 2017. The contents of the U.S. Provisional Application No. 62/607,101 and PCT/EP2018/085198 are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jun. 16, 2020, is named 24554USPCT-SEQLIST-16JUN2020.txt and is 70,311 bytes in size.

FIELD OF THE INVENTION

The present invention relates to vectors and/or nucleic acid constructs that encode one or more influenza A virus neuraminidase (NA) antigens. The present invention further relates to vaccines against influenza A virus comprising these vectors and/or nucleic acid constructs. The present invention also relates to methods of making and using the vaccines alone or in combination with other protective agents.

BACKGROUND

Influenza A viruses (IAV) create a significant burden on human and animal health, worldwide. A member of the Orthomyyxoviridae family, IAV is categorized into different subtypes based on its viral surface glycoproteins, hemagglutinin (HA) and neuraminidase (NA). IAV infects poultry, pigs, horses, cats, dogs, marine mammals (e.g., whales), bats and humans. Wild waterfowl and shorebirds (ducks, geese, swans and gulls) are the natural reservoirs and they can be infected with 16 different HA and 9 different NA subtypes [Webster et al., *Microbiol Rev* 56:152-179 (1992)]. Recently two new subtypes, H17N10 and H18N11 were identified in bats [Tong et al., *Proc. Natl. Acad. Sci.* 109 (11): 4269-4274 (2012) and Mehle, *Viruses* 6 (9): 3438-3449 (2014)]. Interspecies transmission of the virus occurs most frequently between wild and domestic waterfowl and between pigs and human [Nelson and Vincent, 23 (3) Trends in *Microbiol.* 142-153 (2015)]. Mammals infected with IAV demonstrate acute respiratory disease resulting in an aerosol viral transmission. In waterfowl and domesticated poultry the virus can replicate in both the respiratory and intestinal tract and are spread through fecal-oral route.

One such IAV, swine influenza A virus (IAV-S) is a serious respiratory pathogen of domestic pigs that has proven to be economically costly, particularly to the livestock industry, worldwide [Holtkamp et al., *The American Association of Swine Veterinarians Annual Meeting* (2007)]. Moreover, the transmission of influenza viruses of swine-origin to humans has been well documented and represents a significant public health threat, which therefore, provides an even greater incentive to control influenza A virus in swine herds [Krueger and Gray, *Curr Top Microbiol Immunol* 370: 201-225 (2013)].

In response to this problem, many swine farmers now vaccinate their pigs against IAV-S employing commercially available vaccines. However, controlling IAV-S with the conventional vaccines is difficult because many diverse IAV-S strains co-circulate in the field and continue to evolve [Gao et al., *J Gen Virol* 98(8):2001-2010 (2017)]. The diversity and mutability of IAV-S are caused by the virus's genetic structure. Like other influenza A viruses, IAV-S has genes encoded on eight segments of RNA and a genome replication machinery that introduces frequent mutations. These genetic characteristics enable IAV-S to make rapid adaptions, including escape from existing neutralizing antibodies induced by exposure to previous strains. Consequently, inactivated virus IAV-S vaccines that are commercially available in the US market have proven inadequate despite comprising up to five different IAV-S strains due to newly emerging strains that arise as a consequence of the continuous antigenic drift.

Classification of influenza A viruses starts with subtyping of HA and NA, the two major glycoproteins on the virus surface. HA protein mediates attachment and fusion of the virus to host cells. Antibodies that bind to HA block: viral attachment, virus replication, and reduce or even prevent disease. Neuraminidase is an enzyme that functions in the final stage of the influenza virus replication cycle by cleaving newly formed viral particles from the host cell, thereby enabling the new progeny virus to spread and infect other cells. Antibodies that bind to NA restrict its enzymatic activity and thereby can reduce the level of virus spread and disease severity in certain animal models.

Whereas human influenza A usually has 1 or 2 dominant strains circulating globally during a given influenza season, many more strains of IAV-S co-circulate simultaneously, with these strains differ between geographic regions. IAV-S strains are antigenically variable, but mainly contain an H1 or H3 subtype of HA, and a N1 or N2 subtype of NA. Within each HA and NA subtype of IAV-S there is further phylogenetic diversity. In the US swine population there are four predominant phylogenetic clusters of H1 (gamma, delta1, delta2, pandemic), two predominant clusters of H3 (cluster IV and human-like), two predominant clusters of N1 (classic, pandemic), and two predominant clusters of N2 (N2-1998 and N2-2002). [See, Anderson et al., *Influenza and other Respiratory Viruses* 7 (Suppl. 4); 42-51 (2013); and Anderson et al., *mSphere* 1(6) e00275-16:1-14 (2016)]. In Europe there are three major lineages of H1 (Eurasian-avian like H1, Scotland/410440/1994-like H1 and pandemic 2009 like H1), one major lineage of H3 (Gent/1/1984-like H3), two major lineages of N1 (Eurasian Avian-like N1, Pandemic 2009 like N1), two major lineages of N2 (Gent/1/1984-like N2, Scotland/410440/1994-like N2) and two minor lineages of N2 (Italy/4675/2003 like N2, Human seasonal like N2) [Watson et al., *J. Virol.*, 89:9920-9931 (2015); doi:10.1128/JV1.00840-15].

A number of vector-based strategies have been employed through the years for vaccines in an effort to protect against certain pathogens. One such vector strategy includes the use of alphavirus-derived replicon RNA particles (RP) [Vander Veen, et al. *Anim Health Res Rev.* 13(1):1-9. (2012) doi: 10.1017/S1466252312000011; Kamrud et al., *J Gen Virol.*, 91(Pt 7):1723-1727 (2010)] which have been developed from several different alphaviruses, including Venezuelan equine encephalitis virus (VEE) [Pushko et al., Virology 239:389-401 (1997)], Sindbis (SIN) [Bredenbeek et al., Journal of Virology 67:6439-6446 (1993)], and Semliki Forest virus (SFV) [Liljestrom and Garoff, Biotechnology (NY) 9:1356-1361 (1991)]. RP vaccines deliver propagation-defective alphavirus RNA replicons into host cells and result in the expression of the desired antigenic transgene(s) in vivo [Pushko et al., *Virology* 239(2):389-401 (1997)]. RPs have an attractive safety and efficacy profile when compared to some traditional vaccine formulations [Vander Veen, et al. Anim Health *Res Rev.* 13(1):1-9. (2012)]. The RP platform has been used to encode pathogenic antigens and is the basis for several USDA-licensed vaccines for swine and poultry.

As noted above, commercial IAV-S vaccines available for use in domestic swine often fail to protect herds because the antigens do not match all contemporary strains circulating in the field [Lee et al., *Can J Vet Res* 71(3): 207-12(2007); Vincent et al., *Vaccine* 28(15):2782-2787 (2010)]. The conventional platform of inactivated virus antigens is constrained by regulatory and manufacturing factors that limit the capacity to rapidly update vaccine strains in response to ongoing virus antigenic drift. With conventional inactivated virus IAV-S vaccines the choice of viral strains is based on HA antigen properties. The serological evaluation of immune responses is similarly focused on measuring antibodies to that HA. The same emphasis on the HA antigen is also true for commercially inactivated influenza virus vaccines marketed for humans, as well as other influenza-susceptible animal species (e.g., avian, equine, canine). IAV-S vaccines that induce HA inhibiting (HI) antibody titers protect pigs against experimental infection with an antigenically similar strain [Kyriakis et al., *Vet Microbiol* 144(1-2):67-74 (2010)]. However, relatively rapid genetic drift of the HA genes allows new strains to emerge that are not functionally inhibited by the vaccine-induced HA antibodies.

Clinical studies have shown a statistically significant correlation between NA-specific antibody titers and reduced influenza disease incidence in humans [Memoli et al., *MBio* 7(2):e00417-16. (2016); Monto et al., *J Infect Dis* 212(8): 1191-1199 (2015); Murphy et al., *N Engl J Med* 286 (25):1329-32 (1972)]. Various studies performed in inbred mice showed that NA-specific immunity can protect against a challenge infection [Brett and Johansson, *Virology* 339(2): 273-80 (2005); Johansson and Kilbourne, *Proc Natl Acad Sci USA* 91(6): 2358-2361 (1994); Kilbourne et al., *J Infect Dis* 189(3): 459-461(2004)]. Hessel et al. [PLoS One 5(8), e12217 (2010)] showed that a vaccine comprising a recombinant poxvirus vector encoding an IAV-S NA could partially induce protection of mice against a viral challenge, though the poxvirus-vectored NA was less efficacious than the equivalent vaccine encoding the corresponding HA gene. Importantly however, the use of mice as an animal model for influenza cannot be taken as a reliable predictor of vaccine efficacy because unlike pigs, avians, and humans, mice are not a natural host for influenza A viruses, [Bodewes et al., *Expert Rev Vaccines* 9(1):59-72 (2010); Tripp and Tompkins, *Curr Top Microbiol Immunol* 333:397-412 (2009); Vander Veen et al., *Vaccine* 30(11):1944-1950 (2012)]. Indeed, viral strains must first be adapted to grow in mice, because this species is not naturally susceptible to influenza A virus infection. Accordingly, the pathogenesis and disease are presented by weight loss and mortality, which is different from the infection parameters used for a natural host.

Analogous studies were performed in chickens, a natural host species for influenza using a virally vectored NA vaccine against a challenge infection. The NA immunity in chickens only conferred partial protection against the infections, and was significantly less robust than that induced by an equivalent vectored HA vaccine [Nayak et al., *J Virol* 84(5): 2408-2420 (2010); Pavlova et al., *Vaccine* 27(5): 773-785 (2009); Sylte et al., *Vaccine* 25(19): 3763-72 (2007)]. Similar results were reported in another naturally susceptible influenza host, a ferret, was vaccinated with soluble recombinant NA and/or HA proteins, followed by a viral challenge [Bosch et al., *J Virol* 84(19):10366-103674 (2010)]. Taken together these data imply that NA immunity only can play a supplemental and/or complementary role to the more critical HA immunity. Indeed, it appears that in the absence of a hemagglutinin antigen, a neuraminidase influenza A virus vaccine is not potent enough to either protect against influenza A infection or protect against an influenza A virus induced disease.

A single published study tested an attenuated pseudorabies virus (PrV) vectored NA vaccine against a viral challenge infection in pigs [Klingbeil et al., *Virus Res* 199: 20-30(2015)]. Notably, the inclusion of the PrV-NA with the PrV-HA provided no significant improvement over the protection induced by PrV-HA by itself. Data from the study did show that the PrV-NA vaccine, whether administered alone or co-administered with PrV-HA vaccine, induced serum antibodies to the NA protein. However, despite the antibodies being generated, the NA-vaccinated pigs only showed a very modest reduction in magnitude of viral replication (statistically significant at only a single sample day: 4 days post-infection). As expected, the pigs vaccinated solely with PrV-HA vector induced HI antibody responses, but these responses correlated with a more pronounced reduction in virus shedding (statistically significant from 2-6 days post-infection). Indeed heretofore, there have been no published studies that indicate that an IAV-S vaccine comprising and/or encoding an influenza A neuraminidase antigen in the absence of the corresponding hemagglutinin antigen can adequately protect a pig against an IAV-S infection.

The citation of any reference herein should not be construed as an admission that such reference is available as "prior art" to the instant application.

SUMMARY OF THE INVENTION

Accordingly, the present invention provides vectors and/or nucleic acid constructs that encode one or more influenza A virus neuraminidase (NA) antigens. These vectors and/or nucleic acid constructs can be used in immunogenic compositions comprising these vectors. The immunogenic compositions of the present invention may be used in vaccines that aid in the protection of the vaccinated subject (e.g., a human, companion animal, or livestock) against influenza A virus, e.g., aid in the prevention of influenza A virus infection. In particular embodiments, immunogenic compositions and the vaccines of the present invention comprising one or more NAs that originate from an influenza A virus neither comprises an influenza virus hemagglutinin (HA) or an antigenic fragment thereof, nor a nucleotide sequence that encodes an influenza A virus HA or an antigenic fragment thereof.

In certain embodiments, vectors and/or nucleic acid constructs are provided that encode one or more human influenza A virus NA antigens. In other embodiments, the vectors and/or nucleic acid constructs encode one or more canine influenza virus NA antigens. In still other embodiments, the vectors and/or nucleic acid constructs encode one or more equine influenza virus NA antigens. In yet other embodiments, the vectors and/or nucleic acid constructs encode one or more avian influenza virus NA antigens. In still other embodiments, the vectors and/or nucleic acid constructs encode one or more bovine influenza virus NA antigens. In specific embodiments, the vectors and/or nucleic acid constructs encode two to four influenza virus NA antigens.

In specific embodiments, the vector is an alphavirus RNA replicon particle that encodes one or more antigens that originate from an influenza A virus. In particular embodiments, the alphavirus RNA replicon particle encodes one or more influenza A virus NAs. In related embodiments, the alphavirus RNA replicon particle encodes one or more antigenic fragments of one or more influenza A virus NAs. The present invention also includes other vectors and/or nucleic acid constructs that encode one or more antigens that originate from swine influenza A virus (IAV-S). In particular embodiments, the vectors and/or nucleic acid constructs can also encode one or more IAV-S neuraminidase antigens (NAs). In related embodiments, vectors and/or nucleic acid constructs can encode one or more IAV-S antigenic fragments of one or more NAs.

In one important aspect of the present invention, vectors and/or nucleic acid constructs are provided that encode one or more swine influenza A virus (IAV-S) neuraminidase (NA) antigens. Such vectors and/or nucleic acid constructs can be used in immunogenic compositions comprising these vectors. The immunogenic compositions of the present invention may be used in vaccines that aid in the protection of the vaccinated porcine subject (e.g., a sow and/or a piglet) against IAV-S, e.g., aid in the prevention of swine influenza virus infection. In particular embodiments, immunogenic compositions and the vaccines comprising one or more NAs that originate from an IAV-S of the present invention neither comprises an IAV-S HA or an antigenic fragment thereof, nor a nucleotide sequence that encodes a IAV-S HA or an antigenic fragment thereof. The present invention further provides combination vaccines for eliciting protective immunity against IAV-S and other diseases, e.g., other swine infectious diseases. Methods of making and using the immunogenic compositions and vaccines of the present invention are also provided.

In more specific embodiments, the vector is an alphavirus RNA replicon particle that encodes one or more antigens that originate from IAV-S. In particular embodiments, the alphavirus RNA replicon particle encodes one or more IAV-S NAs. In related embodiments, the alphavirus RNA replicon particle encodes one or more antigenic fragments of one or more IAV-S NAs. In particular embodiments, alphavirus RNA replicon particles encoding one or more NAs that originate from an IAV-S of the present invention neither comprise an IAV-S HA or an antigenic fragment thereof, nor encode a nucleotide sequence that encodes a IAV-S HA or an antigenic fragment thereof.

In certain embodiments, the IAV-S NA originates from a N1-classic phylogenetic cluster. In other embodiments, the alphavirus RNA replicon particle encodes an antigenic fragment of a NA that originates from a N1-classic phylogenetic cluster. In still other embodiments, the IAV-S NA originates from a N2-1998 phylogenetic cluster. In yet other embodiments, the alphavirus RNA replicon particle encodes an antigenic fragment of a NA that originates from a N2-1998 phylogenetic cluster. In still other embodiments, the IAV-S NA originates from a N1-pandemic phylogenetic cluster. In yet other embodiments, the alphavirus RNA replicon particle encodes an antigenic fragment of a NA that originates from a N1-pandemic phylogenetic cluster. In still other embodiments, the IAV-S NA originates from a N2-2002 phylogenetic cluster. In yet other embodiments, the alphavirus RNA replicon particle encodes an antigenic fragment of a NA that originates from a N2-2002 phylogenetic cluster.

In an analogous embodiment, the IAV-S NA originates from—and/or the alphavirus RNA replicon particle encodes (an antigenic fragment of) a NA from a N1-pandemic (EU) lineage. In an analogous embodiment, the IAV-S NA originates from—and/or the alphavirus RNA replicon particle encodes (an antigenic fragment of) a NA from a N1-Eurasian Avian lineage.

In an analogous embodiment, the IAV-S NA originates from—and/or the alphavirus RNA replicon particle encodes (an antigenic fragment of) a NA from a N2-Gent/1984 lineage. In another analogous embodiment, the IAV-S NA originates from—and/or the alphavirus RNA replicon particle encodes (an antigenic fragment of) a NA from a N2-Italy/2003 lineage. In still an analogous embodiment, the IAV-S NA originates from—and/or the alphavirus RNA replicon particle encodes (an antigenic fragment of) a NA from a N2-Scotland/1994 lineage. In certain embodiments of this type, the IAV-S NA originates from—and/or the alphavirus RNA replicon particle encodes (an antigenic fragment of) a NA from a N2-Scotland/1994 lineage (clade 1). In other embodiments of this type, the IAV-S NA originates from—and/or the alphavirus RNA replicon particle encodes (an antigenic fragment of) a NA from a N2-Scotland/1994 lineage (clade 2). In still other embodiments of this type, the IAV-S NA originates from—and/or the alphavirus RNA replicon particle encodes (an antigenic fragment of) a NA from a A/Swine/Italy/4675/2003 like N2. In still other embodiments of this type, the IAV-S NA originates from—and/or the alphavirus RNA replicon particle encodes (an antigenic fragment of) a NA from a Human seasonal like N2.

In particular embodiments, the IAV-S NA that originates from a N1-classic phylogenetic cluster comprises an amino acid sequence comprising 95% identity, 97% identity, 98% identity, or more with the amino acid sequence of SEQ ID NO: 2. In more specific embodiments of this type, the NA comprises the amino acid sequence of SEQ ID NO: 2. In even more specific embodiments of this type the NA is encoded by the nucleotide sequence of SEQ ID NO: 1. In other embodiments, the IAV-S NA that originates from a N1-pandemic phylogenetic cluster comprises an amino acid sequence comprising 95% identity, 97% identity, 98% identity, or more with the amino acid sequence of SEQ ID NO: 4. In more specific embodiments of this type, the NA comprises the amino acid sequence of SEQ ID NO: 4. In even more specific embodiments of this type the NA is encoded by the nucleotide sequence of SEQ ID NO: 3. In yet other embodiments, the IAV-S NA that originates from a N2-1998 phylogenetic cluster comprises an amino acid sequence comprising 92% identity, 94% identity, 97% identity, or more with the amino acid sequence of SEQ ID NO: 6. In more specific embodiments of this type, the NA comprises the amino acid sequence of SEQ ID NO: 6. In even more specific embodiments of this type the NA is encoded by the nucleotide sequence of SEQ ID NO: 5. In yet other embodiments, the IAV-S NA that originates from a N2-2002 phylogenetic cluster comprises an amino acid sequence comprising 92% identity, 94% identity, 97% identity, or more with the amino acid sequence of SEQ ID NO: 8. In more specific embodiments of this type, the NA comprises the amino acid sequence of SEQ ID NO: 8. In even more specific embodiments of this type the NA is encoded by the nucleotide sequence of SEQ ID NO: 7.

In particular embodiments, the IAV-S NA that originates from a N1-pandemic (EU) lineage comprises an amino acid sequence comprising 90% identity, 92% identity, 95% identity, or more with the amino acid sequence of SEQ ID NO: 12. In more specific embodiments of this type, the NA comprises the amino acid sequence of SEQ ID NO: 12. In even more specific embodiments of this type the NA is encoded by the nucleotide sequence of SEQ ID NO: 11. In related embodiments of this type the NA is encoded by the nucleotide sequence of SEQ ID NO: 23. In other embodiments, the IAV-S NA that originates from a N1-Eurasian Avian lineage comprises an amino acid sequence comprising 85% identity, 90% identity, 95% identity, or more with the amino acid sequence of SEQ ID NO: 14. In more specific embodiments of this type, the NA comprises the amino acid sequence of SEQ ID NO: 14. In even more specific embodiments of this type the NA is encoded by the nucleotide sequence of SEQ ID NO: 13. In yet other embodiments, the IAV-S NA that originates from a N2-Gent/1984 lineage comprises an amino acid sequence comprising 90% identity, 92% identity, 95% identity, or more with the amino acid sequence of SEQ ID NO: 16. In more specific embodiments of this type, the NA comprises the amino acid sequence of SEQ ID NO: 16. In even more specific embodiments of this type the NA is encoded by the nucleotide sequence of SEQ ID NO: 15. In related embodiments of this type the NA is encoded by the nucleotide sequence of SEQ ID NO: 24. In yet other embodiments, the IAV-S NA that originates from a N2-Italy/2003 lineage comprises an amino acid sequence comprising 90% identity, 92% identity, 95% identity or more with the amino acid sequence of SEQ ID NO: 18. In more specific embodiments of this type, the NA comprises the amino acid sequence of SEQ ID NO: 18. In even more specific embodiments of this type the NA is encoded by the nucleotide sequence of SEQ ID NO: 17. In related embodiments of this type the NA is encoded by the nucleotide sequence of SEQ ID NO: 25. In other embodiments, the IAV-S NA that originates from a N2-Scotland/1994 (clade 1) lineage comprises an amino acid sequence comprising 90% identity, 92% identity, 95% identity or more with the amino acid sequence of SEQ ID NO: 20. In more specific embodiments of this type, the NA comprises the amino acid sequence of SEQ ID NO: 20. In even more specific embodiments of this type the NA is encoded by the nucleotide sequence of SEQ ID NO: 19. In related embodiments of this type the NA is encoded by the nucleotide sequence of SEQ ID NO: 26. In yet other embodiments, the IAV-S NA that originates from a N2-Scotland/1994 (clade 2) lineage comprises an amino acid sequence comprising 90% identity, 92% identity, 95% identity or more with the amino acid sequence of SEQ ID NO: 22. In more specific embodiments of this type, the NA comprises the amino acid sequence of SEQ ID NO: 22. In even more specific embodiments of this type the NA is encoded by the nucleotide sequence of SEQ ID NO: 21. In related embodiments of this type the NA is encoded by the nucleotide sequence of SEQ ID NO: 27.

In still more particular embodiments, the alphavirus RNA replicon particle is a Venezuelan Equine Encephalitis (VEE) alphavirus RNA replicon particle. In yet more specific embodiments the VEE alphavirus RNA replicon particle is a TC-83 VEE alphavirus RNA replicon particle. In other embodiments, the alphavirus RNA replicon particle is a Sindbis (SIN) alphavirus RNA replicon particle. In still other embodiments, the alphavirus RNA replicon particle is a Semliki Forest virus (SFV) alphavirus RNA replicon particle. In an alternative embodiment a naked DNA vector comprises a nucleic acid construct that encodes one or more antigens that originate from a porcine pathogen. In particular embodiments of this type, a naked DNA vector comprises a nucleic acid construct that encodes a NA that originates from an IAV-S, or antigenic fragment thereof. In still other embodiments a naked RNA vector comprises a nucleic acid construct that encodes one or more antigens that originate from a porcine pathogen. In particular embodiments of this type, a naked RNA vector comprises a nucleic acid construct that encodes a NA that originates from an IAV-S, or antigenic fragment thereof.

The present invention provides alphavirus RNA replicon particles that encode two or more IAV-S antigens or antigenic fragments thereof. In particular embodiments, alphavirus RNA replicon particles encoding one or more NAs that originate from an IAV-S of the present invention neither comprise an IAV-S HA or an antigenic fragment thereof, nor encode a nucleotide sequence that encodes a IAV-S HA or an antigenic fragment thereof.

In specific embodiments, the alphavirus RNA replicon particles encode two to four or more NA antigens that originate from IAV-S, or antigenic fragments thereof. In related embodiments, the alphavirus RNA replicon particles that encode two to four or more NA antigens that originate from different IAV-S phylogenetic clusters, or antigenic fragments thereof. In certain embodiments, the alphavirus RNA replicon particle encodes a NA originating from a N1-classic phylogenetic cluster or antigenic fragment thereof and a NA originating from a N2-2002 phylogenetic cluster or an antigenic fragment thereof. In other embodiments, the alphavirus RNA replicon particle encodes a NA originating from a N1-classic phylogenetic cluster or antigenic fragment thereof and a NA originating from a N2-1998 phylogenetic cluster or an antigenic fragment thereof. In still other embodiments, the alphavirus RNA replicon particle encodes a NA originating from a N1-classic phylogenetic cluster or antigenic fragment thereof and a NA originating from a N1-pandemic phylogenetic cluster or an antigenic fragment thereof.

In certain embodiments, the alphavirus RNA replicon particles encode a NA originating from a N1-pandemic (EU) lineage or antigenic fragment thereof and a NA originating from a N1-Eurasian Avian lineage or an antigenic fragment thereof. In other embodiments the alphavirus RNA replicon particles encode a NA originating from a N2-Gent/1984 lineage or antigenic fragment thereof and a NA originating from a N2-Italy/2003 lineage or an antigenic fragment thereof. In still other embodiments the alphavirus RNA replicon particles encode a NA originating from a N2-Gent/1984 lineage or antigenic fragment thereof and a NA originating from a N2-Scotland/1994 (clade 1) lineage or an antigenic fragment thereof. In yet other embodiments the alphavirus RNA replicon particles encode a NA originating from a N2-Gent/1984 lineage or antigenic fragment thereof and a NA originating from a N2-Scotland/1994 (clade 2) lineage or an antigenic fragment thereof. In still other embodiments the alphavirus RNA replicon particles encode a NA originating from a N2-Italy/2003 lineage or an antigenic fragment thereof and a NA originating from a N2-Scotland/1994 (clade 1) lineage or antigenic fragment thereof. In yet other embodiments the alphavirus RNA replicon particles encode a NA originating from a N2-Italy/2003 lineage or an antigenic fragment thereof and a NA originating from a N2-Scotland/1994 (clade 2) lineage or an antigenic fragment thereof. In still other embodiments, a NA originating from one of the European N1 lineages or an antigenic fragment thereof is encoded in the alphavirus RNA replicon particle, along with a NA originating from one of the European N2 lineages or an antigenic fragment thereof. Similarly, the present invention includes alphavirus RNA replicon particles encoding three, four, or more NAs, with each NA originating from a different European lineage. Furthermore, the present invention includes alphavirus RNA replicon particles encoding two, three, four, or more NAs, with each NA originating from a different European lineage and/or phylogenetic cluster.

Accordingly, the present invention further provides alphavirus RNA replicon particles that encode three or four IAV-S antigens or antigenic fragments thereof. In specific embodiments, the immunogenic compositions comprise alphavirus RNA replicon particles that encode three or four NA antigens that originate from IAV-S, or antigenic fragments thereof. In related embodiments, the immunogenic compositions comprise alphavirus RNA replicon particles that encode three or four NA antigens that originate from different IAV-S phylogenetic clusters, or antigenic fragments thereof. In certain embodiments, the alphavirus RNA replicon particle encodes a NA originating from a N1-classic phylogenetic cluster or antigenic fragment thereof, a NA originating from a N2-2002 phylogenetic cluster or an antigenic fragment thereof, and a NA originating from a N2-1998 phylogenetic cluster or an antigenic fragment thereof. In other embodiments, the alphavirus RNA replicon particle encodes a NA originating from a N1-classic phylogenetic cluster or antigenic fragment thereof, a NA originating from a N2-2002 phylogenetic cluster or an antigenic fragment thereof, and a NA originating from a N1-pandemic phylogenetic cluster or an antigenic fragment thereof. In other embodiments, the alphavirus RNA replicon particle encodes a NA originating from a N1-classic phylogenetic cluster or antigenic fragment thereof, a NA originating from a N2-1998 phylogenetic cluster or an antigenic fragment thereof, and a NA originating from a N1-pandemic phylogenetic cluster or an antigenic fragment thereof. In other embodiments, the alphavirus RNA replicon particle encodes a NA originating from a N2-2002 phylogenetic cluster or antigenic fragment thereof, a NA originating from a N2-1998 phylogenetic cluster or an antigenic fragment thereof, and a NA originating from a N1-pandemic phylogenetic cluster or an antigenic fragment thereof.

In specific embodiments, the alphavirus RNA replicon particles encode four or more IAV-S NA antigens or antigenic fragments thereof. In more specific embodiments, the alphavirus RNA replicon particles encode four or more NA antigens that originate from different IAV-S phylogenetic clusters, or antigenic fragments thereof. In even more specific embodiments the alphavirus RNA replicon particle encodes a NA originating from a N2-2002 phylogenetic cluster or antigenic fragment thereof, a NA originating from a N2-1998 phylogenetic cluster or an antigenic fragment thereof, a NA originating from a N1-pandemic phylogenetic cluster or an antigenic fragment thereof, and a NA originating from a N1-classic phylogenetic cluster or an antigenic fragment thereof.

In analogous embodiments as outlined above, the alphavirus RNA replicon particle encodes three, four, or more IAV-S NA antigens or antigenic fragments thereof originating from an IAV-S N1-pandemic (EU) lineage, a N1-Eurasian Avian lineage, a NA lineage, a N2-Gent/1984 lineage, a N2-Italy/2003 lineage, a N2-Scotland/1994 (clade 1) lineage, and/or a N2-Scotland/1994 (clade 2) lineage.

As indicated above, all of the alphavirus RNA replicon particles of the present invention can be components of immunogenic compositions and/or vaccines. Accordingly, an immunogenic composition and/or vaccine of the present invention can comprise one or more of the alphavirus RNA replicon particles of the present invention. In certain embodiments, an immunogenic composition and/or vaccine comprises only a single set of identical alphavirus RNA replicon particles, which can encode one or more NAs originating from one or more phylogenetic clusters and/or one or more lineages, as detailed above.

In a more specific embodiment of this type the immunogenic composition and/or vaccine comprises RNA replicon particles that encode both a NA (or an antigenic fragment thereof) originating from a N1-phylogentic cluster and a NA (or an antigenic fragment thereof) originating from a N2-phylogentic cluster. In particular, the immunogenic composition and/or vaccine comprises an RNA replicon wherein a first NA is of a N1-phylogentic cluster selected from the group of a N1-classic- and N1-pandemic phylogenetic cluster and a second NA is of a N2-phylogenetic cluster selected from the group consisting of a N2-1998— and N2-2002 phylogenetic cluster.

In further particular embodiments of this type the immunogenic composition and/or vaccine comprises an RNA replicon wherein a first NA is of a N1-lineage selected from the group consisting of a N1-pandemic (EU) and N1-Eurasian Avian lineage and a second NA is of a N2-phylogenetic lineage selected from the group consisting of a N2-Gent/1984-, N2-Italy/2003-N2-Scotland 1994 (clade 1) lineage, and N2-Scotland 1994 (clade 2) lineage.

The present invention further provides immunogenic compositions and/or vaccines that comprise two or more sets of such alphavirus RNA replicon particles. In particular embodiments of this type, one set of alphavirus RNA replicon particles encodes one or more NAs originating from one phylogenetic cluster and/or lineage, whereas the other set of alphavirus RNA replicon particles encodes one or more NAs originating from another phylogenetic cluster and/or lineages.

In specific embodiments of this type, the first set of alphavirus RNA replicon particles encodes one or more NA antigens that originate from a N1-phylogenetic cluster and/or lineage, or antigenic fragments thereof, and the second set of alphavirus RNA replicon particles encode one or more NA antigens that originate from a N2-phylogenetic cluster and/or lineage, or antigenic fragments thereof. In particular, in the first set the NA antigen (or fragment thereof) is of a N1-phylogenetic cluster selected from the group consisting of a N1-classic- and N1-pandemic phylogenetic cluster and in the second set the NA antigen (or antigenic fragment thereof) is of a N2-phylogenetic cluster selected from the group consisting of a N2-1998— and N2-2002 phylogenetic cluster.

In a similar, parallel embodiment in the first set the NA antigen (or fragment thereof) is of a N1-phylogentic lineage selected from the group consisting of a N1-pandemic (EU)—and N1-Eurasian Avian lineage and in the second set the NA antigen (or antigenic fragment thereof) is of a N2-lineage selected from the group consisting of a N2-Gent/1984-, N2-Italy/2003-N2-Scotland 1994 (clade 1) lineage, and N2-Scotland 1994 (clade 2) lineage.

In yet other embodiments, the immunogenic composition and/or vaccine comprises one set of alphavirus RNA replicon particles that encode a first antigen, another set of alphavirus RNA replicon particles that encode a second antigen, and a third set of alphavirus RNA replicon particles that encode a third antigen. More specifically, in an immunogenic composition and/or vaccine the antigens are either NA-antigens of a phylogenetic cluster selected from the group consisting of a N1-classic-, N1-pandemic-, N2-1998- and N2-2002 phylogenetic cluster, or they are either NA-antigens of a lineage selected from the group consisting of a N1-pandemic (EU)-, N1-Eurasian Avian-, N2-Gent/1984-, N2-Italy/2003-N2-Scotland 1994 (clade 1) lineage, and N2-Scotland 1994 (clade 2) lineage.

In particular embodiments of this type, the first set of alphavirus RNA replicon particles encode a NA originating from a N1-classic phylogenetic cluster or an antigenic fragment thereof; the second set of alphavirus RNA replicon particles encode a NA originating from a N2-2002 phylogenetic cluster or antigenic fragment thereof; and the third set of alphavirus RNA replicon particles encode a NA originating from a N2-1998 phylogenetic cluster or an antigenic fragment thereof.

In yet other embodiments, the immunogenic composition and/or vaccine comprises one set of alphavirus RNA replicon particles that encode a first antigen, another set of alphavirus RNA replicon particles that encode a second antigen, a third set of alphavirus RNA replicon particles that encode a third antigen, and a fourth set of alphavirus RNA replicon particles that encode a fourth antigen.

More specifically, in an immunogenic composition and/or vaccine the antigens are either NA-antigens of a phylogenetic cluster selected from the group consisting of a N1-classic phylogenetic cluster, N1-pandemic phylogenetic cluster, N2-1998 phylogenetic cluster. and N2-2002 phylogenetic cluster, or they are NA-antigens of a lineage selected from the group consisting of a N1-pandemic (EU) lineage, N1-Eurasian Avian lineage, N2-Gent/1984 lineage, N2-Italy/2003 lineage, N2-Scotland 1994 (clade 1) lineage, and N2-Scotland 1994 (clade 2) lineage.

In particular embodiments of this type, the first set of alphavirus RNA replicon particles encode a NA originating from a N1-classic phylogenetic cluster or an antigenic fragment thereof; the second set of alphavirus RNA replicon particles encode a NA originating from a N2-2002 phylogenetic cluster or antigenic fragment thereof; the third set of alphavirus RNA replicon particles encode a NA originating from a N2-1998 phylogenetic cluster or an antigenic fragment thereof; and the fourth set of alphavirus RNA replicon particles encode a NA originating from a N1-pandemic phylogenetic cluster or an antigenic fragment thereof.

Accordingly, in one aspect of the present invention, the immunogenic compositions/vaccines comprise multiple sets (e.g., 2-10) of alphavirus RNA replicon particles. In particular embodiments of this type, one or more of the sets comprise alphavirus RNA replicon particles that encode one or more IAV-S NAs originating from one or more phylogenetic clusters (or antigenic fragments thereof) or lineages (or antigenic fragments thereof). In specific embodiments of this type, the immunogenic composition comprises one or more of the sets of alphavirus RNA replicon particles that encode one or more IAV-S NAs originating from one or more phylogenetic clusters or (or antigenic fragments thereof) or lineages (or antigenic fragments thereof), combined with one or more sets of alphavirus RNA replicon particles that encode one or more non-IAV-S antigens or antigenic fragments thereof. In even more specific embodiments, one or more of the sets of alphavirus RNA replicon particles encode both one or more IAV-S NAs originating from one or more phylogenetic clusters (or antigenic fragments thereof) or lineages (or antigenic fragments thereof) and encode one or more non-IAV-S antigens or antigenic fragments thereof. In specific embodiments of this type, the alphavirus RNA replicon particle encodes a NA originating from a N1-classic phylogenetic cluster or antigenic fragment thereof and/or a NA originating from a N2-2002 phylogenetic cluster or an antigenic fragment thereof, along with one to three non-IAV-S antigens or antigenic fragments thereof.

In particular embodiments, the non-IAV-S antigen originates from a porcine reproductive and respiratory syndrome virus (PRRS). In other embodiments, the non-IAV-S antigen originates from a porcine circovirus (PCV). In still other embodiments, the non-IAV-S antigen originates from a transmissible gastroenteritis virus (TGE). In yet other embodiments, the non-IAV-S antigen originates from a porcine pseudorabies virus (PPRV). In still other embodiments, the non-IAV-S antigen originates from a porcine parvovirus (PPV). In yet other embodiments, the non-IAV-S antigen originates from a porcine rotavirus (PRV). In still other embodiments, the non-IAV-S antigen originates from a porcine epidemic diarrhea virus (PED). In yet other embodiments, one or more non-IAV-S antigens originate from one or more serotypes of *Pasteurella multocida*. In still other embodiments, one or more non-IAV-S antigens originate from one or more serotypes of *Salmonella* ssp. In yet other embodiments, one or more non-IAV-S antigens originate from one or more serotypes of *Escherichia coli*. In still other embodiments, one or more non-IAV-S antigens originate from one or more serotypes of *Haemophilus parasuis*. In yet other embodiments, the non-IAV-S antigen originates from a *Lawsonia intracellularis*. In still other embodiments, the non-IAV-S antigen originates from a *Mycoplasma* ssp (e.g., *Mycoplasma hyopneumoniae*). In yet other embodiments, the non-IAV-S antigen originates from a *Bordetella bronchiseptica*. In still other embodiments, the non-IAV-S antigen originates from an Erysipelas ssp. In yet other embodiments, the non-IAV-S antigen originates from a *Campylobacter* ssp. In still other embodiments, the non-IAV-S antigen originates from an *Actinobacillus pleuropneumoniae*. In yet other embodiments, the non-IAV-S antigen originates from a *Clostridium perfringens*. In still other embodiments, the non-IAV-S antigen originates from a *Clostridium difficile*.

In more particular embodiments, the alphavirus RNA replicon particles are Venezuelan Equine Encephalitis (VEE) alphavirus RNA replicon particles. In yet more specific embodiments, the VEE alphavirus RNA replicon particles are TC-83 VEE alphavirus RNA replicon particles.

The present invention further provides combination immunogenic compositions and/or vaccines (multivalent vaccines) that include alphavirus RNA replicon particles that encode one or more NA or antigenic fragments thereof originating from IAV-S, as indicated above, and further comprise one or more modified live/attenuated or killed porcine pathogens. In particular embodiments, the immunogenic compositions further comprise one or more modified live/attenuated and/or killed PRRS virus. In other embodiments, the immunogenic compositions further comprise one or more modified live/attenuated and/or killed PCV. In yet other embodiments, the immunogenic compositions further comprise one or more modified live/attenuated and/or killed TGE. In still other embodiments, the immunogenic compositions further comprise one or more modified live/attenuated and/or killed PPRV. In yet other embodiments, the immunogenic compositions further comprise one or more modified live/attenuated and/or killed PPV. In still other embodiments, the immunogenic compositions further comprise one or more modified live/attenuated and/or killed PRV. In yet other embodiments, the immunogenic compositions further comprise one or more modified live/attenuated and/or killed PED. In still other embodiments, the immunogenic compositions further comprise one or more modified live/attenuated and/or killed serotypes of *Pasteurella multocida*. In yet other embodiments, the immunogenic compositions further comprise one or more modified live/attenuated and/or killed serotypes of *Salmonella* ssp. In still other embodiments, the immunogenic compositions further comprise one or more modified live/attenuated and/or killed serotypes of *Escherichia coli*. In yet other embodiments, the immunogenic compositions further comprise one or more modified live/attenuated and/or killed *Haemophilus parasuis*. In still other embodiments, the immunogenic compositions further comprise one or more modified live/attenuated and/or killed *Lawsonia intracellularis*. In yet other embodiments, the immunogenic compositions further comprise one or more modified live/attenuated and/or killed *Mycoplasma* ssp. (e.g., *Mycoplasma hyopneumoniae*). In still other embodiments, the immunogenic compositions further comprise one or more modified live/attenuated and/or killed *Bordetella bronchiseptica*. In yet other embodiments, the immunogenic compositions further comprise one or more modified live/attenuated and/or killed Erysipelas ssp. In still other embodiments, the immunogenic compositions further comprise one or more modified live/attenuated and/or killed *Campylobacter* ssp. In yet other embodiments, the immunogenic compositions further comprise one or more modified live/attenuated and/or killed *Actinobacillus pleuropneumoniae*. In still other embodiments, the immunogenic compositions further comprise one or more modified live/attenuated and/or killed *Clostridium perfringens*. In yet other embodiments, the immunogenic compositions further comprise one or more modified live/attenuated and/or killed *Clostridium difficile*.

In particular embodiments, a nucleic acid construct of the present invention encodes one or more NA antigens originating from IAV-S phylogenetic clusters, or antigenic fragments thereof. Accordingly, though alphavirus RNA replicon particles are specifically exemplified below, it should be understood that the present invention further includes other vectors and/or nucleic acid constructs.

Accordingly, in certain embodiments, the nucleic acid construct encodes an IAV-S NA that originates from a N1-classic phylogenetic cluster. In other embodiments, nucleic acid construct encodes an antigenic fragment of a NA that originates from a N1-classic phylogenetic cluster. In still other embodiments, the IAV-S NA originates from a N2-1998 phylogenetic cluster. In yet other embodiments, the alphavirus RNA replicon particle encodes an antigenic fragment of a NA that originates from a N2-1998 phylogenetic cluster. In still other embodiments, the IAV-S NA originates from a N1-pandemic phylogenetic cluster. In yet other embodiments, the alphavirus RNA replicon particle encodes an antigenic fragment of a NA that originates from a N1-pandemic phylogenetic cluster. In still other embodiments, the IAV-S NA originates from a N2-2002 phylogenetic cluster. In yet other embodiments, the nucleic acid construct encodes an antigenic fragment of a NA that originates from a N2-2002 phylogenetic cluster.

In an analogous embodiment, the IAV-S NA originates from a NA from a N1-pandemic (EU) lineage. In an analogous embodiment, the IAV-S NA originates from a NA from a N1-Eurasian Avian lineage. In an analogous embodiment, the IAV-S NA originates from a NA from a N2-Gent/1984 lineage. In another analogous embodiment, the IAV-S NA originates from a N2-Italy/2003 lineage. In still an analogous embodiment, the IAV-S NA originates from a N2-Scotland/1994 lineage. In certain embodiments of this type, the IAV-S NA originates from a N2-Scotland/1994 lineage (clade 1). In other embodiments of this type, the IAV-S NA originates from a N2-Scotland/1994 lineage (clade 2).

In particular embodiments, the IAV-S NA that originates from a N1-classic phylogenetic cluster comprises an amino acid sequence comprising 95% identity, 97% identity, 98% identity, or more with the amino acid sequence of SEQ ID NO: 2. In more specific embodiments of this type, the NA comprises the amino acid sequence of SEQ ID NO: 2. In other embodiments, the IAV-S NA that originates from a N1-pandemic phylogenetic cluster comprises an amino acid sequence comprising 95% identity, 97% identity, 98% identity, or more with the amino acid sequence of SEQ ID NO: 4. In more specific embodiments of this type, the NA comprises the amino acid sequence of SEQ ID NO: 4. In yet other embodiments, the IAV-S NA that originates from a N2-1998 phylogenetic cluster comprises an amino acid sequence comprising 92% identity, 94% identity, 97% identity, or more with the amino acid sequence of SEQ ID NO: 6. In more specific embodiments of this type, the NA comprises the amino acid sequence of SEQ ID NO: 6. In yet other embodiments, the IAV-S NA that originates from a N2-2002 phylogenetic cluster comprises an amino acid sequence comprising 92% identity, 94% identity, 97% identity, or more with the amino acid sequence of SEQ ID NO: 8. In more specific embodiments of this type, the NA comprises the amino acid sequence of SEQ ID NO: 8.

In particular embodiments, the IAV-S NA that originates from a N1-pandemic (EU) lineage comprises an amino acid sequence comprising 90% identity, 92% identity, 95% identity, or more with the amino acid sequence of SEQ ID NO: 12. In more specific embodiments of this type, the NA comprises the amino acid sequence of SEQ ID NO: 12. In other embodiments, the IAV-S NA that originates from a N1-Eurasian Avian lineage comprises an amino acid sequence comprising 85% identity, 90% identity, 95% identity, or more with the amino acid sequence of SEQ ID NO: 14. In more specific embodiments of this type, the NA comprises the amino acid sequence of SEQ ID NO: 14. In yet other embodiments, the IAV-S NA that originates from a N2-Gent/1984 lineage comprises an amino acid sequence comprising 90% identity, 92% identity, 95% identity, or more with the amino acid sequence of SEQ ID NO: 16. In more specific embodiments of this type, the NA comprises the amino acid sequence of SEQ ID NO: 16. In yet other embodiments, the IAV-S NA that originates from a N2-Italy/2003 lineage comprises an amino acid sequence comprising 90% identity, 92% identity, 95% identity or more with the amino acid sequence of SEQ ID NO: 18. In more specific embodiments of this type, the NA comprises the amino acid sequence of SEQ ID NO: 18. In other embodiments, the IAV-S NA that originates from a N2-Scotland/1994 (clade 1) lineage comprises an amino acid sequence comprising 90% identity, 92% identity, 95% identity or more with the amino acid sequence of SEQ ID NO: 20. In more specific embodiments of this type, the NA comprises the amino acid sequence of SEQ ID NO: 20. In yet other embodiments, the IAV-S NA that originates from a N2-Scotland/1994 (clade 2) lineage comprises an amino acid sequence comprising 90% identity, 92% identity, 95% identity or more with the amino acid sequence of SEQ ID NO: 22. In more specific embodiments of this type, the NA comprises the amino acid sequence of SEQ ID NO: 22.

The present invention provides nucleic acid constructs that encode two or more IAV-S antigens or antigenic fragments thereof. In specific embodiments, the nucleic acid constructs encode two to four or more NA antigens that originate from IAV-S, or antigenic fragments thereof. In related embodiments, the nucleic acid constructs encode two to four or more NA antigens that originate from different IAV-S phylogenetic clusters, or antigenic fragments thereof. In certain embodiments, the nucleic acid constructs encodes a NA originating from a N1-classic phylogenetic cluster or antigenic fragment thereof and a NA originating from a N2-2002 phylogenetic cluster or an antigenic fragment thereof. In even more specific embodiments the nucleic acid constructs encode a NA originating from a N2-2002 phylogenetic cluster or antigenic fragment thereof, a NA originating from a N2-1998 phylogenetic cluster or an antigenic fragment thereof, a NA originating from a N1-pandemic phylogenetic cluster or an antigenic fragment thereof, and a NA originating from a N1-classic phylogenetic cluster or an antigenic fragment thereof.

In certain embodiments, the nucleic acid constructs encodes a NA originating from a N1-pandemic (EU) lineage or antigenic fragment thereof and a NA originating from a N1-Eurasian Avian lineage or an antigenic fragment thereof. In other embodiments the nucleic acid constructs encode a NA originating from a N2-Gent/1984 lineage or antigenic fragment thereof and a NA originating from a N2-Italy/2003 lineage or an antigenic fragment thereof. In still other embodiments the nucleic acid constructs encode a NA originating from a N2-Gent/1984 lineage or antigenic fragment thereof and a NA originating from a N2-Scotland/1994 (clade 1) lineage or an antigenic fragment thereof. In yet other embodiments the nucleic acid constructs encode a NA originating from a N2-Gent/1984 lineage or antigenic fragment thereof and a NA originating from a N2-Scotland/1994 (clade 2) lineage or an antigenic fragment thereof. In still other embodiments the nucleic acid constructs encode a NA originating from a N2-Italy/2003 lineage or an antigenic fragment thereof and a NA originating from a N2-Scotland/1994 (clade 1) lineage or an antigenic fragment thereof. In yet other embodiments the nucleic acid constructs encode a NA originating from a N2-Italy/2003 lineage or an antigenic fragment thereof and a NA originating from a N2-Scotland/1994 (clade 2) lineage or an antigenic fragment thereof. In still other embodiments, a NA originating from one of the European N1 lineages or an antigenic fragment thereof is encoded in the same nucleic acid construct as a NA originating from one of the European N2 lineages or an antigenic fragment thereof. Similarly, the present invention includes nucleic acid constructs encoding three, four, or more NAs, with each NA originating from a different European lineage. Furthermore, the present invention includes nucleic acid constructs encoding two, three, four, or more NAs, with each NA originating from a different European lineage and/or phylogenetic cluster.

Accordingly, the present invention also includes all of the alphavirus RNA replicon particles of the present invention, naked DNA vectors that comprise the nucleic acid constructs of the present invention, naked RNA vectors that comprise the nucleic acid constructs of the present invention, the nucleic acid constructs of the present invention including synthetic messenger RNA, and RNA replicons, as well as all of the immunogenic compositions and/or vaccines that comprise the nucleic acid constructs (e.g., synthetic messenger RNA, RNA replicons), the alphavirus RNA replicon particles, naked RNA vectors, and/or the naked DNA vectors of the present invention.

The present invention further comprises vaccines (multivalent) vaccines comprising the immunogenic compositions of the present invention. In particular embodiments, the vaccines are a nonadjuvanted vaccine. In other embodiments, the vaccines comprise an adjuvant. In particular embodiments, the adjuvant is a biodegradable oil. In specific embodiments of this type, the biodegradable oil is dl-α-tocopheryl acetate (vitamin E acetate). In other embodiments, the adjuvant comprises an oil-in-water emulsion with 2.5%-50% (v/v) mineral oil. In specific embodiments the adjuvant comprises an oil-in-water emulsion with 2.5% (v/v) mineral oil. In related embodiments, the adjuvant comprises is an oil-in-water emulsion with 5% (v/v) mineral oil. In other embodiments, the adjuvant comprises an oil-in-water emulsion with 12.5% (v/v) mineral oil. In still other embodiments, the adjuvant comprises an oil-in-water emulsion with 25% (v/v) mineral oil. In yet other embodiments, the adjuvant comprises an oil-in-water emulsion with 50% (v/v) mineral oil. In more specific embodiments the adjuvant comprises a mixture of a biodegradable oil with a mineral oil adjuvant. In specific embodiments, the biodegradable oil is dl-α-tocopheryl acetate and the mineral oil is a liquid paraffin. In more specific embodiments, the biodegradable oil is dl-α-tocopheryl acetate and the mineral oil is a light liquid paraffin.

In certain embodiments, the vaccine aids in the prevention of disease due to IAV-S. In related embodiments, antibodies are induced in a porcine subject when the porcine is immunized with the vaccine. In certain embodiments, the porcine subject is a sow. In related embodiments, the vaccine provides protective maternal antibodies to progeny of the vaccinated sow. In other embodiments, the porcine subject is a piglet. In particular embodiments of this type, the vaccine is administered to a piglet as early as 3 days of age. In specific embodiments, the vaccine is administered as a booster vaccine. In certain embodiments, the vaccine is administered as a single dose vaccine. In specific embodiments of this type, the vaccine is administered as a booster vaccine. In yet other embodiments, the vaccine is administered as a multi-dose vaccine. In specific embodiments of this type, the vaccine is administered as a two-dose vaccine.

The present invention also provides methods of immunizing a porcine (e.g., a sow or a piglet) against a porcine pathogen, e.g., IAV-S, comprising administering to the porcine an immunologically effective amount of a vaccine or multivalent of the present invention. In particular embodiments, the vaccine is administered via intramuscular injection. In alternative embodiments, the vaccine is administered via subcutaneous injection. In other embodiments, the vaccine is administered via intravenous injection. In still other embodiments, the vaccine is administered via intradermal injection. In yet other embodiments, the vaccine is administered via oral administration. In still other embodiments, the vaccine is administered via intranasal administration.

Accordingly, the vaccines and multivalent vaccines of the present invention can be administered as a primer vaccine and/or as a booster vaccine. In specific embodiments, a vaccine of the present invention is administered as a one shot vaccine (one dose), without requiring subsequent administrations. In certain embodiments, in the case of the administration of both a primer vaccine and a booster vaccine, the primer vaccine and the booster vaccine can be administered by the identical route. In certain embodiments of this type, the primer vaccine and the booster vaccine are both administered by intradermal injection. In other embodiments of this type, the primer vaccine and the booster vaccine are both administered by intramuscular injection. In alternative embodiments, in the case of the administration of both a primer vaccine and a booster vaccine, the administration of the primer vaccine can be performed by one route and the booster vaccine by another route. In certain embodiments of this type, the primer vaccine can be administered by intradermal injection and the booster vaccine can be administered orally. In related embodiments of this type, the primer vaccine can be administered by intramuscular injection and the booster vaccine can be administered orally. In other embodiments of this type, the primer vaccine can be administered by intramuscular injection and the booster vaccine can be administered by intradermal injection. In still other embodiments of this type, the primer vaccine can be administered by intradermal injection and the booster vaccine can be administered by intramuscular injection.

The invention further provides for a method of immunizing a porcine (e.g., a sow or a piglet) against IAV-S comprising injecting the porcine with an immunologically effective amount of the above described inventive vaccines. In particular embodiments, the vaccines can include from about $1 \times 10^4$ to about $1 \times 10^{10}$ RPs or higher, for example. In more particular embodiments, the vaccines can include from about $1 \times 10^5$ to about $1 \times 10^9$ RPs. In even more particular embodiments, the vaccines can include from about $1 \times 10^6$ to about $1 \times 10^8$ RPs.

In particular embodiments, the vaccines of the present invention are administered in 0.05 mL to 3 mL doses. In more particular embodiments, the dose administered is 0.1 mL to 2 mL. In still more particular embodiments, the dose administered is 0.2 mL to 1.5 mL. In even more particular embodiments, the dose administered is 0.3 to 1.0 mL. In still more particular embodiments, the dose administered is 0.4 mL to 0.8 mL.

These and other aspects of the present invention will be better appreciated by reference to the following Figures and the Detailed Description.

DETAILED DESCRIPTION OF THE INVENTION

Figure 1A:
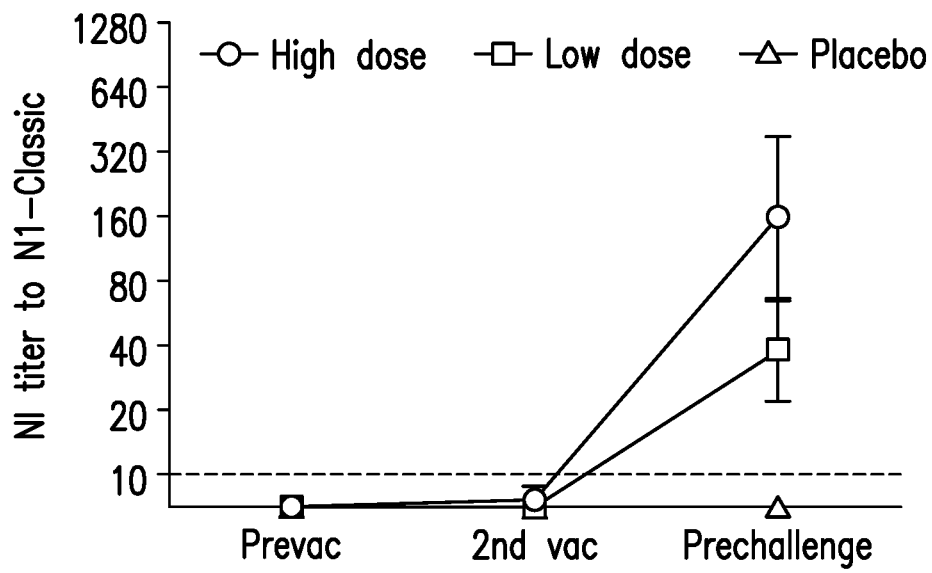
FIGS. 1A-1D show the serum neuraminidase inhibiting (NI) antibody responses specific to all four NA strains of the vaccine compositions described in Example 1 below. Serum samples were collected prior to first vaccination (3 weeks of age), prior to second vaccination (6 weeks of age), and prior to challenge (9 weeks of age).
Figure 1B:
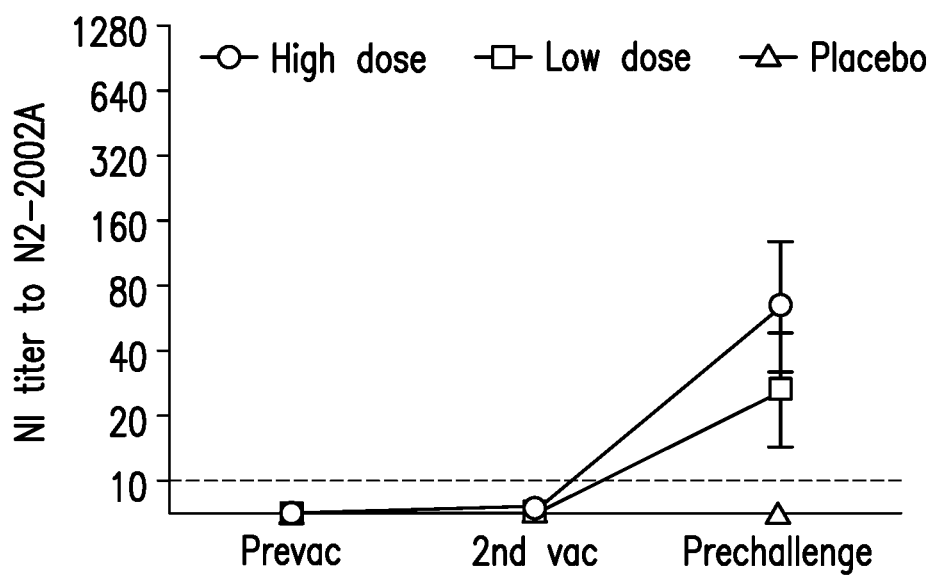
Figure 1C:
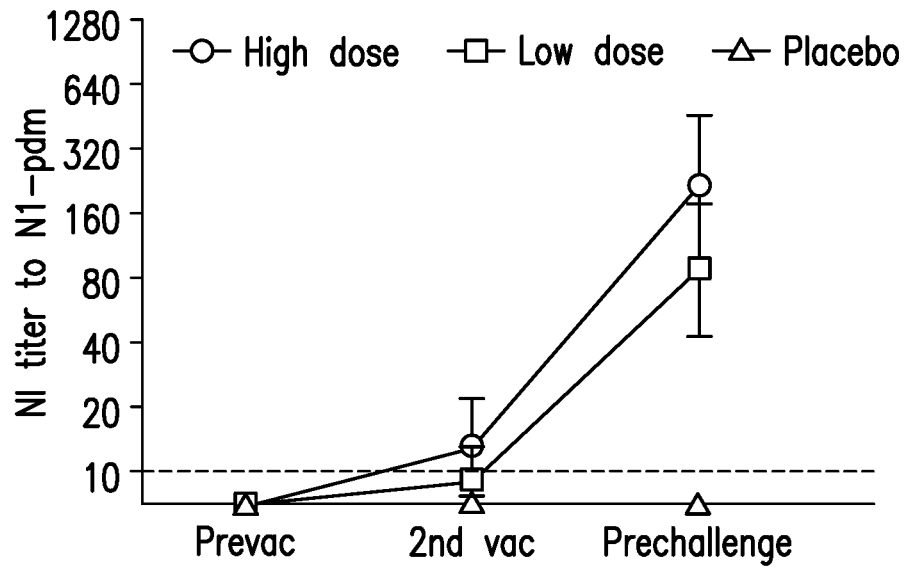
Figure 1D:
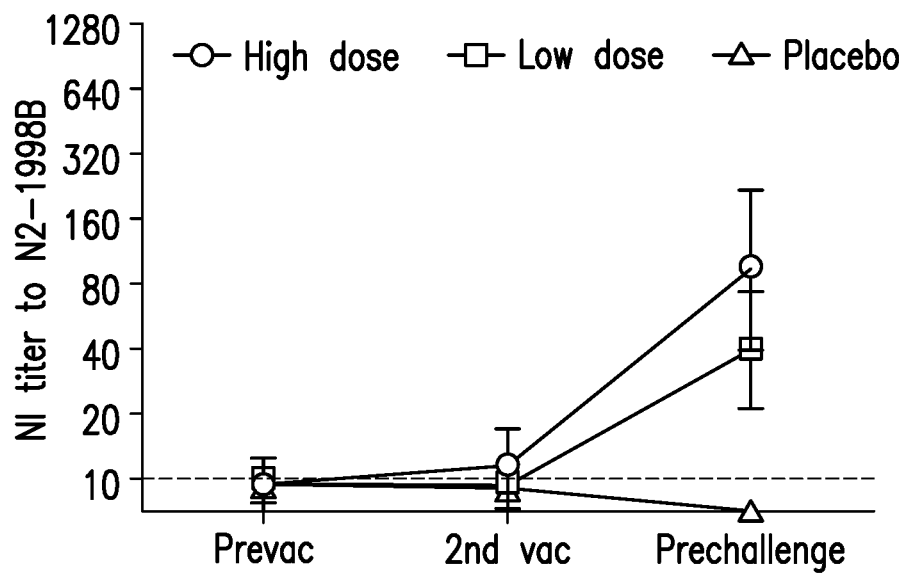

The present invention provides vaccines and immunogenic compositions that include an immunologically effective amount of one or more alphavirus RNA replicon particles that encode one or more neuraminidases (NAs) from one or more influenza A virus serotypes. In one aspect of the present invention, the vaccines and immunogenic compositions neither comprise a hemagglutinin (HA) or an antigenic fragment thereof, nor a nucleotide sequence that encodes the HA or the antigenic fragment thereof. One advantage of an influenza A virus vaccine based on multiple NAs, and the absence of a HA, is that NAs are affected less by antigenic drift than the HAs, which enables the corresponding vaccines to comprise antigens from fewer influenza isolates. This saves production costs, as well as extends the time period required to update a given influenza vaccine. In addition, because currently marketed influenza A virus vaccines are based on inactivated influenza viruses, which generate much higher titers of HA antibodies than NA antibodies in the animal subject, the negative effect of maternal antibodies on the immunization of progeny of the animal subject should be significantly diminished for a NA based vaccine.

In one important aspect of the present invention, vaccines and immunogenic compositions are provided that include an immunologically effective amount of one or more alphavirus RNA replicon particles that encode one or more neuraminidases (NAs) from one or more Swine Influenza A virus (IAV-S) phylogenetic clusters and/or lineage. In one aspect of the present invention, the vaccines and immunogenic compositions neither comprise an IAV-S hemagglutinin (HA) or an antigenic fragment thereof, nor a nucleotide sequence that encodes the IAV-S HA or the antigenic fragment thereof.

As indicated above, an IAV-S vaccine based on multiple NAs, and the absence of an HA, enables the corresponding vaccines to comprise antigens from fewer IAV-S isolates. This saves production costs, as well as extends the time period required to update a given IAV-S vaccine. In addition, because currently marketed IAV-S vaccines are based on inactivated influenza viruses, which generate much higher titers of HA antibodies than NA antibodies in the animal subject, the negative effect of maternal antibodies on the immunization of piglets should be significantly diminished for a neuraminidase based vaccine.

In order to more fully appreciate the invention, the following definitions are provided.

The use of singular terms for convenience in description is in no way intended to be so limiting. Thus, for example, reference to a composition comprising "a polypeptide" includes reference to one or more of such polypeptides. In addition, reference to an "alphavirus RNA replicon particle" includes reference to a plurality of such alphavirus RNA replicon particles, unless otherwise indicated.

As used herein the term "approximately" is used interchangeably with the term "about" and signifies that a value is within fifty percent of the indicated value i.e., a composition containing "approximately" $1 \times 10^8$ alphavirus RNA replicon particles per milliliter contains from $5 \times 10^7$ to $1.5 \times 10^8$ alphavirus RNA replicon particles per milliliter.

As used herein, the term "pig" or "swine" or "porcine" are used interchangeably and include all domesticated porcine species, unless otherwise indicated.

As used herein, a "phylogenetic cluster" is a set of influenza virus neuraminidases that have been grouped together (on the same branch) in a phylogenetic tree or evolutionary tree that is rooted back to a similar (homologous) ancestor (see, Examples 5). For the IAV-S neuraminidases (NAs) found in the U.S., there are two predominant phylogenetic clusters of N1, N1-classic and N1-pandemic, and two predominant phylogenetic clusters of N2, N2-1998 and N2-2002. The N1 classic phylogenetic cluster contains the NAs grouped together with the NA from the H1N1 classic swine influenza virus. The N1 pandemic phylogenetic cluster contains the NAs grouped together with the NA that comes from the H1N1 pandemic influenza virus. The N2-1998 phylogenetic cluster contains the NAs grouped together with the NA from the human H3N2 influenza virus that jumped into pigs in 1998, whereas the N2-2002 phylogenetic cluster contains the NAs grouped together with the NA from the human H3N2 influenza virus that jumped into pigs in 2002. [See, Anderson et al., *Influenza and other Respiratory Viruses* 7 (Suppl. 4): 42-51 (2013)]. Example 5 provides the methodology for making the phylogenetic cluster determination. For the U.S. IAV-S NA phylogenetic clusters N1-classic N1-pandemic N2-1998, N2-2002, the corresponding representative neuraminidases have the following respective amino acid sequences SEQ ID NO: 2, SEQ ID NO: 4, SEQ ID NO: 6, and SEQ ID NO: 8.

As used herein, a "lineage" is a set of influenza virus neuraminidases that have been grouped together (on the same branch) in an evolutionary tree that is rooted back to a similar (homologous) ancestor (see, Example 6 below). These groupings have been made for European neuraminidases and are analogous to the phylogenetic clusters for U.S. viruses, but are not equivalent. Lineage determinations can be obtained with readily available software, i.e., MEGA X, as described in Example 6 below. For the EU IAV-S NA lineages of N1-pandemic (EU), N1-Eurasian Avian, N2-Gent/1984, N2-Italy/4675/2003, N2-Scotland/1994 clade 1, or N2-Scotland/1994 clade 2, the corresponding representative neuraminidases have the following respective amino acid sequences SEQ ID NO: 12, SEQ ID NO: 14, SEQ ID NO: 16, SEQ ID NO: 18, SEQ ID NO: 20, and 22.

As used herein, the term "replicon" refers to a modified RNA viral genome that lacks one or more elements (e.g., coding sequences for structural proteins) that if they were present, would enable the successful propagation of the parental virus in cell cultures or animal hosts. In suitable cellular contexts, the replicon will amplify itself and may produce one or more sub-genomic RNA species.

As used herein, the term "alphavirus RNA replicon particle", abbreviated "RP", is an alphavirus-derived RNA replicon packaged in structural proteins, e.g., the capsid and glycoproteins, which also are derived from an alphavirus, e.g., as described by Pushko et al., [Virology 239(2):389-401 (1997)]. An RP cannot propagate in cell cultures or animal hosts (without a helper plasmid or analogous component), because the replicon does not encode the alphavirus structural components (e.g., capsid and glycoproteins).

The term "non-IAV-S", is used to modify terms such as pathogen, and/or antigen (or immunogen) to signify that the respective pathogen, and/or antigen (or immunogen) is neither an IAV-S pathogen nor an IAV-S antigen (or immunogen) and that a non-IAV-S protein antigen (or immunogen) does not originate from an IAV-S.

The terms "originate from", "originates from" and "originating from" are used interchangeably with respect to a given protein antigen and the pathogen or strain of that pathogen that naturally encodes it, and as used herein signify that the unmodified and/or truncated amino acid sequence of that given protein antigen is encoded by that pathogen or strain of that pathogen. The coding sequence, within a nucleic acid construct of the present invention for a protein antigen originating from a pathogen may have been genetically manipulated so as to result in a modification and/or truncation of the amino acid sequence of the expressed protein antigen relative to the corresponding sequence of that protein antigen in the pathogen or strain of pathogen (including naturally attenuated strains) it originates from.

As used herein, the terms "protecting", or "providing protection to", or "eliciting protective immunity to", "aids in prevention of disease", and "aids in the protection" do not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

As used herein, a "vaccine" is a composition that is suitable for application to an animal, e.g., porcine (including, in certain embodiments, humans, while in other embodiments being specifically not for humans) comprising one or more antigens typically combined with a pharmaceutically acceptable carrier such as a liquid containing water, which upon administration to the animal induces an immune response strong enough to minimally aid in the protection from a disease arising from an infection with a wild-type micro-organism, i.e., strong enough for aiding in the prevention of the disease, and/or preventing, ameliorating or curing the disease.

As used herein, a multivalent vaccine is a vaccine that comprises two or more different antigens. In a particular embodiment of this type, the multivalent vaccine stimulates the immune system of the recipient against two or more different pathogens.

The terms "adjuvant" and "immune stimulant" are used interchangeably herein, and are defined as one or more substances that cause stimulation of the immune system. In this context, an adjuvant is used to enhance an immune response to one or more vaccine antigens/isolates. Accordingly, "adjuvants" are agents that nonspecifically increase an immune response to a particular antigen, thus reducing the quantity of antigen necessary in any given vaccine, and/or the frequency of injection necessary in order to generate an adequate immune response to the antigen of interest. In this context, an adjuvant is used to enhance an immune response to one or more vaccine antigens/isolates.

As used herein, a "nonadjuvanted vaccine" is a vaccine or a multivalent vaccine that does not contain an adjuvant.

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient animal, e.g., porcine.

"Parenteral administration" includes subcutaneous injections, submucosal injections, intravenous injections, intramuscular injections, intradermal injections, and infusion.

As used herein the term "antigenic fragment" in regard to a particular protein (e.g., a protein antigen) is a fragment of that protein that is antigenic, i.e., capable of specifically interacting with an antigen recognition molecule of the immune system, such as an immunoglobulin (antibody) or T cell antigen receptor. For example, an antigenic fragment of an IAV-S neuraminidase (NA) is a fragment of the NA protein that is antigenic. Preferably, an antigenic fragment of the present invention is immunodominant for antibody and/or T cell receptor recognition. In particular embodiments, an antigenic fragment with respect to a given protein antigen is a fragment of that protein that retains at least 25% of the antigenicity of the full length protein. In preferred embodiments an antigenic fragment retains at least 50% of the antigenicity of the full length protein. In more preferred embodiments, an antigenic fragment retains at least 75% of the antigenicity of the full length protein. Antigenic fragments can be as small as 20 amino acids or at the other extreme, be large fragments that are missing as little as a single amino acid from the full-length protein. In particular embodiments the antigenic fragment comprises 25 to 150 amino acid residues. In other embodiments, the antigenic fragment comprises 50 to 250 amino acid residues.

As used herein one amino acid sequence is 100% "identical" or has 100% "identity" to a second amino acid sequence when the amino acid residues of both sequences are identical. Accordingly, an amino acid sequence is 50% "identical" to a second amino acid sequence when 50% of the amino acid residues of the two amino acid sequences are identical. The sequence comparison is performed over a contiguous block of amino acid residues comprised by a given protein, e.g., a protein, or a portion of the polypeptide being compared. In a particular embodiment, selected deletions or insertions that could otherwise alter the correspondence between the two amino acid sequences are taken into account.

As used herein, nucleotide and amino acid sequence percent identity can be determined using C, MacVector (MacVector, Inc. Cary, NC 27519), Vector NTI (Informax, Inc. MD), Oxford Molecular Group PLC (1996) and the Clustal W algorithm with the alignment default parameters, and default parameters for identity. These commercially available programs can also be used to determine sequence similarity using the same or analogous default parameters. Alternatively, an Advanced Blast search under the default filter conditions can be used, e.g., using the GCG (Genetics Computer Group, Program Manual for the GCG Package, Version 7, Madison, Wisconsin) pileup program using the default parameters.

As used herein, the term "inactivated" microorganism is used interchangeably with the term "killed" microorganism. For the purposes of this invention, an "inactivated" microorganism is an organism which is capable of eliciting an immune response in an animal, but is not capable of infecting the animal. An antigen of the present invention (e.g., an inactivated *Mycoplasma hyopneumoniae*) may be inactivated by an agent selected from the group consisting of binary ethyleneimine, formalin, beta-propiolactone, thimerosal, or heat. In a particular embodiment, inactivated *Mycoplasma hyopneumoniae* isolates combined with an RP of the present invention are inactivated by binary ethyleneimine.

The present invention also provides vaccines against multiple porcine pathogens. For example, the coding sequence of a protein antigen or antigenic fragment thereof, or combination of such coding sequences of protein antigens useful in a porcine vaccine can be added to an alphavirus RNA replicon particle (RP) and/or combined in the same RP as one that encodes a NA originating from an IAV-S in the vaccine. Examples of pathogens that one or more of protein antigens or antigenic fragments thereof can originate from include porcine reproductive and respiratory syndrome virus (PRRS), porcine circovirus (PCV), transmissible gastroenteritis virus (TGE), porcine pseudorabies virus (PPRV), porcine parvovirus (PPV), porcine rotavirus (PRV), porcine epidemic diarrhea virus (PED), *Pasteurella multocida* of multiple serotypes, *Salmonella* ssp., *Escherichia coli*, e.g., (serotypes K99, K88, 987P, or F41), *Haemophilus parasuis, Lawsonia intracellularis, Mycoplasma* ssp. (e.g., *Mycoplasma hyopneumoniae*), *Bordetella bronchiseptica, Erysipelas* ssp., *Campylobacter* ssp., *Actinobacillus pleuropneumoniae, Clostridium perfringens*, and *Clostridium difficile*.

In addition, the present invention provides vaccines comprising one or more RPs of the present invention in combination with one or more other vectors encoding one or more of these porcine antigens (e.g., a baculovirus vector encoding an ORF-2 protein from a porcine circovirus-2, (PCV-2) and/or porcine circovirus-3 (PCV-3) and/or inactivated toxoids originating from one or more of these porcine pathogens. Moreover, such vaccines can include any alphavirus RNA replicon particle that encodes a NA originating from an IAV-S in a vaccine of the present invention together with one or more killed and/or modified (attenuated) live porcine virus isolates and/or porcine bacteria. All such multivalent vaccines are included in the present invention.

Accordingly, one or more alphavirus RNA replicon particles (RPs) that encode one or more NAs originating from IAV-S can be added together with one or more other vectors encoding one or more porcine antigen and/or one or more killed and/or modified (attenuated) live virus isolates such as one or more killed or modified live IAS-V strain, one or more killed and/or modified live PRRS virus, one or more killed and/or modified live PCV, one or more killed, and/or modified live TGE, one or more killed and/or modified live PPRV, one or more killed and/or modified live PPV, one or more killed and/or modified live PRV and one or more killed and/or modified live PED. Moreover, one or more alphavirus RNA replicon particles (RPs) that encode one or more NAs originating from IAV-S can be added together with one or more other vectors encoding one or more porcine antigen and/or added together with one or more killed and/or modified (attenuated) live bacteria that can infect swine too, including one or more killed and/or modified live *Pasteurella multocida* (of one or more multiple serotypes), *Salmonella* ssp., *Escherichia coli* (of one or more multiple serotypes), *Haemophilus parasuis, Lawsonia intracellularis, Mycoplasma* ssp. (e.g., *Mycoplasma hyopneumoniae*), *Bordetella bronchiseptica*, Erysipelas ssp., *Campylobacter* ssp., *Actinobacillus pleuropneumoniae, Clostridium perfringens*, and *Clostridium difficile*.

The alphavirus RNA replicon particles of the present invention may be lyophilized and rehydrated with a sterile water diluent. On the other hand, when the alphavirus RNA replicon particles are stored separately, but intended to be mixed with other vaccine components prior to administration, the alphavirus RNA replicon particles can be stored in the stabilizing solution of those components, e.g., a high sucrose solution.

In one aspect, a vaccine of the present invention can comprises an adjuvant. In certain embodiments, the adjuvant is a biodegradable oil. In specific formulations, the biodegradable oil is dl-α-tocopheryl acetate (vitamin E acetate). In other formulations the adjuvant comprises an oil-in-water emulsion comprising 2.5% to 50% (v/v) mineral oil. In more specific formulations, the adjuvant comprises is an oil-in-water emulsion which comprises 5% to 25% mineral oil. In related formulations, the adjuvant is a mixture of two components. The first component consists of mineral oil droplets with an approximate average (volume weighed)

size around 1 µm, which is stabilized with polysorbate 80 (polyoxyethylene (20) sorbitan monooleate) in water. The first component can comprise 25 weight percent of the mineral oil and 1 weight percent of the polysorbate 80, with the remainder water. The second component can consist of droplets of biodegradable dl-α-tocopheryl acetate with an approximate average (volume weighed) size of 400 nm, which is also stabilized with polysorbate 80. Particular formulations comprise 15 weight percent of dl-α-tocopheryl acetate and 6 weight percent of polysorbate 80, with the remainder water. In particular embodiments, the adjuvant is X-SOLVE™ (which is a combination of two component adjuvants: DILUVAC FORTE' which is based on dl-α-tocopheryl acetate and MICROSOL™, which is based on light liquid paraffin [see e.g., U.S. Pat. No. 8,597,662]. In related formulations, the adjuvant contains oil droplets of sub-micrometer size and droplets of biodegradable oil, with the droplets of the biodegradable oil having an average size that differs from the average size of the droplets of mineral oil [see e.g., U.S. Pat. No. 9,084,768].

A vaccine of the present invention can be readily administered by any standard route including intravenous, intramuscular, subcutaneous, oral, intranasal, intradermal, and/or intraperitoneal vaccination. The skilled artisan will appreciate that the vaccine composition is preferably formulated appropriately for each type of recipient animal and route of administration.

Thus, the present invention also provides methods of immunizing a porcine against IAV-S and/or other porcine pathogens. One such method comprises injecting a porcine with an immunologically effective amount of a vaccine of the present invention, so that the porcine produces appropriate IAV-S antibodies.

It is also to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting, since the scope of the present invention will be limited only by the appended claims and equivalents thereof.

SEQUENCE TABLE[1]

| SEQ ID NO: | Description | Type |
|---|---|---|
| 1 | N1-classic (codon optimized) | nucleic acid |
| 2 | N1-classic | amino acid |
| 3 | N1-pandemic (codon optimized) | nucleic acid |
| 4 | N1-pandemic | amino acid |
| 5 | N2-1998 (codon optimized) | nucleic acid |
| 6 | N2-1998 | amino acid |
| 7 | N2-2002 (codon optimized) | nucleic acid |
| 8 | N2-2002 | amino acid |
| 9 | ggcgcgccgcacc | nucleic acid |
| 10 | ttaattaa | nucleic acid |
| 11 | N1-pandemic (EU) | nucleic acid |
| 12 | N1-pandemic (EU) | amino acid |
| 13 | N1-Eurasian Avian | nucleic acid |
| 14 | N1-Eurasian Avian | amino acid |
| 15 | N2-Gent/1984 | nucleic acid |
| 16 | N2-Gent/1984 | amino acid |
| 17 | N2-Italy/4675/2003 | nucleic acid |
| 18 | N2-Italy/4675/2003 | amino acid |
| 19 | N2-Scotland/1994 (clade 1) | nucleic acid |
| 20 | N2-Scotland/1994 (clade 1) | amino acid |
| 21 | N2-Scotland/1994 (clade 2) | nucleic acid |
| 22 | N2-Scotland/1994 (clade 2) | amino acid |
| 23 | N1-pandemic (EU) (codon optimized) | nucleic acid |
| 24 | N2-Gent/1984 (codon optimized) | nucleic acid |
| 25 | N2-Italy/4675/2003 (codon optimized) | nucleic acid |
| 26 | N2-Scotland/1994 (clade 1) (codon optimized) | nucleic acid |
| 27 | N2-Scotland/1994 (clade 2) (codon optimized) | nucleic acid |

[1]The nucleotide sequences are provided as DNA sequences only, though it should be understood that when the sequence is included in an RNA construct, it is the corresponding RNA sequence (with uracil, "u" replacing thymidine, "t") that is intended.

```
SEQUENCES
N1-classic
                                                   (SEQ ID NO: 1)
atgaatactaatcaaaggatcattaccattgggacagtctgcatgattgtcggtatcatctctcttt tgcttcagattggaaacattgtctcactttggattagccattcaattcagaccggatgggagaatca cactgagatgtgcaatcaaagtgtcattacttatgtcaataacacttgggtgaaccggacttatgtg aacattagcaatatcaagattgcaactattcaagatgtgactagtatcattttggccggaaattcta gtctttgcccggtgtcagggtgggctgtctacagcaaagacaatagcattaggattggatcaaaagg ggacattttcgtcattagagagcctttcatctcatgctcacaattggagtgccggaccttctttctg acccaaggggcattgctgaatgacaaacattcaaatggtaccgtcaaggacaggagtccttatagaa ccctgatgagctgccctatcggtgaggcccctttcgccatacaactcacggttcgaatctgtcgcatg gtcagcatctgcttgtcatgatggaatgggatggcttacaatcgggatcagtggaccggataatggt gctgtcgcagtcttgaaatacaacggaatcattacagatacaatcaaatcttggaggaacaagattc ttagaactcaagaatcagagtgtgtctgtatgaacggatcatgttttacagtcttgacagatggccc aagcaatggacaagcctcttacaaaatctttaaggtggaaaaaggaaagattatcaagtcgattgag ctggatgccccaattaccactatgaagaatgctcttgttatccagatactggcaaagtcatgtgtg
```

-continued

```
tctgccgggacaattggcacgcctcaaaccggccatgggtgtcgttcaatcagaatcttgactatca aattggatacatttgctctggagtctttggtgataaccctagatccaatgatgggaagggcaattgt ggcccggtcctttctaatggagcaaatggagtgaaaggtttctcatatcggtatggaaatggtgtgt ggattggtcggaccaagtcaatcaactctcggtcggttttgagatgatttgggatccgaatggatg gactgagacagattcatcattctcgatgaagcaggacattatcgctcttaatgattggtctggatac tcgggatcttttgtccaacatccggagcttactggtatgaattgcattaggccttgtttctgggtgg aattgatcagagggcaacccaaggaaagcactatctgggctagcggttccagcatctcattctgtgg cgtcaattcggaaaccgcttcctggtcttggccagacggagctgatctgccattccattgacaag
```

N1-classic (SEQ ID NO: 2)

MNTNQRIITIGTVCMIVGIISLLLQIGNIVSLWISHSIQTGWENHTEMCNQSVITYVNNT

WVNRTYVNISNIKIATIQDVTSIILAGNSSLCPVSGWAVYSKDNSIRIGSKGDIFVIREP

FISCSQLECRTFFLTQGALLNDKHSNGTVKDRSPYRTLMSCPIGEAPSPYNSRFESVAWS

ASACHDGMGWLTIGISGPDNGAVAVLKYNGIITDTIKSWRNKILRTQESECVCMNGSCFT

VLTDGPSNGQASYKIFKVEKGKIIKSIELDAPNYHYEECSCYPDTGKVMCVCRDNWHASN

RPWVSFNQNLDYQIGYICSGVFGDNPRSNDGKGNCGPVLSNGANGVKGFSYRYGNGVWIG

RTKSINSRSGFEMIWDPNGWTETDSSFSMKQDIIALNDWSGYSGSFVQHPELTGMNCIRP

CFWVELIRGQPKESTIWASGSSISFCGVNSETASWSWPDGADLPFTIDK

N1-pandemic (SEQ ID NO: 3)

```
atgaatcctaaccaaaagatcattaccattggttcggtctgtatgacaattggaatggctaacctga tccttcaaattggaaacattatctcaatctgggtcagccactcaattcaaattggaaatcaatcgca gattgaaacatgcaaccaaagcgtcattacttacgaaaacaacacttgggtgaaccagacctacgtg aacatcagcaacaccaacttcgctgctggacagtccgtggtttccgtgaaactggcgggcaactcct ctctctgccctgtgagcggatgggctatctactccaaagacaactcagtcagaatcggttccaaggg ggatgtgtttgtcataagggaaccattcatctcatgctctcccttgaatgcagaaccttcttcttg actcaaggggccttgctaaatgacaaacattccaacggaaccattaaagacaggagcccatatcgga ccctgatgagctgtcctatcggtgaagtcccctcgccatacaactcaagatttgagtcagtcgcttg gtcagcatccgcttgtcatgatggcatcaattggctcaccattggaatttctggcccagacagtggg gcagtggctgtgctgaagtacaatggcattataacagacactatcaagtcgtggaggaacaacatat tgagaactcaagagtctgaatgtgcatgtgtgaatggttcttgctttaccatcatgaccgatggacc atccgatggacaggcctcctacaagatcttcagaatcgaaaagggaaagatcgtcaaatcagtcgaa atgaatgcccctaactaccactatgaggaatgctcctgttatcctgattcctccgaaatcacgtgcg tgtgcagggataactggcatggctccaatcggccgtgggtgtctttcaaccagaatctggaatatca gatcggatacatttgctccggggtgttcggagacaatccgcgccctaatgataagacaggctcgtgt ggtccagtctcgtctaacggagccaacggagtcaaaggattttcattcaaatacggcaatggagtgt ggataggaagaactaagagcatttcctcaagaaaaggtttcgagatgatttgggatccgaatggatg gactgggactgacaacaagttctcaatcaagcaagacatcgtgggaatcagcgagtggtcaggatat agcgggtcctttgtgcagcaccccgaactgaccgggctggattgtattagaccttgcttctgggtcg
```

-continued aactcatcagagggcgacccgaagagaacacaatctggactagcgggagcagcatctccttttgtgg tgtgaactcggacactgtgggttggtcttggccagacggtgctgagttgccttttaccattgacaag N1-pandemic (SEQ ID NO: 4)

MNPNQKIITIGSVCMTIGMANLILQIGNIISIWVSHSIQIGNQSQIETCNQSVITYENNT

WVNQTYVNISNTNFAAGQSVVSVKLAGNSSLCPVSGWAIYSKDNSVRIGSKGDVFVIREP

FISCSPLECRTFFLTQGALLNDKHSNGTIKDRSPYRTLMSCPIGEVPSPYNSRFESVAWS

ASACHDGINWLTIGISGPDSGAVAVLKYNGIITDTIKSWRNNILRTQESECACVNGSCFT

IMTDGPSDGQASYKIFRIEKGKIVKSVEMNAPNYHYEECSCYPDSSEITCVCRDNWHGSN

RPWVSFNQNLEYQIGYICSGVFGDNPRPNDKTGSCGPVSSNGANGVKGFSFKYGNGVWIG

RTKSISSRKGFEMIWDPNGWTGTDNKFSIKQDIVGISEWSGYSGSFVQHPELTGLDCIRP

CFWVELIRGRPEENTIWTSGSSISFCGVNSDTVGWSWPDGAELPFTIDK

N2-1998A (SEQ ID NO: 5)

atgaatccaaaccaaaagataatcacaattggctctgtttctctcactattgccacaatgtgcctcc ttatgcaaattgccatcctgattactaatgtcacattgcactccaatcagtacgaatgcaactaccc cccaaacaaccaagtgatactgtgtgaaccaactatcatcaaaagaaacattactgagattgtgtat ctggccaacaccaccatagagaaggaaatctgccccaagctggcagaatacagaaactggtcgaagc cgcaatgtaaaattacagggtttgcaccttttccaaggacaattcgattaggctttctgcgggtgg cgacatttgggtaacgagagaaccttatgtgtcatgcgatcctgataagtgttaccagtttgccctt ggacaaggaacaacgctcaacaacagacattcaaacgacaccgtgcatgataggacccccttatcgaa ccctattgatgaatgagttgggtattccattccatttggggaccaaacaagtgtgcatcgcatggtc cagctcatcctgccatgatggacgggcttggcttcatgtctgtattactgggcatgacaacaatgca actgccagcatcatttacaatggacgccttgtcgatagtattggttcatggtccaaaagaatcctca ggacccaggagtcggaatgcgtgtgcatcaatggaacttgtaccgtggtcatgactgatgggtccgc ttcaggaatagctgacactaaaatcctgttcattgaagaggggaaaatcgtgcacattagcccactg ctggggtccgctcagcacgtggaggagtgctcctgctatccccgataccaggtgtcagatgcatct gtagagacaactggaaaggctccaacagacctgtcgtggatattaatgtgaaggattatagcattgt gtcctcctacgtgtgctccggactggtgggagacacccccagaaaagacgacagatccagctccagc aattgtctgaatcctaacaacgagaaggggagcatggagtgaaaggctgggcctttgatgatggaa atgacgtgtggatggggaggacaatcaacgagacattacgctcaggttatgaaaccttcaaagtcat tgaaggctggtccaaacctaattccaaattgcagataaatcgccaagtcattgttgaaagagatgat aggtccggttattctggaattttctctgtcgaaggaaagagctgtatcaatcggtgtttttacgtgg agctgatcagaggaaggaaacaggaaactgcagtgtggtggacgtcaaattccattgtggtgttttg tggcacctcaggtacctatggaaccggctcatggcctgatgggcggacatcaatctcatgcctgtg

N2-1998A (SEQ ID NO: 6)

MNPNQKIITIGSVSLTIATMCLLMQIAILITNVTLHSNQYECNYPPNNQVILCEPTIIKR

NITEIVYLANTTIEKEICPKLAEYRNWSKPQCKITGFAPFSKDNSIRLSAGGDIWVTREP

YVSCDPDKCYQFALGQGTTLNNRHSNDTVHDRTPYRTLLMNELGIPFHLGTKQVCIAWSS

SSCHDGRAWLHVCITGHDNNATASIIYNGRLVDSIGSWSKRILRTQESECVCINGTCTVV

MTDGSASGIADTKILFIEEGKIVHISPLLGSAQHVEECSCYPRYPGVRCICRDNWKGSNR

PVVDINVKDYSIVSSYVCSGLVGDTPRKDDRSSSSNCLNPNNEKGEHGVKGWAFDDGNDV

-continued

WMGRTINETLRSGYETFKVIEGWSKPNSKLQINRQVIVERDDRSGYSGIFSVEGKSCINR

CFYVELIRGRKQETAVWWTSNSIVVFCGTSGTYGTGSWPDGADINLMPV

N2-2002A (SEQ ID NO: 7)
atgaatccaaatcaaaagatcattactattggatcagtctcactcatcattgccacaatttgtttcc ttatgcaaattgcaatccttgtcactactgtcacattgcatttcaagcagcatgactacaactcccc cccaaacaaccaagctactctgtgtgaaccaacaatcattgacggaaaacaactgaaattgtgtat cttactaacaccaccattgagaaagaagtctgccccaaacttgcagagtaccggaactggtcaaagc ctcaatgtaacattactggatttgcaccattttcgaaagacaattctattcggttgtctgctggtgg ggacatctgggtgactagggaaccttatgtgtcatgcgatcctgacaagtgttaccaatttgcccctt ggacagggtacaactcttaacaacggacattcgaataacacagtccatgataggaccccgtatcgga cccttcttatgaatgagcttggtgtcccttttcatcttggaaccagacaagtgtgcatggcttggtc tagctcatcttgtcacgatgggaaagcatggctgcatgtctgtgtcactggaaatgataacaatgct actgctagcttcatctacaatggtaggcttgtggattctattggttcgtggtcgaaaaacattctcc ggacccaagagtcagaatgcgtctgtatcaatggaacatgtactgtcgtcatgactgatggatccgc tagtggaaaagcagataccaaaatcttgttcgtcgaagaggggaagatcgtccatatcagcactctg ttgggatctgcacagcacgtcgaggaatgctcctgttatcctaggtttccgggagtccggtgtgtct gccgggacaactggaaaggatctaatagacccatcgtcgacatcaatgtcaagaattacagcattgt ctcttcgtatgtctgcagtggacttgtcggtgatactcccagagagagcgactcagtctcctcatct tattgcttggatccgaacaatgagaagggtggtcatgggtgaaagggtgggcctttgatgatggta atgacgtgtggatgggaagaacaatcaacgagactttgcgcttgggatatgaaaccttcaaagtcat tgaaggctggtccacagctaactccaagtcacagacaaatagacaagtgattgtcgaaaaaggagac aggtcaggatattctgggattttctcagtcgagggaaagaactgcatcaataggtgcttctatgtgg agttgattagaggacggaaagaggagacaaaagtctggtggaccagtaactcaattgtcgtgttttg tggcacctcagggacttatggtactggctcttggccggatggtgctgacatcaatctcatgccaatt N2-2002A (SEQ ID NO: 8)
MNPNQKIITIGSVSLIIATICFLMQIAILVTTVTLHFKQHDYNSPPNNQATLCEPTIIER

KTTEIVYLTNTTIEKEVCPKLAEYRNWSKPQCNITGFAPFSKDNSIRLSAGGDIWVTREP

YVSCDPDKCYQFALGQGTTLNNGHSNNTVHDRTPYRTLLMNELGVPFHLGTRQVCMAWSS

SSCHDGKAWLHVCVTGNDNNATASFIYNGRLVDSIGSWSKNILRTQESECVCINGTCTVV

MTDGSASGKADTKILFVEEGKIVHISTLLGSAQHVEECSCYPRFPGVRCVCRDNWKGSNR

PIVDINVKNYSIVSSYVCSGLVGDTPRESDSVSSSYCLDPNNEKGGHGVKGWAFDDGNDV

WMGRTINETLRLGYETFKVIEGWSTANSKSQTNRQVIVEKGDRSGYSGIFSVEGKNCINR

CFYVELIRGRKEETKVWWTSNSIVVFCGTSGTYGTGSWPDGADINLMPI

N1-pandemic EU (SEQ ID NO: 11)
atgaatccaaaccaaaagataataaccattggttcggtctgtatgacaattggaatggctaacttaa tattacaaattggaaacataatctcaatatggattagccactcaattcaacttgggaatcaaagtca gattgaaacatgcaatcaaagcgtcattacttatgaaaacaacacttgggtaaatcagacatatgtt aacatcagcaacaccaactttgctgctggacagtcagtggtttccgcgaaattagcgggcaattcct ccctctgccctgttagtggatgggctatatacagtaaagacaacagtgtaagaatcggttccaaggg ggatgtgtttgtcataagggaaccattcatatcatgctccccttagaatgcagaaccttcttcttg actcaaggggccttgctaaatgacaaacattccaatggaaccattaaagataggagcccatatcgaa -continued

```
ccctgatgagctgtcctattggtgaagttccctctccatacaactcaagatttgagtcggtcgcttg gtcagcaagtgcttgtcacgatggcatcaattggctaacaatcggaatttctggcccagacagtggg gcagtggctgtattaaagtacaatggcataataacagacactatcaagagttggaaaaacaatatat tgagaacacaagagtctgaatgtgcatgtgtaaatggttcttgctttaccataatgaccgatggacc aagtgatggacaggcctcatacaagatcttcagaatagaaaagggaaagatagtcaaatcagtcgaa atgaatgcccctaattatcactatgaggaatgctcctgttatcctgattctagtgaaatcacatgtg tgtgcagggataactggcatggctcgaatcgaccgtgggtgtctttcaaccagaatctggaatatca gataggatacatatgcagtgggattttcggagacaatccacgccctaatgataagacaggcagttgt ggtccagtatcgtctaatggagcaaatggagtaaaaggattttcattcaaatatggcaatggtgttt ggatagggagaactaaaagcattagttcaagaaaaggttttgagatgatttgggatccaaatggatg gactgggacagacaaaaacttctcaataaagcaagatatcataggaataaatgagtggtcaggatac agcgggagttttgttcagcatccagaactaacagggctgaattgtataagaccttgcttctgggttg aactaatcagagggcgacccaaagagaacacaatctggactagcgggagcagcatatccttttgtgg tgtaaacagtgacactgtgggttggtcttggccagacggtgctgagttgccatttaccattgacaag taa
```

N1-pandemic EU (SEQ ID NO: 12)
MNPNQKIITIGSVCMTIGMANLILQIGNIISIWISHSIQLGNQSQIETCNQSVITYENNTWVNQTYV
NISNTNFAAGQSVVSAKLAGNSSLCPVSGWAIYSKDNSVRIGSKGDVFVIREPFISCSPLECRTFFL
TQGALLNDKHSNGTIKDRSPYRTLMSCPIGEVPSPYNSRFESVAWSASACHDGINWLTIGISGPDSG
AVAVLKYNGIITDTIKSWKNNILRTQESECACVNGSCFTIMTDGPSDGQASYKIFRIEKGKIVKSVE
MNAPNYHYEECSCYPDSSEITCVCRDNWHGSNRPWVSFNQNLEYQIGYICSGIFGDNPRPNDKTGSC
GPVSSNGANGVKGFSFKYGNGVWIGRTKSISSRKGFEMIWDPNGWTGTDKNFSIKQDIIGINEWSGY
SGSFVQHPELTGLNCIRPCFWVELIRGRPKENTIWTSGSSISFCGVNSDTVGWSWPDGAELPFTIDK N1-Eurasian Avian (SEQ ID NO: 13)
```
atgaacccaaatcagaagataataatcattagttcaatctgtatgacaaatggaattgctagcttga tattacaaattgggaacataatatcaatatggattagccattcaattcaaattgagaacccaaacca gaccgaccatgcaatcaaagcgttattatttacgaaaacaacacatgggtaaatcaaacgtatgtta acatcagcaacaataattttgttgttgaacagacagtggtttcaatgaaattagcgggcagttcttc tctctgccctgttagtggatgggctatatacagtaaagataacagtgtaagaatcggttccaaaggg gatgtgtttgtcataagagagccattcatctcatgctcccatttggaatgtagaaccttcttcttaa ctcaaggggccctactgaatgataaacattctaatggaaccgttaaagacagaagcccctatcgaac cctgatgagctgtcctattggtgaagtccctctccatacaactcaaaatttgagtcagttgcttgg tcagcaagtgcttgccatgatggcaccagttggttgacaattgggatttctggtccagacaatggag cagtggctgtgttgaaatacaatgacataataacagacactatcaagagttggaaaaacaacatatt gagaacacaagaatctgaatgtgcatgttttgaatggttcttgctttactgtaatgaccgatggacca agtaatgggcaggcctcatacaagatcttcaaaatagaaaaggggaaagtagtcaaatcagtcgagt tgaatgctcctaattatcactatgaggaatgttcctgttatcctgattctggtgaaatcatatgtgt atgcagggacaattggcatggctcgaatcgaccatgggtgtctttcaatcagaatctggagtatcag ataggatacatatgcagtggggttctcggagacaatccgcgccctaatgataaacaggcagttgtg gtccagtatcatctcatggagcaaatggggtaaaagggttttcgtttaaatacggcaatggaatttg
```

-continued

```
gatagggagaactaaaagcactattacaaggagtggttttgagatgatttgggacccaaacggatgg actggaacagacaataatttctcagtgaagcaagatatcgtaggaataactaactggtcaggatacg cgggagttttgtccaacatccagaattaaccggattggattgtattagaccttgcttctgggttgaa ctaatcagagggagacccaaagagaacacaatctggactagcggaagcagcatatccttttgtggtg taaatagtgacactgtgggttggtcttggccagacggtgctgagttgccatttaccattgacaagta a
```

N1-Eurasian Avian (SEQ ID NO: 14)
MNPNQKIIIISSICMTNGIASLILQIGNIISIWISHSIQIENPNQTEPCNQSVIIYENNTWVNQTYV
NISNNNFVVEQTVVSMKLAGSSSLCPVSGWAIYSKDNSVRIGSKGDVFVIREPFISCSHLECRTFFL
TQGALLNDKHSNGTVKDRSPYRTLMSCPIGEVPSPYNSKFESVAWSASACHDGTSWLTIGISGPDNG
AVAVLKYNDIITDTIKSWKNNILRTQESECACLNGSCFTVMTDGPSNGQASYKIFKIEKGKVVKSVE
LNAPNYHYEECSCYPDSGEIICVCRDNWHGSNRPWVSFNQNLEYQIGYICSGVLGDNPRPNDRTGSC
GPVSSHGANGVKGFSFKYGNGIWIGRTKSTITRSGFEMIWDPNGWTGTDNNFSVKQDIVGITNWSGY
SGSFVQHPELTGLDCIRPCFWVELIRGRPKENTIWTSGSSISFCGVNSDTVGWSWPDGAELPFTIDK N2-Gent/1984

(SEQ ID NO: 15)
```
atgaatccaaatcaaaagataataacaattggttctgtttctctcactattacaacaatgtgcctct tcttgcagattgccatcctagtaactactataacattgcatttcaagcaatatgaatgcgattcccc tgcaaacaaccaagtaataccgtgtgaaccaataataatagaaaaaaacataacaaaaatagtgtat ttgaccaataccaccatagagaaagaggtatgcccaaaattaggggaatacaggaattggtcaaaac cacaatgcaagatcacaggatttgcacctttttctaaggacaattcaattcggctctctgcgggtgg ggccatttgggtcacgagagaaccttatgtgtcatgcgaccctaacaagtgttatcaatttgcatta ggacagggaaccacattagataacagacattcaaatgacacaatacatgatagaaccccttttagaa ccctgttgatgagtgaattaggtgttccatttcatttgggaaccagacaagtatgcatagcatggtc cagttcaagttgtcacgatgggaaagcttggttgcatgttttgtgtcactgggcatgataaaaatgca actgctagttttcatttatgacggaaagcttgtagacagcatcagttcatggtccaaaaacatactcc ggactcaggaatcagaatgtgtttgtatcgatggaatctgtacagtggtgatgactgatggaagtgc ttcagggaaagctgatactaagatactatttattgaaaaagggaagatcattcatattagtccattg ttgggaagtgctcagcatgtagaagaatgttcctgttaccctagatacccctgatgtcaggtgtattt gcagggataactggaaaggttcaaataggcccatcgtagacataagaatgaaaaattatagcattgg ttccagttatatgtgctcaggacttgttggcgacacacccaggaacaatgatgggtctagtaatagc aattgtcggaatcccaataatgaaagaggaaatcatggagtgaaaggttgggccctttgatgatggaa atgacacatggatgggaagaactatcagcaaggactcacgcttaggttacgaaaccttcaaagttgt tggtggttggtcccaacccaattccaaatcccagataaatagacaagttattgttgacagcgataat agatcaggttactctggtatttttctctgttgaggggaaagattgcattaataggtgttttttatgtgg aactaataagaggaaggagacaggaaactagagtgtggtggacttcgaacagtattgttgtgttctg tggcacttctggcacctatgggtcaggctcatggcccgatggagcaaacatcaatttcatgcctgta taa
```

N2-Gent/1984

(SEQ ID NO: 16)
MNPNQKIITIGSVSLTITTMCLFLQIAILVTTITLHFKQYECDSPANNQVIPCEPIIIEKNITKIVY
LTNTTIEKEVCPKLGEYRNWSKPQCKITGFAPFSKDNSIRLSAGGAIWVTREPYVSCDPNKCYQFAL
GQGTTLDNRHSNDTIHDRTPFRTLLMSELGVPFHLGTRQVCIAWSSSSCHDGKAWLHVCVTGHDKNA

-continued

TASFIYDGKLVDSISSWSKNILRTQESECVCIDGICTVVMTDGSASGKADTKILFIEKGKIIHISPL

LGSAQHVEECSCYPRYPDVRCICRDNWKGSNRPIVDIRMKNYSIGSSYMCSGLVGDTPRNNDGSSNS

NCRNPNNERGNHGVKGWAFDDGNDTWMGRTISKDSRLGYETFKVVGGWSQPNSKSQINRQVIVDSDN

RSGYSGIFSVEGKDCINRCFYVELIRGRRQETRVWWTSNSIVVFCGTSGTYGSGSWPDGANINFMPV

N2-Italy/4675/2003

(SEQ ID NO: 17)
atgaattcaaatcaaaagataataacaattggctctgtttctctcactattgccacactatgcctcc ttatgcaaattgctatcatggtaactactgtaacatttcatttcaagcagtatgaatacaactcccc cccgaacaaccaagtaatgttgtgtgaaccaacgataattgaaagaaacataacagagacagtgtac atgaccaacaccaccatagtgaaagaaatatgccccaaactagcggaatacagaaattggtcaaaac cgcaatgcaaaattacaggatttgcaccttttttcaaaggacaactcaattcggctttccgctggtgg ggacatctgggtgacaagagaaccttatgtgtcatgcgatcctaacaagtgttatcaatttgccctt gggcagggaacaacgttaaacaacaggcattcaaatgacacagtacatgatagaacccccttaccgaa ccctgttgatgaatgaattgggtgttccatttcatttaggaaccaagcaggtttgcatagcttggtc cagttcaagttgtcatgatggaaaagcatggttgcatgtttgtgtaactgggcatgatgaaaatgca actgccagtttcatttacaacgagagacttgtagatagtattggttcatggtccaagaaaatcctca gaacccaggagtcggaatgcgtttgcataaatgggacttgtacagtggtgatgacagatgggagtgc ttcaggtagagctgatactaaaatactattcattgaggaggggaaaatcgttcatgttagccaactg acaggaagtgctcagcatgtagaggagtgctcctgttatccccggtatcctggtgtcagatgtgttt gcagagataattggaaaggctccaataggcccattgtagatataaatgtaaaggatcatagcattgt ttccagttatgtgtgctcaggacttgtcggagacacacccagaaaaaacgacagctctagcagtagt aactgcctgaatcctaacaatgaagaaggggggtcatggggtgaaaggctgggcctttgatgatgaaa atgacttgtggatgggaagaacgatcagcgaaaagttacgattaggttatgaaaccttcaaggtcat tgaaggctggtccaagcctaattccaaattgcagataaataggcaagtaatagttgacaaagataat agatccggttattctggtattttctctgttgaaagtaaaagttgcatcaatcggtgcttttatgtgg agttgataagaggaaggaaacaggaaaatgaagtatggtggacctcaaacagcattgttgtattttg tggcacctcaggtacatatggaacaggctcatggcctgatggggcagacatcaatctcatgcctata tga N2-Italy/4675/2003

(SEQ ID NO: 18)
MNSNQKIITIGSVSLTIATLCLLMQIAIMVTTVTFHFKQYEYNSPPNNQVMLCEPTIIERNITETVY

MTNTTIVKEICPKLAEYRNWSKPQCKITGFAPFSKDNSIRLSAGGDIWVTREPYVSCDPNKCYQFAL

GQGTTLNNRHSNDTVHDRTPYRTLLMNELGVPFHLGTKQVCIAWSSSSCHDGKAWLHVCVTGHDENA

TASFIYNERLVDSIGSWSKKILRTQESECVCINGTCTVVMTDGSASGRADTKILFIEEGKIVHVSQL

TGSAQHVEECSCYPRYPGVRCVCRDNWKGSNRPIVDINVKDHSIVSSYVCSGLVGDTPRKNDSSSSS

NCLNPNNEEGGHGVKGWAFDDENDLWMGRTISEKLRLGYETFKVIEGWSKPNSKLQINRQVIVDKDN

RSGYSGIFSVESKSCINRCFYVELIRGRKQENEVWWTSNSIVVFCGTSGTYGTGSWPDGADINLMPI

N2-Scotland/1994 (clade 1)

(SEQ ID NO: 19)
atgaatccaaatcagaagataataacaattggctctgtttctctcgtcattgcaacattatgcttct taatgcagatggccatcctaataact -continued

```
ctcaatgcaaaataacaggctttgcaccttttccaaggacaattcaattcgactttctgctggtgg ggacatatgggtgacgagggaaccttacgtgtcatgcgagcctggcaaatgttatcagtttgcactc gggcaagggaccacactagacaataaacattcaaacgatacaatacatgacagaaccccctatcgaa ctctattgatgaatgaattgggtgtcccatttcatttagggacaagacaagtgtgtattgcatggtc cagctcaagttgttatgatgggaaagcatggttgcatgtctgtatcactggacatgataaaaatgca actgccagtttcatttacgatggtagacttgtagatagcattggttcatggtctaaaaatatactta gaacccaggaatcagaatgcgtttgcatcaatggggtctgtacagtagtaatgactgatggaagtgc ttcgggaagagctgatactaaaatactattcattgaagaagggaaaattgttcatattagcccatta gcggggagtgcacagcatgtggaggagtgctcctgttatccccgatatcctggcgtaaggtgtatct gcagagacaactggaaaggctctaacagacccgttgtggatataaatatagaagattatagcattga ttccagttatgtgtgttcagggcttgttggcgacacacccagaatcaatgacggatccagtagtagc tactgccgtgatcctaacaacgaaaaaggaaatcacggagtgaagggctgggcttttgacgatggaa atgatgtgtggatgggaagaacgatcaacgaagattcacgctcaggttatgaaacattcaaagtcat tggtggttggtccactcctaattccaaattgcagataaataggcaagtaatagttgatagcaacaat aggtcaggttattctggtgttttctccgttgaaggcaaaagctgcatcaatagatgtttctacgtgg agttgataagaggaagaaggtcagaagcgcgagtatggtggacctcaaacagtattgttgtattttg tggcacttcaggtacctatggaacaggctcatggcctgatggagcagacatcaacctcatgcctata tga
```

N2-Scotland/1994 (clade 1)

(SEQ ID NO: 20)

MNPNQKIITIGSVSLVIATLCFLMQMAILITTVKLHFKQYECGFPANNQVITCEPTVIERNTTEIVY

LTNTTIEKETCHKTVEYRNWSKPQCKITGFAPFSKDNSIRLSAGGDIWVTREPYVSCEPGKCYQFAL

GQGTTLDNKHSNDTIHDRTPYRTLLMNELGVPFHLGTRQVCIAWSSSSCYDGKAWLHVCITGHDKNA

TASFIYDGRLVDSIGSWSKNILRTQESECVCINGVCTVVMTDGSASGRADTKILFIEEGKIVHISPL

AGSAQHVEECSCYPRYPGVRCICRDNWKGSNRPVVDINIEDYSIDSSYVCSGLVGDTPRINDGSSSS

YCRDPNNEKGNHGVKGWAFDDGNDVWMGRTINEDSRSGYETFKVIGGWSTPNSKLQINRQVIVDSNN

RSGYSGVFSVEGKSCINRCFYVELIRGRRSEARVWWTSNSIVVFCGTSGTYGTGSWPDGADINLMPI

N2-Scotland/1994 (clade 2)

(SEQ ID NO: 21)

```
atgaatccaaaccagaaaataataacgatcggttctgtctccttgatcattgcaacaatgtgctttt tcatgcaagttgccattctggtaactactgtaacattgcatttcaggcagtgcgaatgcaactcctc cgcaaccaaccaaataatgccatgtaaaccaacaaaaatagagagaaacataactgaaattgtgtac ttaaccaataccaccataaaaacagaggtatgccccaaactagtgaaatacagggattgggcaaaac cacaatgtagaatcacagggtttgcaccttttccaaggacaattcgattcggctttctgccggtgg ggccatttgggtaacgagagaaccctatgtatcatgcgatcttagcaagtgttaccagtttgcgctc ggacaggggactacactagacaacagacattcaaatgacacaatacatgatgaactccttatcgga ccctattgatgaatgaattgggtgttccatttcatttaggaaccaggcaagtgtgtatagcttggtc cagttcaagttgtcacgatggaaaagcatggctgcatgtttgtgtcactgggtatgataaaaatgct actgctagcctcatttatgacggaaggcttgtggacagcatcggttcatggtcccaaaacatcctcc ggacccaggaatcggaatgtgtttgtataaatggtacttgcacagtggtaatgactgatgggagtgc ttcaggaaaagctgataccagaatactatttattgaagaagggaagattattcacattagtccattg acaggaagtgcacagcatgttgaagagtgttcttgttatcctcgataccccggtgtaagatgtgttt gtagagacaactggaagggctctaacagacccgtcgtggatataaatgtaaaagattataaaattaa
```

-continued

```
ctccagttatgtatgctcaggccttgttggcgatacacccagaaacaacgatagatctagcaatagc aactgccaaaatcctaacaaccagagagggaatcatggagtgaagggctgggcctttgacgatggaa atgacatatggatgggaagaaccatcagcaatgattcacgtttaggttatgaaactttcaaagttat tggtggttggtccaaacccaactccaaagttcagacaaataggcaagtcatagttgacagcgataat agatcaggttattctggcgttttctctgttgaaggcaaaagctgcatcaataggtgcttttatgtag agctaataagaggaaggagacaggaagctagagtatggtggacttcgaacagtattgttgtgttttg tggtacttcgggtacatatggttcaggctcatggcctgatggggctgacatcaatcttatgcctata taa
```

N2-Scotland/1994 (clade 2)
(SEQ ID NO: 22)
MNPNQKIITIGSVSLIIATMCFFMQVAILVTTVTLHFRQCECNSSATNQIMPCKPTKIERNITEIVY

LTNTTIKTEVCPKLVKYRDWAKPQCRITGFAPFSKDNSIRLSAGGAIWVTREPYVSCDLSKCYQFAL

GQGTTLDNRHSNDTIHDRTPYRTLLMNELGVPFHLGTRQVCIAWSSSSCHDGKAWLHVCVTGYDKNA

TASLIYDGRLVDSIGSWSQNILRTQESECVCINGTCTVVMTDGSASGKADTRILFIEEGKIIHISPL

TGSAQHVEECSCYPRYPGVRCVCRDNWKGSNRPVVDINVKDYKINSSYVCSGLVGDTPRNNDRSSNS

NCQNPNNQRGNHGVKGWAFDDGNDIWMGRTISNDSRLGYETFKVIGGWSKPNSKVQTNRQVIVDSDN

RSGYSGVFSVEGKSCINRCFYVELIRGRRQEARVWWTSNSIVVFCGTSGTYGSGSWPDGADINLMPI

The following examples serve to provide further appreciation of the invention but are not meant in any way to restrict the effective scope of the invention.

EXAMPLES

Example 1

Efficacy in Weaned Piglets of a Non-Adjuvanted Multivalent NA-RP Vaccine Containing Four Individual NA-RP Constructs Introduction RNA viruses have been used as vector-vehicles for introducing vaccine antigens, which have been genetically engineered into their genomes. However, their use to date has been limited primarily to incorporating viral antigens into the RNA virus and then introducing the virus into a recipient host. The result is the induction of protective antibodies against the incorporated viral antigens. Alphavirus RNA replicon particles have been used to encode pathogenic antigens. Such alphavirus replicon platforms have been developed from several different alphaviruses, including Venezuelan equine encephalitis virus (VEE) [Pushko et al., Virology 239:389-401 (1997)], Sindbis (SIN) [Bredenbeek et al., Journal of Virology 67:6439-6446 (1993) the contents of which are hereby incorporated herein in their entireties], and Semliki Forest virus (SFV) [Liljestrom and Garoff, Biotechnology (NY) 9:1356-1361 (1991), the contents of which are hereby incorporated herein in their entireties]. Moreover, alphavirus RNA replicon particles are the basis for several USDA-licensed vaccines for swine and poultry. These include: Porcine Epidemic Diarrhea Vaccine, RNA Particle (Product Code 19U5.P1), Swine Influenza Vaccine, RNA (Product Code 19A5.D0), Avian Influenza Vaccine, RNA (Product Code 19O5.D0), and Prescription Product, RNA Particle (Product Code 9PP0.00).

A study was undertaken to determine the efficacy and immunogenicity of two dose levels of a four-way non-adjuvanted NA-RP vaccine. The non-adjuvanted vaccine included four RP constructs, each of which individually encoded a single, different NA protein of a contemporary U.S. IAV-S isolate. Together these NA genes represent two N1 phylogenetic clusters and two N2 clusters predominant in the U.S. swine population. The non-adjuvanted vaccine was administered in two intramuscular (IM) vaccinations (1 mL per dose), in weaned pigs seronegative to the vaccine fraction and challenge strain. The efficacy of the four-way NA-RP vaccine was then tested against heterologous N1 (H1N1 virus) and N2 (H1N2 virus) challenge infections.

Materials and Methods

Construction of NA-RP Antigens:

The VEE replicon vectors designed to express neuraminidase (NA) genes were constructed as previously described [see, U.S. Pat. No. 9,441,247 B2; the contents of which are hereby incorporated herein by reference], with the following modifications. The TC-83-derived replicon vector "pVEK" [disclosed and described in U.S. Pat. No. 9,441,247 B2] was digested with restriction enzymes AscI and PacI. A DNA plasmid containing the codon-optimized open reading frame sequence of the N1 or N2 genes (Table 1) with 5' flanking sequence (5'-GGCGCGCCGCACC-3') [SEQ ID NO: 9] and 3' flanking sequence (5'-TTAATTAA-3') [SEQ ID NO: 10], was similarly digested with restriction enzymes AscI and PacI. The synthetic gene cassette was then ligated into the digested pVEK vector, and the resulting clones were re-named "pVHV-N1-pandemic", "pVHV-N1-classic", pVHV-N2-2002", and "pVHV-N2-1998". The "pVHV" vector nomenclature was chosen to refer to pVEK-derived replicon vectors containing transgene cassettes cloned via the AscI and PacI sites in the multiple cloning site of pVEK.

Production of TC-83 RNA replicon particles (RP) was conducted according to methods previously described [U.S.

Pat. No. 9,441,247 B2 and U.S. Pat. No. 8,460,913 B2; the contents of which are hereby incorporated herein by reference]. Briefly, pVHV replicon vector DNA and helper DNA plasmids were linearized with NotI restriction enzyme prior to in vitro transcription using MegaScript T7 RNA polymerase and cap analog (Promega, Madison, WI). Importantly, the helper RNAs used in the production lack the VEE subgenomic promoter sequence, as previously described [Kamrud et al., *J Gen Virol.* 91(Pt 7):1723-1727 (2010)]. Purified RNA for the replicon and helper components were combined and mixed with a suspension of Vero cells, electroporated in 4 mm cuvettes, and returned to OptiPro SFM cell culture media (Thermo Fisher, Waltham, MA). Following overnight incubation, alphavirus RNA replicon particles were purified, formulated in phosphate buffered saline with 5% sucrose (w/v) and 1% swine serum, passed through a 0.22 micron membrane filter, and dispensed into aliquots for storage. Titer of functional RP was determined by immunofluorescence assay on infected Vero cell monolayers. Batches of RP were identified according to the gene encoded by the packaged replicon.

TABLE 1

N1 and N2 Genes Encoded in NA-RP Constructs

| NA phylogenetic cluster | Gene donor strain | GenBank Accession |
|---|---|---|
| N1-classic | A/swine/Iowa/A01410307/2014 (H1N1) | KJ605083 |
| N1-pandemic | A/swine/Minnesota/A01483170/2014 (H1N1) | KP036969 |
| N2-1998 | A/swine/Michigan/A02077465/2015 (H1N2) | KR982634 |
| N2-2002 | A/swine/Illinois/A01475495/2014 (H1N2) | KJ941362 |

Viruses:

Challenge viruses were obtained from the USDA National Veterinary Services Laboratories.

A/swine/Illinois/A01554351/2015 (H1N1) possesses an HA gene of the H1-gamma cluster and a NA gene of the N1-classic cluster.

A/swine/Iowa/A02076654/2015 (H1N2) possesses an HA gene of the H1-delta1 cluster and a NA gene of the N2-2002A cluster.

The viruses were propagated in MDCK cell culture. Confluent cells were infected for approximately 48 hours, until cytopathic effect was evident in over 70% of cell monolayer. At harvest, supernatant was removed from vessels and clarified by centrifugation before storage of the virus at −60° C. or colder.

Animals:

Weaned piglets were selected from a high health herd based on serology screening to confirm the lack of preexisting HI or NI antibodies to the vaccine and challenge strains. These animals were a mix of male and female, approximately three weeks of age at the time of first vaccination.

Vaccination and Challenge:

The treatment groups are outlined in Table 2 below. The four-way NA-RP vaccine was formulated at two dose levels: $10^6$ copies each RP/dose (low dose) and $10^7$ each RP/dose (high dose), based on an immunofluorescence-based potency assay to quantitate functional RPs. NA-RP antigens were formulated in a stabilizer consisting of 1% swine serum and 5% sucrose. The placebo vaccine consisted of the same stabilizer and no antigen. The non-adjuvanted vaccines were administered IM in a 1-mL dose to pigs at 3 and 7 weeks of age. The dose levels were back-titrated by IFA test on retained vaccine material following vaccination. Serum samples were collected at the day of the first vaccination, the day of the second vaccination, and the day of challenge infection.

TABLE 2

TREATMENT GROUPS

| Group | No. of pigs | Vaccine | Copy No. per dose (1 mL) | Challenge Strain |
|---|---|---|---|---|
| 1 | 8 | High dose NA-RPs | $10^7$ | H1N1 |
| 2 | 8 | Low dose NA-RPs | $10^6$ | |
| 3 | 9 | Placebo | — | |
| 4 | 8 | High dose NA-RPs | $10^7$ | H1N2 |
| 5 | 8 | Low dose NA-RPs | $10^6$ | |
| 6 | 9 | Placebo | — | |

The challenge infection was administered to the pigs 3 weeks after the second vaccination. The challenge materials of the H1N1 (H1-gamma-N1-classic) and H1N2 (H1delta1b-N2-2002A) viruses were both formulated to target doses of $10^{6.5}$ TCID50/pig (6 mL volume). The challenge material was administered by the intratracheal route. The challenge virus doses were confirmed by back-titration of retained challenge material. Nasal swabs were collected from all pigs at −1, 1, 3, and 5 days post challenge.

Necropsy was performed 5 days post challenge (DPC). The pigs were euthanized by barbiturate overdose at 5 DPC under supervision of a licensed veterinarian. The lungs were collected and observed in order to document the surface area of each lobe affected by macroscopic lesions, resulting in a comprehensive percent lung lesion score. Bronchoalveolar lavage and nasal swabs were collected from all pigs to measure virus titers. The lung sections were collected for microscopic lesion analysis.

Immune Response Analysis:

IAV-S specific antibodies in pig serum samples were determined by HI and NI tests. The sera were heat-inactivated for 30-60 minutes at 56° C. For HI, the sera were also treated with receptor destroying enzyme and/or kaolin and absorbed to turkey red blood cells to remove non-specific agglutinins. The HI test was performed as described previously [Kitikoon et al., *Methods Mol Biol* 1161: 295-301 (2014)], using turkey red blood cells. The NI test was performed with minor modifications by the method described previously [Sandbulte and Eichelberger, *Methods Mol Biol* 1161: 337-45(2014)]. Briefly, 2-fold serial dilutions of serum was mixed with expressed protein antigen at equal volumes on fetuin-coated 96-well plates and incubated overnight at 37° C. Peanut agglutinin horseradish peroxidase conjugate (PNA-HRP) was added for 2 hours at room temperature to bind fetuin molecules stripped of sialic acid. Signal was obtained with TMB substrate, and results read at 650 nm. The mean optical density (OD) of the negative control, (no NA antigen added), was subtracted from all wells. Then the OD values of test samples were normalized on a scale of 0-100%, where the mean OD of positive control wells (containing NA antigen but no serum) was defined as 100%. The NI antibody titer was defined as the highest dilution of the sample that inhibited≥50% of neuraminidase activity.

Pathological Examination of Lungs:

Macroscopic lesions observed on the exterior of all lung lobes (well-demarcated purple to plum-colored consolidations) were recorded on grid diagrams of the lung anterior and posterior. Comprehensive scores (percent lung lesion) for each pig were calculated according to the number of lesion-affected grids.

Virus Shedding:

Nasal swabs and BAL fluids were 10-fold serially diluted with infecting media [Dulbeco's minimum essential medium (DMEM) supplemented with 0.3% bovine serum albumin, fraction V; 2 mM L-glutamine; 25 µg/mL gentamycin; 2 µg/mL trypsin IX] and 100 µL of each dilution was added to quadruplicate wells of confluent MDCK cells in a 96-well plate. Plates were incubated at 37° C. with 5% $CO_2$ and observed after 72 hours for the presence of infectious virus by hemagglutination tests of supernatants from each well. IAV-S titers were calculated by the method of Spearman-Kärber and expressed as log 10 TCID50 per mL.

Results

Immune responses of pigs vaccinated with multivalent NA-RP, see FIG. 1A-1D.

The four-way NA-RP vaccines, high and low doses of vaccine ($10^7$ and $10^6$ RP copies/dose, respectively) induced functional NI antibody titers against all four of the NA components.

NI titers induced by the high dose vaccine were greater by approximately 1-2 two-fold dilutions.

Pigs in the placebo vaccine group remained seronegative.

Figure 2A:
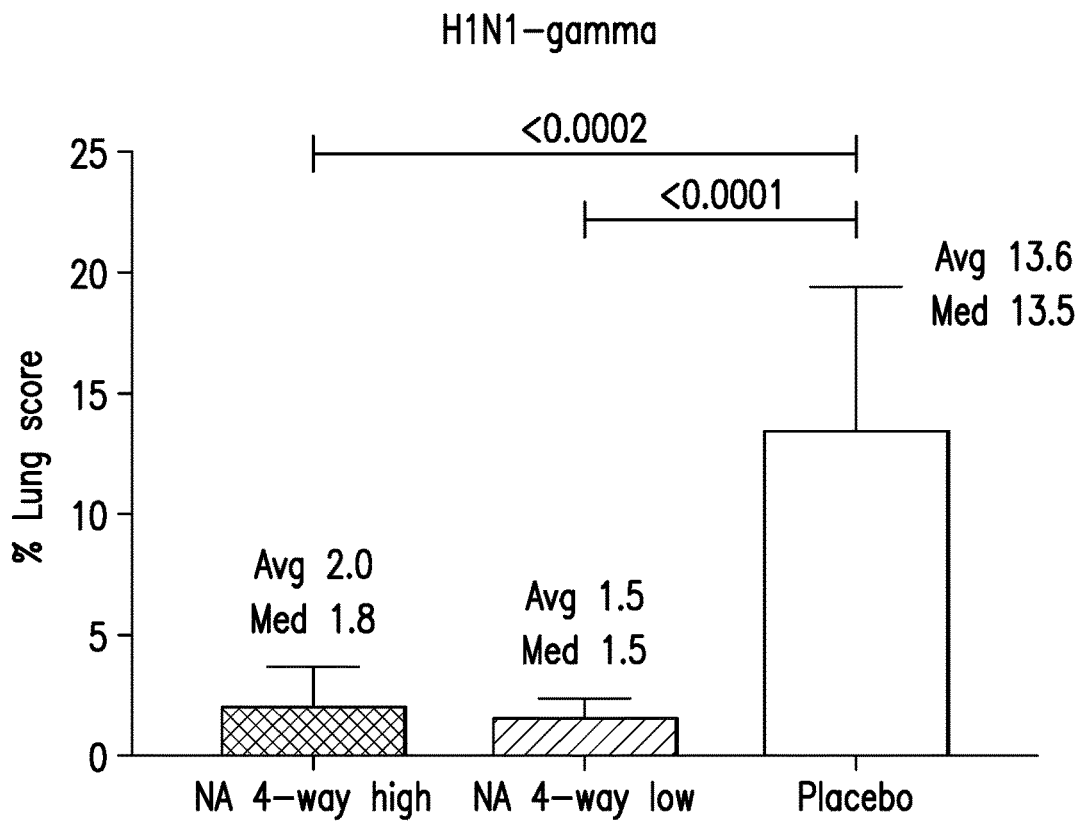
FIGS. 2A and 2B depict the lung lesion scores of pigs following administration of the vaccination compositions described in Example 1 below, and challenge infection with (A) H1-gamma-N1-classic or (B) H1-delta1-N2-2002A viruses.
Figure 2B:
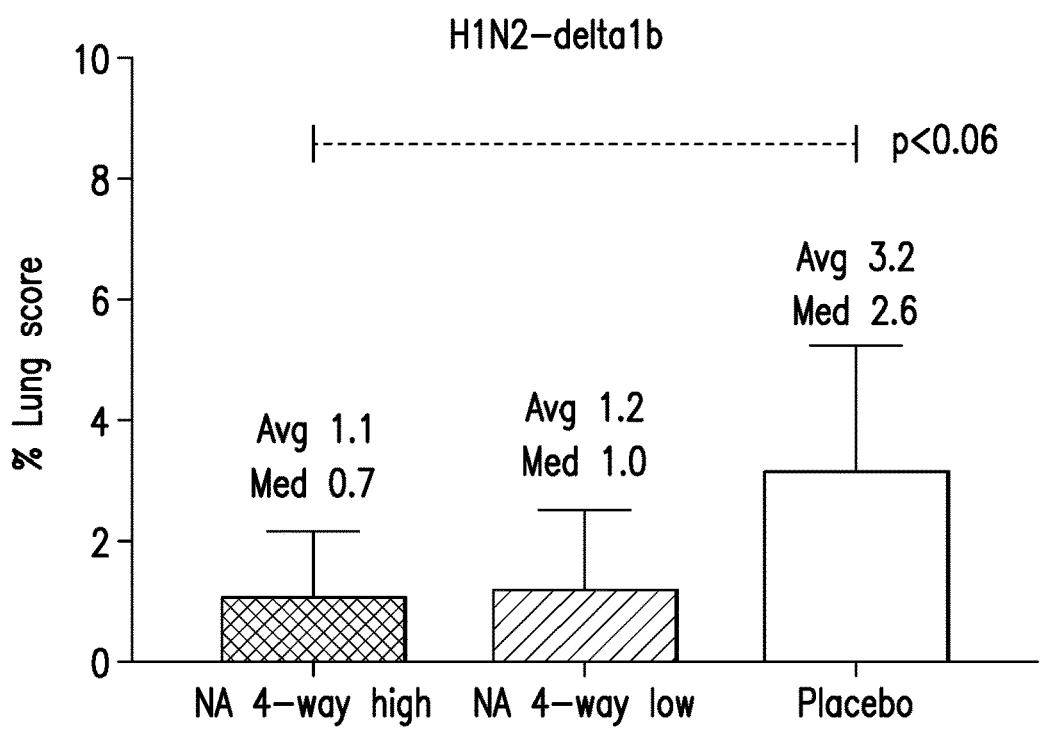

Efficacy of Four-Way NA-RP Vaccine Against Challenge Infections:

Lung Lesions: see, FIGS. 2A-2B.

The H1N1 challenge infection caused over 13% lesions on the lungs of placebo control pigs. Both treatment groups immunized with the high-dose and low-dose had significantly lower lung lesion scores 5 days post H1N1 challenge than the immunologically naïve placebo group (p<0.05). Protection in terms of lung lesions was robust regardless of the vaccine dose level.

The H1N2 challenge infection caused only 3.2% lesions on the lungs of placebo control pigs. Both treatment groups had lower lung lesion scores 5 days post H1N2 challenge than the immunologically naïve placebo group, with mean lung lesion scores below of 1.1% and 1.2%, but differences between vaccinated groups and the placebo group were not statistically significant.

Figure 3A:
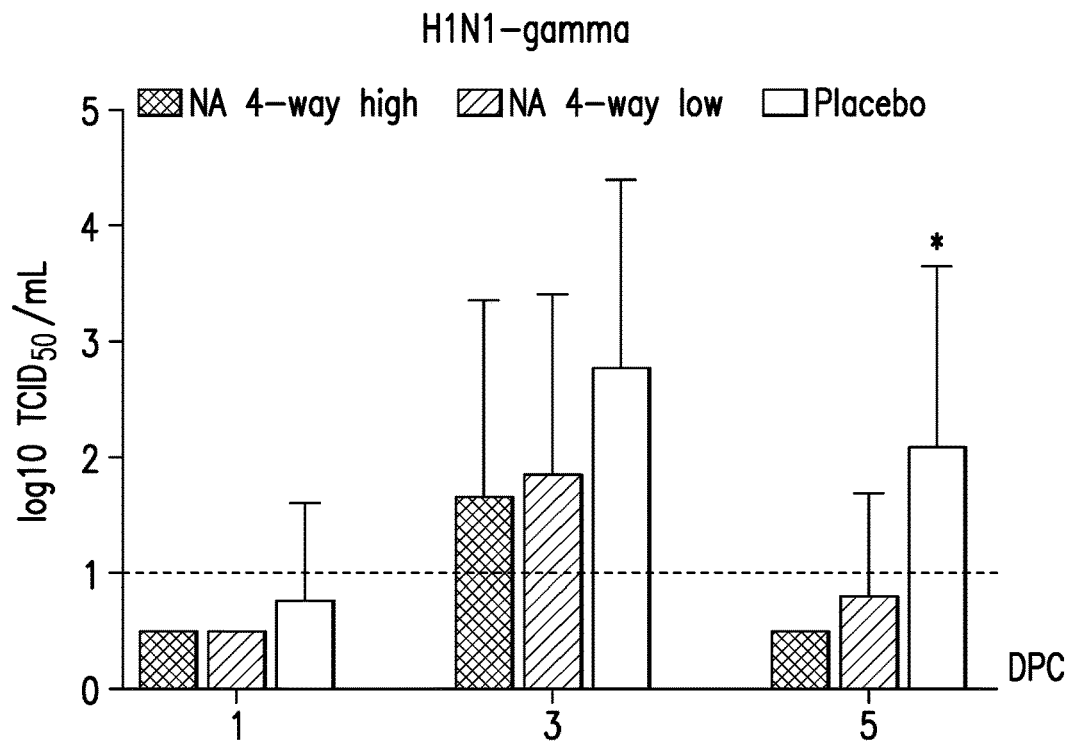
FIGS. 3A and 3B depict the viral titers in nasal swabs of pigs following administration of the vaccination compositions described in Example 1 below, and challenge infection with (A) H1-gamma-N1-classic or (B) H1-delta1-N2-2002A viruses.
Figure 3B:
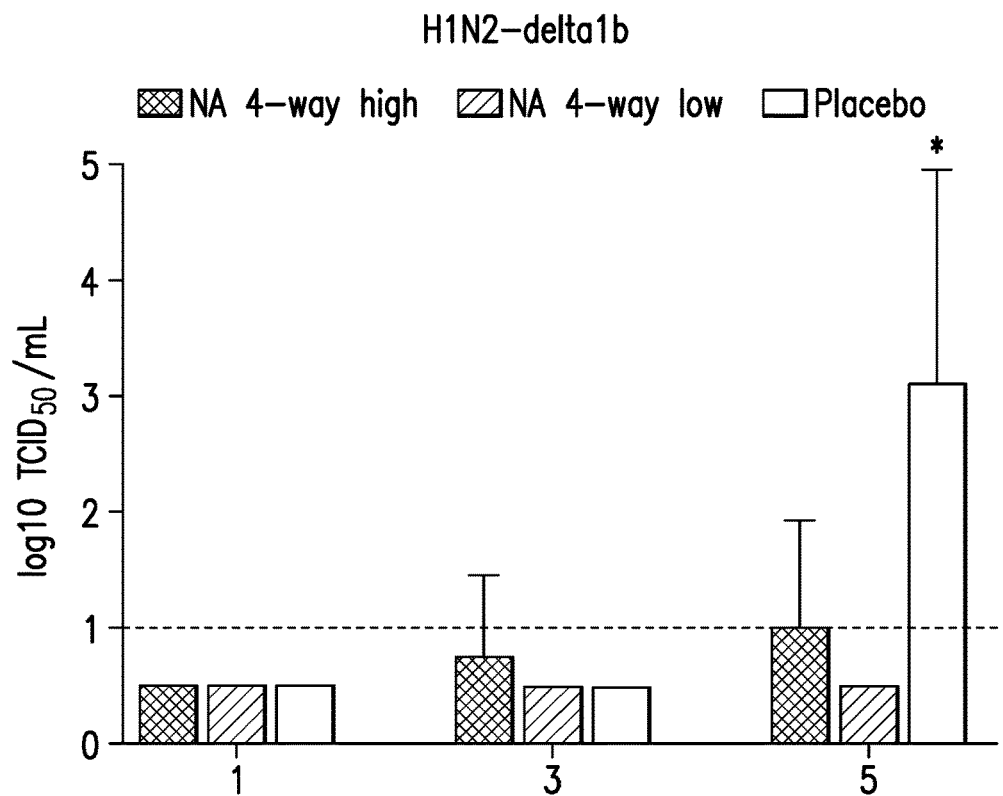

Nasal Shedding: see, FIGS. 3A-3B.

The H1N1 challenge virus shedding was maximal at 3 DPC, for all three treatment groups.

At 5 DPC there was significantly reduced virus titer in the both the high and low dose 4-way RP treatment groups compared to the placebo control (p<0.05).

The nasal shedding of H1N2 challenge virus was more delayed, with mean titers in the placebo group not exceeding the assay's lower limit of detection until 5 DPC. At 5 DPC both dose levels of the vaccinated groups had significantly reduced H1N2 viral titers (p<0.05).

Figure 4A:
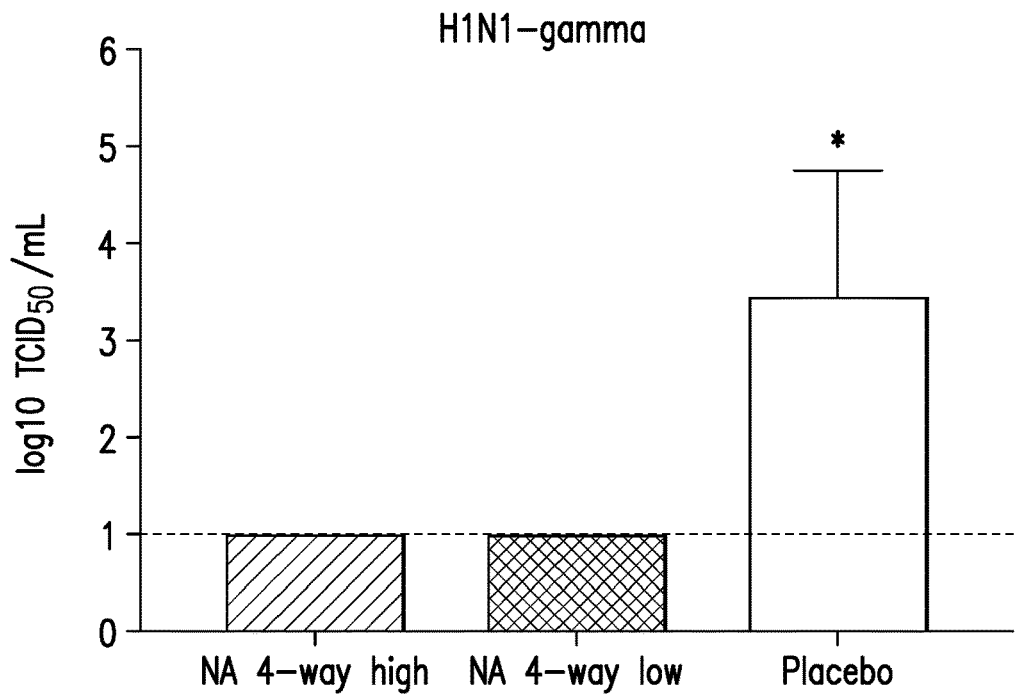
FIGS. 4A and 4B show the viral titers in bronchoalveolar lavage fluid specimens of pigs following administration of the vaccination compositions described in Example 1 below, and challenge infection with (A) H1-gamma-N1-classic or (B) H1-delta1-N2-2002A viruses.
Figure 4B:
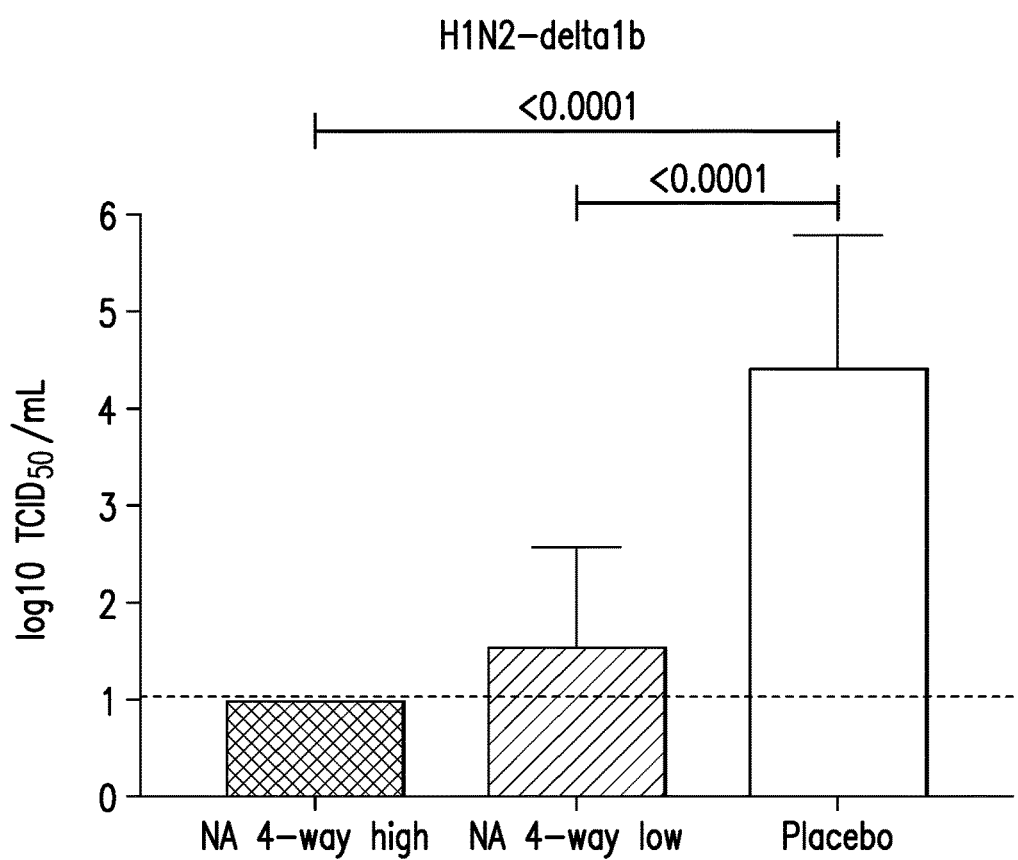
Figure 5:
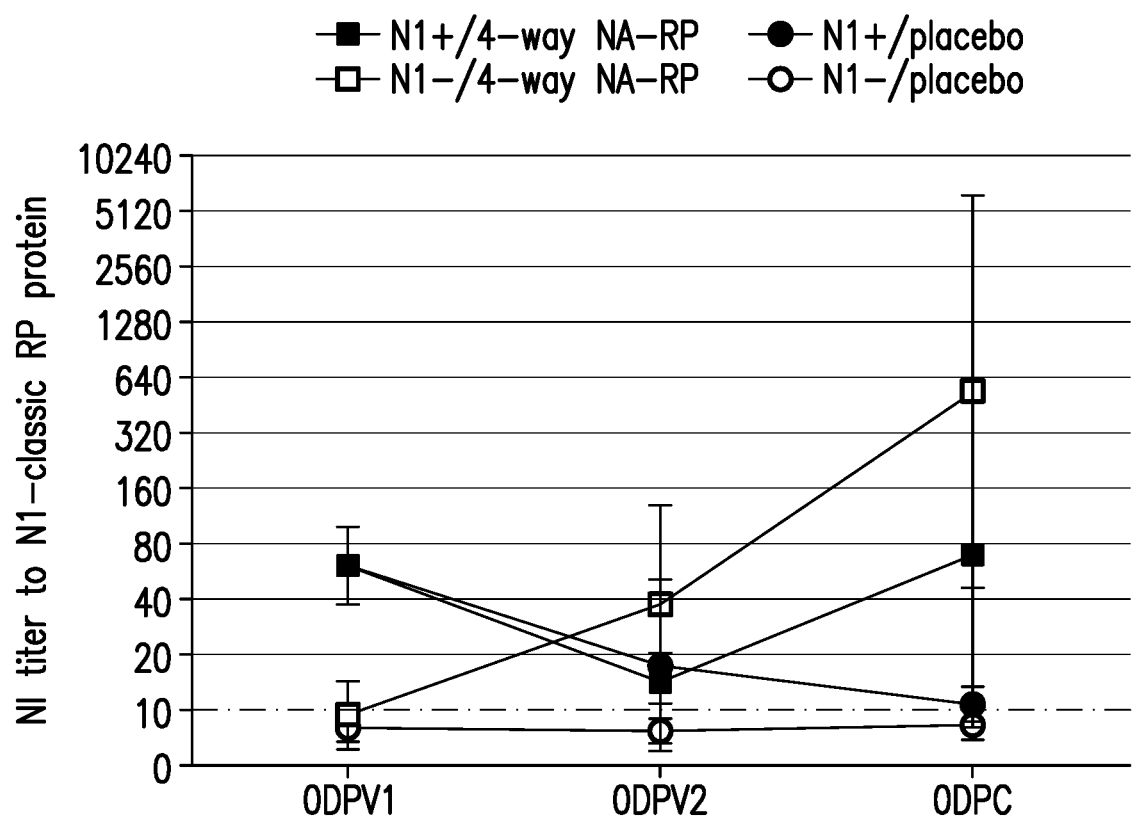
FIG. 5 depicts the serum neuraminidase inhibiting (NI) antibody responses specific to N1-classic strain of the vaccine compositions described in Example 2. The serum samples were collected prior to first vaccination (3 weeks of age), prior to second vaccination (7 weeks of age), and prior to challenge (10 weeks of age).
Figure 6:
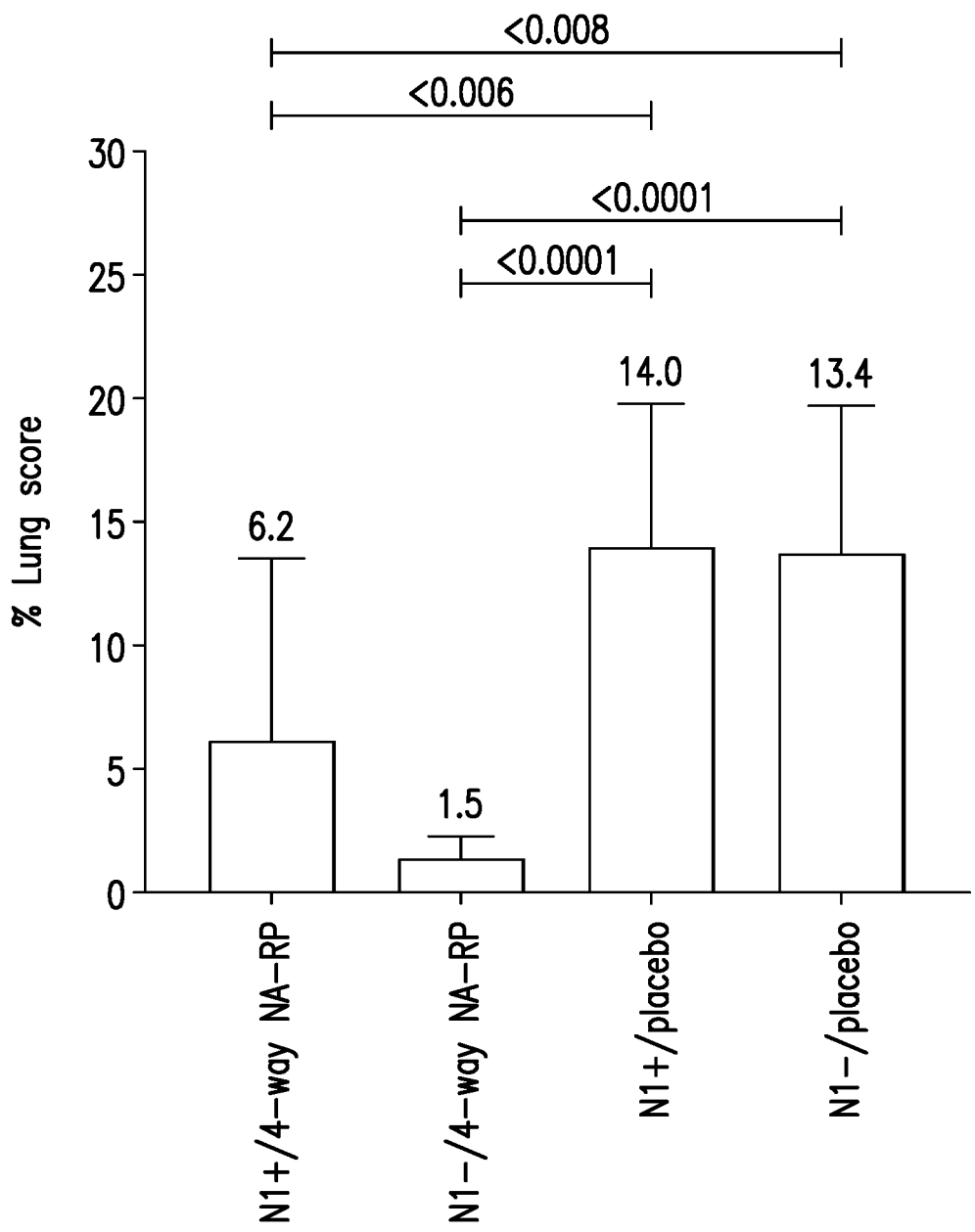
FIG. 6 shows the lung lesion scores of pigs following administration of the vaccination compositions described in Example 2 and challenge infection with H1-gamma-N1-classic virus.

Virus in Lungs: see, FIGS. 4A-4B.

The H1N1 virus titer in bronchoalveolar lavage fluid (BALF) collected at 5 DPC was over 2 logs greater in the placebo vaccine group than in either of the groups vaccinated with four-way (4-way) NA-RP, where no positive titers were detected. This represented a statistically significant difference for both vaccinated groups (p<0.05).

Virus titers in the H1N2 challenged groups showed a 2-3 log reduction between both vaccinated groups and the placebo vaccine group and were statistically significant (p<0.05).

SUMMARY

The H1N1 infection was a more robust challenge model, with high lung lesion scores accompanied by nasal and lung virus titers. The four-way NA-RP vaccinated groups showed statistically significant protection from the H1N1 virus in terms of lung lesion severity, nasal shedding, and BALF virus titer. Individual animals in the low dose 4-way NA-RP vaccine group that had developed weaker serum NI titers (<80) were also protected.

The H1N2 challenge infection was a less robust model, as lung lesions were low in the placebo group. However, even in this group there was significant protection for the vaccinated groups in terms of nasal shedding and virus titer in lungs. Multivalent NA-RP vaccine formulations, with no adjuvant, are immunogenic and demonstrated efficacy against an antigenically similar challenge NA strains.

Example 2

Efficacy of an Adjuvanted Four-Way NA-RP Vaccine Against H1N1 Infection in Weaned Pigs with N1 Antibody at the Time of First Vaccination A study was undertaken to determine the efficacy and immunogenicity of a four-way adjuvanted NA-RP vaccine. The adjuvanted vaccine included four RP constructs, each of which individually encoded a single, different NA gene of a contemporary U.S. IAV-S isolate. Together these NA genes represent two N1 phylogenetic clusters (N1-classic and N1-pandemic) and two N2 clusters (N2-1998 and N2-2002). The adjuvanted vaccine was administered in two intramuscular (IM) vaccinations (1 mL per dose), in weaned pigs seropositive to N1-classic antigen at the time of their first vaccination. The efficacy of the adjuvanted four-way NA-RP vaccine was tested against a heterologous N1 (H1N1 virus) challenge infection.

Materials and Methods

Construction of NA-RP Antigens:

The replication defective RNA particles (RPs) contained alphavirus replicon RNA expressing the neuraminidase (NA) gene, were prepared as described in Example 1.

TABLE 3

N1 and N2 Genes Encoded in NA-RP Constructs

| NA phylogenetic cluster | Gene donor strain | GenBank Accession |
|---|---|---|
| N1-classic | A/swine/Iowa/A01410307/2014 (H1N1) | KJ605083 |
| N1-pandemic | A/swine/Minnesota/A01483170/2014 (H1N1) | KP036969 |
| N2-1998 | A/swine/Michigan/A02077465/2015 (H1N2) | KR982634 |
| N2-2002 | A/swine/Illinois/A01475495/2014 (H1N2) | KJ941362 |

Viruses

The challenge viruses were obtained from USDA National Veterinary Services Laboratories. A/swine/Illinois/A01554351/2015 (H1N1) possesses an HA gene of the H1-gamma cluster and a NA gene of the N1-classic cluster. The viruses were propagated in a MDCK cell culture. Confluent cells were infected for approximately 48 hours, until cytopathic effect was evident in over 70% of cell monolayer. At harvest, the supernatant was removed from vessels and clarified by centrifugation before storage of the virus at −0° C. or colder.

Animals:

The weaned piglets were selected from a high health herd based on serology screening to confirm the lack of preexisting HI or NI antibodies to the vaccine and challenge strains. These animals were a mix of male and female, approximately three weeks of age at the time of first vaccination.

Vaccination and Challenge:

The treatment groups are outlined in Table 4 below. A Four-way NA-RP vaccine was formulated at $10^6$ copies each RP/dose, based on an immunofluorescence-based potency assay to quantitate functional RPs. NA-RP antigens were formulated in a stabilizer consisting of 1% swine serum and 5% sucrose. The placebo vaccine consisted of the same stabilizer and no antigen. Vaccines were mixed with Xsolve adjuvant (1:1 v/v, 1 mL dose) prior to administration via IM route to pigs at 3 and 7 weeks of age. Dose levels were back-titrated by IFA test on retained vaccine material following vaccination. Serum samples were collected on the day of the first vaccination, the day of second vaccination, and the day of challenge infection.

At one day prior to the first vaccination all pigs were weighed, pigs in the N1-classic antibody positive groups were injected subcutaneously with a 2 mL/kg dose of N1-classic hyperimmune serum (NI titer of 1:2560 to N1-classic antigen).

TABLE 4

Treatment Groups (n = 10 pigs per group)

| Group | N1-classic antibody status | Vaccine (with Xsolve ®50) | Copy # per dose (1 mL) | Challenge Strain |
|---|---|---|---|---|
| 1 | Positive | 4-way NA-RP | $10^6$ | H1N1 |
| 2 | Negative | 4-way NA-RP | $10^6$ | |
| 3 | Positive | Placebo | — | |
| 4 | Negative | Placebo | — | |

The challenge infection was administered to pigs 3 weeks after the second vaccination. Challenge materials of the H1N1 (H1-gamma-N1-classic) were formulated to the target dose of $10^{6.5}$ TCID50/pig (6 mL volume). The challenge material was administered by the intratracheal route. The challenge virus doses were confirmed by back-titration of retained challenge material. Nasal swabs were collected from all pigs at −1, 1, 3, and 5 days post challenge.

Necropsy was performed 5 days post challenge. Pigs were euthanized by barbiturate overdose at 5 DPC under the supervision of a licensed veterinarian. Lungs were collected and observed in order to document the surface area of each lobe affected by macroscopic lesions, resulting in a comprehensive percent lung lesion score. Bronchoalveolar lavage and nasal swabs were collected from all pigs to measure virus titers. Lung sections were collected for microscopic lesion analysis.

Immune Response Analysis:

IAV-S specific antibodies in pig serum samples were determined by NI test. Sera were heat inactivated for 30-60 minutes at 56° C. The NI test was performed with minor modifications to the method described previously [Sandbulte and Eichelberger, *Methods Mol Biol* 1161: 337-45 (2014)]. Briefly, 2-fold serial dilutions of serum were mixed with the expressed protein antigen at equal volumes on fetuin-coated 96-well plates and incubated overnight at 37° C. Peanut agglutinin horseradish peroxidase conjugate (PNA-HRP) was added for 2 hours at room temperature to bind fetuin molecules stripped of sialic acid. Signal was obtained with TMB substrate, and results read at 650 nm. The mean optical density (OD) of the negative control, which lacked NA antigen, was subtracted from all wells. Then the OD values of test samples were normalized on a scale of 0-100%, where the mean OD of positive control wells (containing NA antigen, but no serum) was defined as 100%. The NI antibody titer was defined as the highest dilution of the sample that inhibited≥50% of neuraminidase activity.

Pathological Examination of Lungs.

Macroscopic lesions observed on the exterior of all lung lobes (well-demarcated purple to plum-colored consolidations) were recorded on grid diagrams of lung anterior and posterior. Comprehensive scores (percent lung lesion) for each pig were calculated according to the number of lesion-affected grids.

Virus Shedding:

Nasal swabs and BAL fluids were 10-fold serially diluted with infecting media [Dulbeco's minimum essential medium (DMEM) supplemented with 0.3% bovine serum albumin, fraction V; 2 mM LGlutamine; 25 μg/mL Gentamycin; 2 μg/mL trypsin IX], and 100 μL of each dilution was added to quadruplicate wells of confluent MDCK cells in a 96-well plate. The plates were incubated at 37° C. with 5% $CO_2$ and observed after 72 hours for the presence of infectious virus by hemagglutination tests of supernatants from each well. IAV-S titers were calculated by the method of Spearman-Kärber and expressed as log 10 TCID50 per mL.

Results

Immune Responses of Pigs Vaccinated with Multivalent NA-RP (See, FIG. 5)

- The pigs passively transferred with N1-classic hyperimmune serum at one day prior to receiving their first vaccination had N1-classic antibody titer of 40-80 at the time of vaccination.
- After two vaccinations of the 4-way NA-RP vaccine with Xsolve 50 the pigs that had been negative to N1-classic antibody induced approximately 3-fold higher NI titer to N1-classic antigen compared to pigs positive to N1-classic antibody at the time of their first vaccination.
- NI titer of pigs in the N1-classic negative/placebo vaccinated group remained seronegative.

Efficacy of 4-Way NA-RP Vaccine Against Challenge Infections, Lung Lesions (See. FIG. 6)

- 4-way NA-RP vaccination was highly efficacious in reducing lung lesions when vaccinated in pigs without N1-classic antibody at the time of their first vaccination. The percent lung lesion was significantly reduced compared to both placebo vaccinated groups.
- The pigs vaccinated in the presence of N1-classic NI titer also had significantly reduced lung lesions compared to both placebo vaccinated groups.

Summary

The 4-way adjuvanted NA-RP vaccination in both N1-classic seropositive and seronegative pigs showed statistically significant protection from the H1N1 virus in terms of lung lesion severity compared to the placebo vaccinated groups. The level of N1-classic titer was reduced, but still positive when pigs were vaccinated in the presence of passively transferred N1-classic antibodies. In addition, the four-way NA-RP vaccine used with the Xsolve adjuvant was surprisingly, highly immunogenic to N1-classic antigen when vaccinated in N1-classic seronegative pigs.

Example 3

Evaluation of Vaccine Efficacy of a 4-Way Neuraminidase (NA) Vaccine Formulated with Dual NA Gene RP Constructs The vaccine in this study consisted of two RNA particle constructs of which each encodes two NA genes of a contemporary IAV-S isolate from the US. One construct has two N1 phylogenetic clusters (N1-classic and N1-pandemic) and the other has two N2 clusters (N2-1998 and N2-2002). The vaccines were formulated at different doses without adjuvant. The objective was to determine the efficacy and immunogenicity of the 4-way NA-RP vaccines formulated at different dose against a H1N2 (N2-2002) virus infection in weaned pigs seronegative to the vaccine fractions.

Materials and Methods

Construction of Dual Gene (DG) NA-RP Antigens and Vaccine Formulation.

Each construct consist of the alphavirus nonstructural protein open reading frame, a subgenomic promoter followed by one NA glycoprotein gene sequence, interstitial sequence, a second subgenomic promoter sequence followed by a second NA glycoprotein gene, and finally the alphavirus 3' untranslated region. The NA DG incorporated into the single RP construct was derived from currently circulating swine influenza virus (SIV) isolates in the US and used to synthesize the NA genes in the plasmid vector pVHV (see Table 5). The plasmid vector pVHV is a derivative of the avirulent human vaccine strain of Venezuelan Equine Encephalitis Virus (TC-83). The completed replicon plasmids were verified for sequence composition and in vitro transcribed into RNA. Each NA replicon RNA was electroporated into Vero cells together with helper RNAs encoding VEE capsid helper and glycoprotein sequence, causing NA replicon RNA to be packaged into RPs. A multivalent immunofluorescence assay was used to quantitate functional N1- and N2-specific RPs and determine the vaccine dose. Test material was serially diluted, added to a Vero cell monolayer in 48 well plates, and incubated at 37° C. for 18-24 hr. Cells were fixed and stained with a primary N1- or N2-antibody followed by a FITC conjugated secondary antibody. Individual antigen-positive cells were counted and the titer was calculated to units of RP/mL.

TABLE 5

N1 and N2 Genes Encoded in NA-RP Constructs

| CONSTRUCT | VIRUS DONOR AND GENE POSITION | NA PHYLOGENETIC CLUSTER (GENBANK ACCESSION) AND GENE POSITION |
|---|---|---|
| N1-DG-RP | 5': A/swine/MN/A01483170/ 2014 (H1N1) 3': A/swine/IA/A01410307/ 2014 (H1N1) | 5'-N1 pandemic (KP036969)-N1classic (KJ605083)-3' |

TABLE 5-continued

N1 and N2 Genes Encoded in NA-RP Constructs

| CONSTRUCT | VIRUS DONOR AND GENE POSITION | NA PHYLOGENETIC CLUSTER (GENBANK ACCESSION) AND GENE POSITION |
|---|---|---|
| N2-DG-RP | 5': A/swine/MI/A02077465/ 2015 (H1N2) 3': A/swine/IL/A01475495/ 2014 (H1N2) | 5'-N21998 (KR982634)-N22002 (KJ941362)-3' |

Vaccines were formulated to have four different dose levels (see, Table 6) in a stabilizer consisting of monosodium glutamate, Sucrose, PVP, Sodium sulfate and HEPES. The placebo vaccine consisted of phosphate buffer saline (PBS) without any RP constructs.

TABLE 6

VACCINE DOSE

| VACCINE | N1-DG-RP | N2-DG-RP | TOTAL |
|---|---|---|---|
| Vaccine 1 | $5.0 \times 10^6$ | $2.5 \times 10^7$ | $3.0 \times 10^7$ |
| Vaccine 2 | $5.6 \times 10^5$ | $2.8 \times 10^6$ | $3.3 \times 10^6$ |
| Vaccine 3 | $2.2 \times 10^5$ | $1.1 \times 10^6$ | $1.3 \times 10^6$ |
| Vaccine 4 | $5.6 \times 10^4$ | $2.8 \times 10^5$ | $3.3 \times 10^5$ |

Virus

Challenge virus, A/swine/IL/A01475495/2014 (H1N2) was obtained from USDA National Veterinary Services Laboratories. The H1N2 isolate possesses an HA gene of the H1-delta 1 cluster and a NA gene of the N2-2002 cluster. Virus was propagated in MDCK cell culture. Confluent cells were infected for approximately 48 hours, until cytopathic effect was evident in over 70% of cell monolayer. At harvest, supernatant was removed from vessels and clarified by centrifugation before storage of the virus at −60° C. or colder.

Animals

Weaned piglets were selected from a high health herd based on serology screening to confirm the lack of preexisting neuraminidase inhibition (NI) antibodies to the vaccine and challenge strain. These animals were a mix of male and female, approximately three weeks of age at the time of first vaccination Vaccination, Challenge and Sample Collection; Pathological Examination of Lungs; Virus Shedding and Neuraminidase Inhibition (NI) Test.

As described above.

Results

Efficacy of 4-Way NA-DG-RP Vaccine Against Challenge Infection

Figure 7:
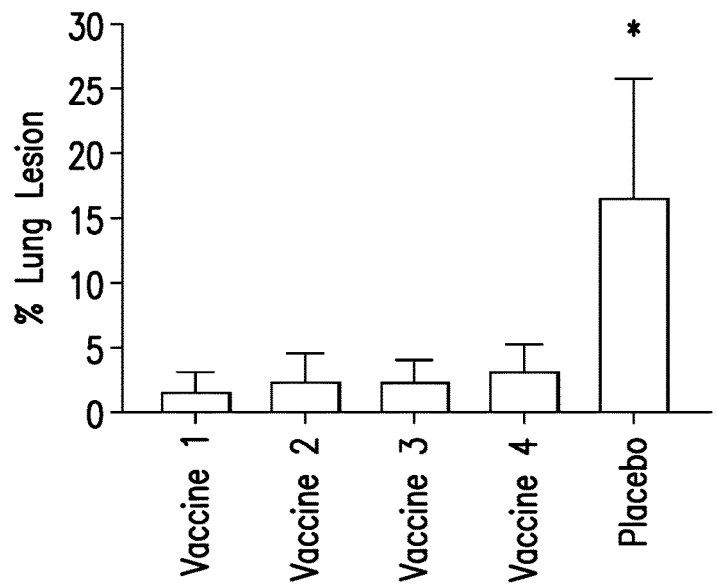
FIG. 7 depicts the percent macroscopic lung lesion at 5 days post infection with H1N2 virus.

Macroscopic lung lesion are shown in FIG. 7. The H1N2 challenge infection resulted in an average of 16.7% lesions on the lungs of placebo control pigs. Vaccinated pigs independent of dose level had an average of 3.3% lung lesions or less and was significantly lower than the placebo group ($p<0.0001$).

Figure 8:
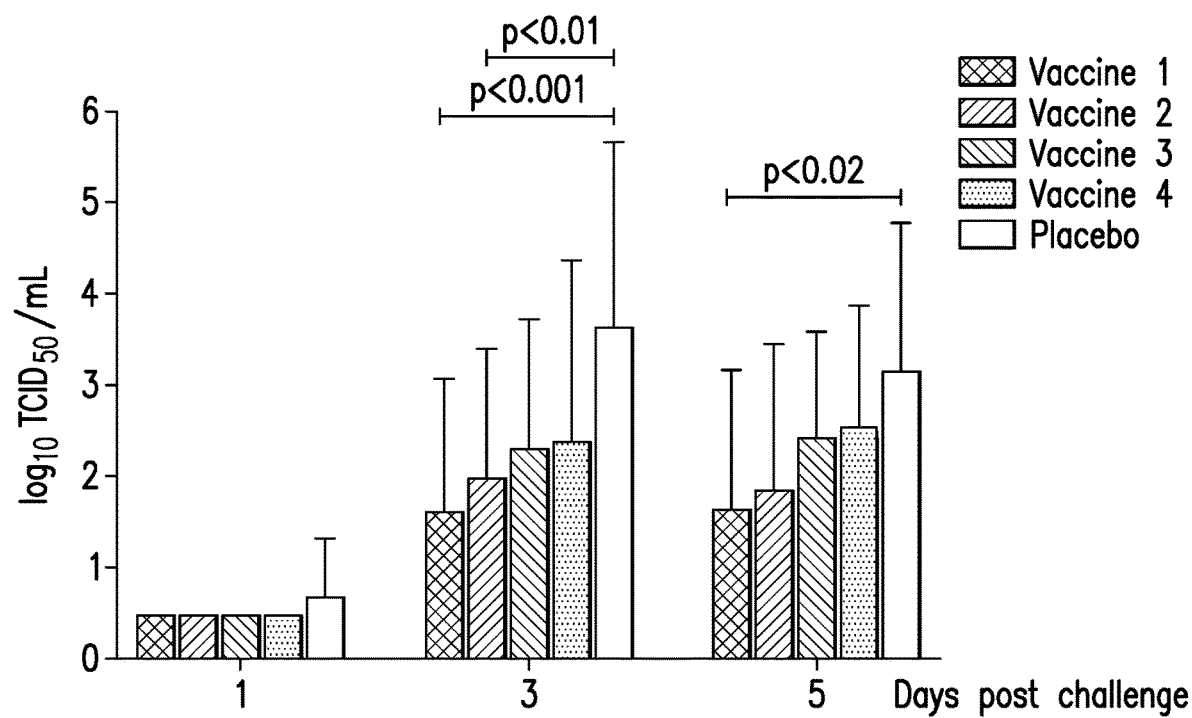
FIG. 8 depicts the nasal shedding post infection with H1N2 virus.

Nasal Shedding (See, FIG. 8)

All pigs were negative to virus shedding at the time point before challenge. None of the vaccinated pigs shed virus at 1 DPC while one pig in the placebo group shed 102.5

TCID50/mL of virus. At 3 DPC, pigs vaccinated with the first two highest doses formulated (Vaccine 1 and 2) had significantly reduce virus in the nasal cavity compared to the placebo pigs. At 5 DPC, only pigs vaccinated with the highest vaccine dose (Vaccine 1) had significantly reduced viral shedding compared to the placebo group.

Immunological Response to Vaccination

Figure 9:
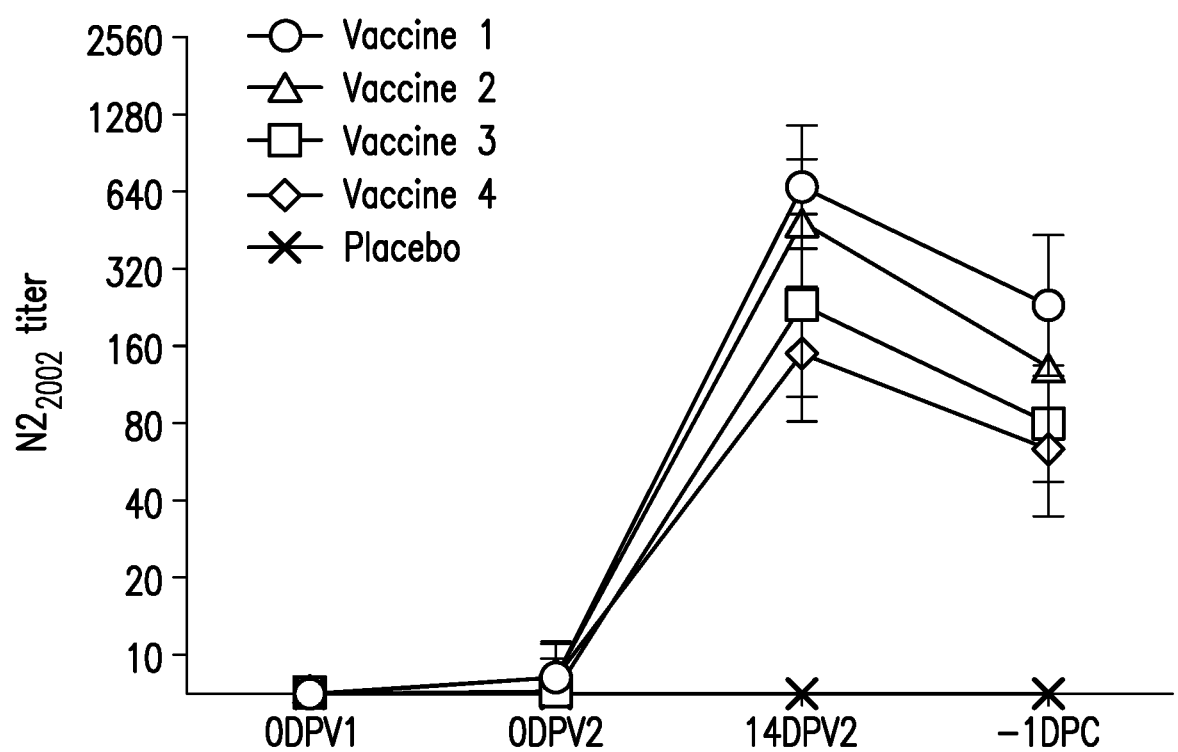
FIG. 9 shows the Neuraminidase Inhibition (NI) titer to $N2_{2002}$ vaccine fraction post vaccination. Note: DPV=days post vaccination

Neuraminidase Inhibition (NI) Titers are shown in FIG. 9. The vaccines formulated with different dose levels induced seroconversion in all vaccinated pigs (N2-2002 titer of >40) and the peaked titer was at 14 days post second vaccination. The average titer detected at 14 DPV2 and −1DPC were not significantly different between the vaccinated groups. However, it appeared that the level of NI titer that is detected trends accordingly to the vaccine dose (higher dose, higher NI titer). Pigs in the placebo group remained seronegative throughout the sample collection time points.

Summary

The H1N2 infection induced high lung lesion scores accompanied by high nasal shedding. Protection in terms of lung lesions was robust regardless of the vaccine dose level tested (the lowest N2-DG-RP dose was $2.5 \times 10^5$ RP/mL). A minimum level $2.5 \times 10^7$ RP/mL is required for the N2-DG-RP construct to significantly reduce shedding following the first 5 days post challenge. All pigs had positive N22002 titer two weeks post second vaccination. The antibody levels detected appears to trend according to the vaccine dose with higher levels observed in pigs receiving a higher vaccine dose.

Example 4

Evaluation of Vaccine Efficacy of a 2-Way Neuraminidase (NA) Vaccine Formulated with Single NA Gene RP Constructs A study was undertaken to determine the efficacy and immunogenicity of five different bivalent adjuvanted NA-RP vaccines, each of which individually encoded a single, different NA gene of a contemporary EU IAV-S isolate. Together these NA genes represent two N1 phylogenetic lineages and three N2 lineages (see, Table 7 below). The adjuvanted vaccine was administered to pigs in two intramuscular (IM) vaccinations at 5 and 8 weeks of age (1 mL per dose; $5 \times 10^6$ RP/dose). The efficacy of the five adjuvanted NA-RP vaccines were individually tested against their corresponding challenge infection as indicated in Table 8 below.

Materials and Methods

Construction of NA-RP Antigens:

The replication defective RNA particles (RPs) contained alphavirus replicon RNA expressing the neuraminidase (NA) gene were prepared as described in Example 1.

Serological Response Experiment:

The treatment groups are outlined in Table 8 below. The NA-RP vaccines were formulated at a dose level $5 \times 10^6$ RP/dose in a volume of 1 mL with adjuvant (XSolve50). The vaccines were administered IM in a 1-mL dose to pigs at 5 and 8 weeks of age. Blood serum samples were collected at 2 weeks post last vaccination to quantify NI antibody titers against the heterologous influenza strain belonging to the respective lineage and homologous NA protein.

Vaccination and Challenge:

Nine pigs per group were immunized twice via intramuscular route at 5 and 8 weeks of age with RP vaccine encoding NA antigens from two different lineages with X-Solve50 adjuvant. Placebo group consisted of seven pigs each and were vaccinated with RP encoding irrelevant antigen with X-solve50. Two weeks post second vaccination, blood samples were collected from all pigs for quantification neuraminidase inhibition (NI) antibody titers against heterologous influenza strain belonging to the respective lineages and average NI titers are presented in the table. After collecting blood samples, pigs were challenged with lineage matched heterologous influenza A strain to one of the vaccine components. Pigs were sacrificed at 3 days post challenge, six lung samples from each pig (one each from each lung lobe) were collected and the viral load was determined using pooled lung homogenates. Values are geometric mean of virus titer (log 10 TCID50/mL). Data is analyzed with Mann-Whitney U test. * Value differ significantly (P<0.05) from respective non-vaccinate group.

TABLE 7

N1 AND N2 GENES ENCODED IN EUROPEAN NA-RP CONSTRUCTS

| NA LINEAGE | GENE DONOR STRAIN | GenBank Accessions[a] |
|---|---|---|
| 2009 pandemic like N1 | A/swine/Italy/179057/2015 (H1N1) | KU323247.1 ALX30323 |
| Eurasian Avian like N1 | A/swine/Italy/28762-3/2013 (H1N1) | KR700532.1 AKJ81669 |
| Gent/1/1984 like N2 | A/swine/Italy/248147-8/2015 (H3N2) | KU323318.1 ALX30429 |
| Italy/4675/2003 like N2 | A/swine/Italy/129452/2015 (H1N2) | KU323215.1 ALX30277 |
| Scotland/410440/ 1994 like N2 (clade 1) | A/swine/England/61470/2013 (H1N2) | KR700793.1 AKJ82042 |
| Scotland/410440/ 1994 like N2 (clade 2) | A/swine/Italy/246087/2014 (H1N2) | KU322976.1 ALX29925 |

[a]Nucleotide and amino acid sequences.

TABLE 8

TREATMENT GROUPS AND VACCINATION CHALLENGE RESULTS

| Treatment Group | Vaccine component | Challenge strain | NI titers against strain matching vaccine component First | NI titers against strain matching vaccine component second | Viral load |
|---|---|---|---|---|---|
| 1a | Pdm N1 & Eurasian Avian N1 | Pandemic like H1N1 | 512 | 128 | 2.01 ± 0.90* |
| 1b | Placebo | | 16 | 16 | 3.64 ± 0.66 |
| 2a | Pdm N1 & Eurasian Avian N1 | Eurasian Avian H1N1 | 256 | 32 | 1.98 ± 086* |
| 2b | Placebo | | 16 | 8 | 3.23 ± 0.53 |
| 3a | Gent1984 N2 & Scot1994 N2 (clade 2) | Gent1984 like H3N2 | 1024 | 256 | 1.63 ± 0.44* |
| 3b | Placebo | | 8 | 32 | 3.33 ± 0.62 |
| 4a | Italy4675 N2 & Scot1994 N2 (clade 1) | Italy4675 N2 like H1N2 | 2048 | 1024 | 1.50 ± 0.00* |
| 4b | Placebo | | 4 | 32 | 3.14 ± 0.62 |
| 5a | Italy4675 N2 & Scot1994 N2 (clade 1) | Scot1994 N2 like H1N2 | 1024 | 1024 | 1.50 ± 0.00* |
| 5b | Placebo | | 4 | 64 | 4.17 ± 0.62 |

Results

The results of this experiment are shown in Table 8. All five of the NA-RP vaccines induced functional NI antibody titers in pigs against heterologous influenza strain belonging to the respective lineage & homologous NA protein.

Lung samples from each pig were collected and the viral load was determined using pooled lung homogenates. The Values provided are the geometric mean of virus titer (log 10 $TCID_{50}$/mL). As is apparent from Table 8, the Values of the vaccinated pigs differ significantly (P<0.05) from their respective non-vaccinate groups, indicating the success of the NA-RP vaccines with respect to viral load upon infection with heterologous virus strains.

Example 5

Phylogenetic Cluster Determinations for U.S.

U.S. Neuraminidase (NA) Cluster Definition

U.S. N1 Cluster:
(1) Amino acid identity within N1 clusters
  a. $N1_{pandemic}$ or N-pandemic is ~97%-100% (average % diversity is 3.12%)
  b. $N1_{classic}$ or N1-classic is ~95%-100% (average % diversity is 4.91%)
(2) Amino acid identity between N1 clusters is ~82% (average % diversity is 18.26%)
U.S. N2 Cluster:
(1) Amino acid identity within N2 clusters
  a. $N2_{1998}$ or N2-1998 is ~94%-100% (average % diversity is 5.94%)
  b. $N2_{2002}$ or N2-2002 is ~94%-100% (average % diversity is 6.37%)
(2) Amino acid identity between N2 clusters is ~88% (average % diversity is 11.84%)
Methods:

Full length non-redundant amino acid sequences of US N1 from H1N1 and H3N1 viruses (about 1,550 sequences total) and US N2 from H1N2 and H3N2 viruses (about 2,700 sequences total) collected from the year 2000 to the present were downloaded from the Influenza Research Database. The percent amino acid identity within and between clusters for US N1 and N2 data were analyzed using version MEGA 7.0.7 [see, Kumar et al., *Bioinformatics* 28:2685-2686 (2012)]. Two sequence alignment using MAFFT version 7.294b [Katoh et al. *Nucleic Acids Res.* 30:3059-3066 (2002); Katoh et al., *Molecular Biology and Evolution* 30:772-780 (2013)] and two separate N1 and N2 maximum likelihood phylogenetic trees were generated in FastTree version 2.1.8 [Price et al., *PLoS ONE*, 5(3) 2010:e9490]. Based upon the N1 and N2 phylogeny, N1 and N2 sequences were assigned to one of the four previously described NA antigenic lineages, $N1_{classic}$, $N1_{pandemic}$, $N2_{1998}$, and $N2_{2002}$ [see, Nelson et al., J Virol. 86(16):8872-8878 (2012); Anderson et al., *Influenza Other Respir Viruses Suppl* 4:42-51 (2013)]. Specific clusters were tagged and the diversity metrics were further calculated using MEGA command line with default settings and a p-distance calculation for the within- and between-cluster diversity with gamma distributed rate variation (alpha of 0.5) and partial deletion set to 95%.

Example 6

Lineage Determinations for Europe

Introduction to EU-NA Part:
Similar to North America, three subtypes of influenza A viruses H1N1, H3N2 and
H1N2, are simultaneously circulating among pigs in European swine populations. However, lineages of HA and NA genes vary significantly within each subtype [see, Kuntz-Simon and Madec Zoonoses *Public Health.*, 56(6-7): 310-325 (2009)]. NA genes of European swine influenza isolates belong to four major and two minor lineages as described by Watson et al., [*J. Virol.*, 89:9920-9931(2015); doi:10.1128/JVI.00840-15]. The major lineages include:
  1. A(H1N1) Pandemic 2009 like N1,
  2. Eurasian Avian-like N1,
  3. A/swine/Gent/1/1984-like N2(Gent/84), and
  4. A/swine/Scotland/410440/1994-like N2 (Scot/94).
Unlike other European major lineages, the NA segments of the Scotland/94 lineage includes four major clades of viruses circulating in European swine population. The minor European influenza NA lineages include:
  1. A/Swine/Italy/4675/2003 like N2 and
  2. Human seasonal like N2.
Description of the Method Used for Analysis of EU NA-N1 and N2 Gene Segments:

Amino acid sequences of full length NA gene of European swine isolates that were collected between 2005 and 2018 were retrieved from the NCBI Influenza Virus Resource [see, ref.32 of Watson et al., *J. Virol.*, 89:9920-9931 (2015); doi:10.1128/JVI.00840-15]. N1 and N2 sequences were aligned using the Muscle (codon) aligner with the default settings provided in MEGA X [Kumar et al., *Molecular Biology and Evolution* 35:1547-1549 (2018)]. The evolutionary history was inferred by using the Maximum Likelihood method based on the Whelan and Goldman model [*Molecular Biology and Evolution* 18:691-699 (2001)]. Bootstrap method with 250 replications was used for phylogeny test. A discrete Gamma distribution was used to model evolutionary rate differences among sites [5 categories (+G, parameter=0.7258)]. The rate variation model allowed for some sites to be evolutionarily invariable {[+I], 38.08% sites}. The analysis involved 244 amino acid sequences. All positions with less than 95% site coverage were eliminated. That is, fewer than 5% alignment gaps, missing data, and ambiguous bases were allowed at any position. There were a total of 469 positions in the final dataset. Evolutionary analyses were conducted in MEGA X [Kumar et al., *Molecular Biology and Evolution* 35:1547-1549 (2018)]. N1 isolates were assigned either Eurasian Avian-N1 like or pandemic 2009-N1 like lineage and N2 isolates were assigned to Scotland/410440/1994-N2 like lineage (e.g., clade 1 or clade 2), Gent/1/1984-N2 like lineage, Italy/4675/2003-N2 like lineage, or Human seasonal-like N2 lineage as described previously [Watson et al., *J. Virol.*, 89:9920-9931 (2015)]. The genetic identity within and between lineages were calculated using MEGA X. Subsequently, a representative strain from each of the above mentioned lineages were selected candidate for the vaccine.

The following target sequences for the respective lineages and/or clades have the resulting range of variability:
  A/swine/Italy/179057/2015(H1N1) sequence with 10% variability
  A/swine/Italy/28762-3/2013(H1N1) sequence with 15% variability A/swine/Italy/248147-8/2015(H3N2) sequence with 10% variability
A/swine/Italy/129452/2015(H1N2) sequence with 10% variability
A/swine/England/61470/2013(H1N2) sequence with 10% variability
A/swine/Italy/246087/2014(H1N2) sequence with 10% variability.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

It is further to be understood that all base sizes or amino acid sizes, and all molecular weight or molecular mass values, given for nucleic acids or polypeptides are approximate, and are provided for description.

We claim:

1. A vaccine for administration to a porcine comprising a first alphavirus RNA replicon particle that encodes a first swine influenza A virus (IAV-S) neuraminidase (NA) or an antigenic fragment thereof and a second alphavirus RNA replicon particle that encodes a second IAV-S NA or an antigenic fragment thereof, and a pharmaceutically acceptable carrier; with the proviso that the vaccine neither comprises an IAV-S hemagglutinin (HA) or an antigenic fragment thereof, nor a nucleotide sequence that encodes the IAV-S HA or the antigenic fragment thereof; and wherein the first NA and the second NA comprise amino acid sequences that have 98% identity or less.

2. The vaccine of claim 1, wherein the first NA originates from an IAV-S from a first phylogenetic cluster and the second NA originates from an IAV-S from a second phylogenetic cluster, wherein the first phylogenetic cluster and the second phylogenetic cluster are different; and wherein the first phylogenetic cluster and the second phylogenetic cluster are individually selected from the group consisting of a N1-classic cluster, a N1-pandemic cluster, N2-1998 cluster, and a N2-2002 cluster.

3. The vaccine of claim 2, wherein the first phylogenetic cluster is selected from the group consisting of the N1-classic cluster and the N1-pandemic cluster and wherein the second phylogenetic cluster is selected from the group consisting of the N2-1998 cluster and the N2-2002 cluster.

4. The vaccine of claim 3, wherein the first phylogenetic cluster is the N1-classic cluster and the second phylogenetic cluster is the N2-2002 cluster.

5. The vaccine of claim 2, further comprising a third alphavirus RNA replicon particle that encodes a third NA or an antigenic fragment thereof; wherein the third NA originates from an IAV-S from a third phylogenetic cluster; and wherein the third phylogenetic cluster is different from the first phylogenetic cluster and the second phylogenetic cluster.

6. The vaccine of claim 5, further comprising a fourth alphavirus RNA replicon particle that encodes a fourth NA or an antigenic fragment thereof; wherein the fourth NA originates from an IAV-S from a fourth phylogenetic cluster; and wherein the fourth phylogenetic cluster is different from the first phylogenetic cluster, the second phylogenetic cluster, and the third phylogenetic cluster.

7. The vaccine of claim 6, wherein the first phylogenetic cluster is a N1-classic cluster, the second phylogenetic cluster is a N2-2002 cluster, the third phylogenetic cluster is a N1-pandemic cluster, and the fourth phylogenetic cluster is a N2-1998 cluster.

8. A vaccine comprising an alphavirus RNA replicon particle that encodes two or more swine influenza A virus (IAV-S) neuraminidases (NAs) or antigenic fragments thereof, and a pharmaceutically acceptable carrier; with the proviso that the vaccine neither comprises an IAV-S hemagglutinin (HA) or an antigenic fragment thereof, nor a nucleotide sequence that encodes the IAV-S HA or the antigenic fragment thereof; and wherein the first NA and the second NA comprise amino acid sequences that have 98% amino acid identity or less.

9. The vaccine of claim 8, wherein the first NA originates from an IAV-S from a first phylogenetic cluster and a second NA originates from an IAV-S from a second phylogenetic cluster; wherein the first phylogenetic cluster and the second phylogenetic cluster are different; and wherein the first phylogenetic cluster and the second phylogenetic cluster are individually selected from the group consisting of a N1-classic cluster, a N1-pandemic cluster, a N2-1998 cluster, and a N2-2002 cluster.

10. The vaccine of claim 9, wherein the first phylogenetic cluster is a N2-1998 cluster and the second phylogenetic cluster is a N2-2002 cluster.

11. The vaccine of claim 9, wherein the first phylogenetic cluster is a N1-classic cluster and the second phylogenetic cluster is a N1-pandemic cluster.

12. The vaccine of claim 11, further comprising a second alphavirus RNA replicon particle that encodes a third NA or antigenic fragment thereof and a fourth NA or antigenic fragment thereof; wherein the third NA originates from an IAV-S from a N2-1998 cluster and the fourth NA originates from an IAV-S from a N2-2002 cluster.

13. The vaccine of claim 1, wherein both the first alphavirus RNA replicon particle and the second alphavirus RNA replicon particle are Venezuelan Equine Encephalitis Virus (VEEV) alphavirus RNA replicon particles.

14. A vaccine to aid in the prevention of disease in a porcine due to influenza virus comprising a Venezuelan Equine Encephalitis Virus (VEEV) alphavirus RNA replicon particle that encodes two or more swine influenza A virus (IAV-S) neuraminidases (NAs) or antigenic fragments thereof, and a pharmaceutically acceptable carrier; with the proviso that the vaccine neither comprises an IAV-S HA or an antigenic fragment thereof, nor a nucleotide sequence that encodes the IAV-S HA or the antigenic fragment thereof.

15. The vaccine of claim 8, which is a nonadjuvanted vaccine.

16. The vaccine of claim 8, that comprises an adjuvant selected from the group consisting of an oil-in-water emulsion with 2.5-50% (v/v) mineral oil, and a biodegradable oil mixed with an oil-in-water emulsion with 2.5-50% (v/v) mineral oil.

17. The vaccine of claim 16, wherein the biodegradable oil is dl-α-tocopheryl acetate and the mineral oil is a liquid paraffin.

18. A method of immunizing a porcine against a swine influenza A virus comprising administering to the porcine an immunologically effective amount of the vaccine of claim 16.

19. A method of immunizing a porcine against a swine influenza A virus comprising administering to the porcine an immunologically effective amount of the vaccine of claim 14.

20. The vaccine of claim 8, wherein the alphavirus RNA replicon particle is a Venezuelan Equine Encephalitis Virus (VEEV) alphavirus RNA replicon particle.

* * * * *

SEQUENCE LISTING

```
<160> NUMBER OF SEQ ID NOS: 27

<210> SEQ ID NO 1
<211> LENGTH: 1407
<212> TYPE: DNA
<213> ORGANISM: Artificial Sequence
<220> FEATURE:
<223> OTHER INFORMATION: Codon optimized swine influenza virus sequence

<400> SEQUENCE: 1
atgaatacta atcaaaggat cattaccatt gggacagtct gcatgattgt cggtatcatc        60
tctcttttgc ttcagattgg aaacattgtc tcactttgga ttagccattc aattcagacc       120
ggatgggaga atcacactga gatgtgcaat caaagtgtca ttacttatgt caataacact       180
tgggtgaacc ggacttatgt gaacattagc aatatcaaga ttgcaactat tcaagatgtg       240
actagtatca ttttggccgg aaattctagt ctttgcccgg tgtcagggtg ggctgtctac       300
agcaaagaca atagcattag gattggatca aaaggggaca ttttcgtcat tagagagcct       360
ttcatctcat gctcacaatt ggagtgccgg accttctttc tgacccaagg ggcattgctg       420
aatgacaaac attcaaatgg taccgtcaag gacaggagtc cttatagaac cctgatgagc       480
tgccctatcg gtgaggcccc ttcgccatac aactcacggt tcgaatctgt cgcatggtca       540
gcatctgctt gtcatgatgg aatgggatgg cttacaatcg ggatcagtgg accggataat       600
ggtgctgtcg cagtcttgaa atacaacgga atcattacag atacaatcaa atcttggagg       660
aacaagattc ttagaactca agaatcagag tgtgtctgta tgaacggatc atgttttaca       720
gtcttgacag atggcccaag caatggacaa gcctcttaca aaatctttaa ggtggaaaaa       780
ggaaagatta tcaagtcgat tgagctggat gcccccaatt accactatga agaatgctct       840
tgttatccag atactggcaa agtcatgtgt gtctgccggg acaattggca cgcctcaaac       900
cggccatggg tgtcgttcaa tcagaatctt gactatcaaa ttggatacat tgctctgga       960 gtctttggtg ataaccctag atccaatgat gggaagggca attgtggccc ggtccttttct      1020 aatggagcaa atggagtgaa aggtttctca tatcggtatg gaaatggtgt gtggattggt      1080
cggaccaagt caatcaactc tcggtcgggt tttgagatga tttgggatcc gaatggatgg      1140
actgagacag attcatcatt ctcgatgaag caggacatta tcgctcttaa tgattggtct      1200
ggatactcgg gatcttttgt ccaacatccg gagcttactg gtatgaattg cattaggcct      1260
tgtttctggg tggaattgat cagagggcaa cccaaggaaa gcactatctg ggctagcggt      1320
tccagcatct cattctgtgg cgtcaattcg gaaaccgctt cctggtcttg gccagacgga      1380
gctgatctgc cattcaccat tgacaag                                          1407

<210> SEQ ID NO 2
<211> LENGTH: 469
<212> TYPE: PRT
<213> ORGANISM: swine influenza virus
```

```
<400> SEQUENCE: 2

Met Asn Thr Asn Gln Arg Ile Ile Thr Ile Gly Thr Val Cys Met Ile
1               5                   10                  15

Val Gly Ile Ile Ser Leu Leu Leu Gln Ile Gly Asn Ile Val Ser Leu
            20                  25                  30

Trp Ile Ser His Ser Ile Gln Thr Gly Trp Glu Asn His Thr Glu Met
        35                  40                  45

Cys Asn Gln Ser Val Ile Thr Tyr Val Asn Asn Thr Trp Val Asn Arg
    50                  55                  60

Thr Tyr Val Asn Ile Ser Asn Ile Lys Ile Ala Thr Ile Gln Asp Val
65                  70                  75                  80

Thr Ser Ile Ile Leu Ala Gly Asn Ser Ser Leu Cys Pro Val Ser Gly
                85                  90                  95

Trp Ala Val Tyr Ser Lys Asp Asn Ser Ile Arg Ile Gly Ser Lys Gly
            100                 105                 110

Asp Ile Phe Val Ile Arg Glu Pro Phe Ile Ser Cys Ser Gln Leu Glu
        115                 120                 125

Cys Arg Thr Phe Phe Leu Thr Gln Gly Ala Leu Leu Asn Asp Lys His
    130                 135                 140

Ser Asn Gly Thr Val Lys Asp Arg Ser Pro Tyr Arg Thr Leu Met Ser
145                 150                 155                 160

Cys Pro Ile Gly Glu Ala Pro Ser Pro Tyr Asn Ser Arg Phe Glu Ser
                165                 170                 175

Val Ala Trp Ser Ala Ser Ala Cys His Asp Gly Met Gly Trp Leu Thr
            180                 185                 190

Ile Gly Ile Ser Gly Pro Asp Asn Gly Ala Val Ala Val Leu Lys Tyr
        195                 200                 205

Asn Gly Ile Ile Thr Asp Thr Ile Lys Ser Trp Arg Asn Lys Ile Leu
    210                 215                 220

Arg Thr Gln Glu Ser Glu Cys Val Cys Met Asn Gly Ser Cys Phe Thr
225                 230                 235                 240

Val Leu Thr Asp Gly Pro Ser Asn Gly Gln Ala Ser Tyr Lys Ile Phe
                245                 250                 255

Lys Val Glu Lys Gly Lys Ile Ile Lys Ser Ile Glu Leu Asp Ala Pro
            260                 265                 270

Asn Tyr His Tyr Glu Glu Cys Ser Cys Tyr Pro Asp Thr Gly Lys Val
        275                 280                 285

Met Cys Val Cys Arg Asp Asn Trp His Ala Ser Asn Arg Pro Trp Val
    290                 295                 300

Ser Phe Asn Gln Asn Leu Asp Tyr Gln Ile Gly Tyr Ile Cys Ser Gly
305                 310                 315                 320

Val Phe Gly Asp Asn Pro Arg Ser Asn Asp Gly Lys Gly Asn Cys Gly
                325                 330                 335

Pro Val Leu Ser Asn Gly Ala Asn Gly Val Lys Gly Phe Ser Tyr Arg
            340                 345                 350

Tyr Gly Asn Gly Val Trp Ile Gly Arg Thr Lys Ser Ile Asn Ser Arg
        355                 360                 365

Ser Gly Phe Glu Met Ile Trp Asp Pro Asn Gly Trp Thr Glu Thr Asp
    370                 375                 380

Ser Ser Phe Ser Met Lys Gln Asp Ile Ile Ala Leu Asn Asp Trp Ser
385                 390                 395                 400

Gly Tyr Ser Gly Ser Phe Val Gln His Pro Glu Leu Thr Gly Met Asn
                405                 410                 415
```

```
Cys Ile Arg Pro Cys Phe Trp Val Glu Leu Ile Arg Gly Gln Pro Lys
            420                 425                 430

Glu Ser Thr Ile Trp Ala Ser Gly Ser Ser Ile Ser Phe Cys Gly Val
            435                 440                 445

Asn Ser Glu Thr Ala Ser Trp Ser Trp Pro Asp Gly Ala Asp Leu Pro
            450                 455                 460

Phe Thr Ile Asp Lys
465

<210> SEQ ID NO 3
<211> LENGTH: 1407
<212> TYPE: DNA
<213> ORGANISM: Artificial Sequence
<220> FEATURE:
<223> OTHER INFORMATION: Codon optimized swine influenza virus sequence

<400> SEQUENCE: 3
atgaatccta accaaaagat cattaccatt ggttcggtct gtatgacaat tggaatggct        60
aacctgatcc ttcaaattgg aaacattatc tcaatctggg tcagccactc aattcaaatt       120
ggaaatcaat cgcagattga acatgcaac caaagcgtca ttacttacga aaacaacact        180
tgggtgaacc agacctacgt gaacatcagc aacaccaact cgctgctgg acagtccgtg        240 gtttccgtga actggcggg caactcctct ctctgccctg tgagcggatg ggctatctac        300
tccaaagaca actcagtcag aatcggttcc aaggggatg tgtttgtcat aagggaacca        360
ttcatctcat gctctcccct gaatgcaga accttcttct tgactcaagg ggccttgcta        420
aatgacaaac attccaacgg aaccattaaa gacaggagcc catatcggac cctgatgagc        480
tgtcctatcg gtgaagtccc ctcgccatac aactcaagat tgagtcagt cgcttggtca        540 gcatccgctt gtcatgatgg catcaattgg ctcaccattg gaatttctgg cccagacagt        600
ggggcagtgg ctgtgctgaa gtacaatggc attataacag acactatcaa gtcgtggagg        660
aacaacatat tgagaactca agagtctgaa tgtgcatgtg tgaatggttc ttgctttacc        720
atcatgaccg atggaccatc cgatggacag gcctcctaca gatcttcag aatcgaaaag        780 ggaaagatcg tcaaatcagt cgaaatgaat gcccctaact accactatga ggaatgctcc        840
tgttatcctg attcctccga aatcacgtgc gtgtgcaggg ataactggca tggctccaat        900
cggccgtggg tgtcttttca ccagaatctg aatatcaga tcggatacat ttgctccggg        960
gtgttcggag acaatccgcg ccctaatgat aagacaggct cgtgtggtcc agtctcgtct       1020
aacggagcca acggagtcaa aggattttca ttcaaatacg gcaatggagt gtggataggg       1080
agaactaaga gcatttcctc aagaaaaggt ttcgagatga tttgggatcc aatggatgg       1140 actgggactg caacaagtt ctcaatcaag caagacatcg tgggaatcag cgagtggtca       1200
ggatatagcg ggtcctttgt gcagcacccc gaactgaccg ggctggattg tattagacct       1260
tgcttctggg tcgaactcat cagagggcga cccgaagaga cacaatctg actagcggg        1320 agcagcatct cctttgtgg tgtgaactcg gacactgtgg gttggtcttg ccagacggt        1380 gctgagttgc cttttaccat tgacaag                                          1407

<210> SEQ ID NO 4
<211> LENGTH: 469
<212> TYPE: PRT
<213> ORGANISM: swine influenza virus

<400> SEQUENCE: 4
```

```
Met Asn Pro Asn Gln Lys Ile Ile Thr Ile Gly Ser Val Cys Met Thr
1               5                   10                  15
Ile Gly Met Ala Asn Leu Ile Leu Gln Ile Gly Asn Ile Ile Ser Ile
                20                  25                  30
Trp Val Ser His Ser Ile Gln Ile Gly Asn Gln Ser Gln Ile Glu Thr
                35                  40                  45
Cys Asn Gln Ser Val Ile Thr Tyr Glu Asn Asn Thr Trp Val Asn Gln
    50                  55                  60
Thr Tyr Val Asn Ile Ser Asn Thr Asn Phe Ala Ala Gly Gln Ser Val
65                  70                  75                  80
Val Ser Val Lys Leu Ala Gly Asn Ser Ser Leu Cys Pro Val Ser Gly
                85                  90                  95
Trp Ala Ile Tyr Ser Lys Asp Asn Ser Val Arg Ile Gly Ser Lys Gly
                100                 105                 110
Asp Val Phe Val Ile Arg Glu Pro Phe Ile Ser Cys Ser Pro Leu Glu
                115                 120                 125
Cys Arg Thr Phe Phe Leu Thr Gln Gly Ala Leu Leu Asn Asp Lys His
130                 135                 140
Ser Asn Gly Thr Ile Lys Asp Arg Ser Pro Tyr Arg Thr Leu Met Ser
145                 150                 155                 160
Cys Pro Ile Gly Glu Val Pro Ser Pro Tyr Asn Ser Arg Phe Glu Ser
                165                 170                 175
Val Ala Trp Ser Ala Ser Ala Cys His Asp Gly Ile Asn Trp Leu Thr
                180                 185                 190
Ile Gly Ile Ser Gly Pro Asp Ser Gly Ala Val Ala Val Leu Lys Tyr
                195                 200                 205
Asn Gly Ile Ile Thr Asp Thr Ile Lys Ser Trp Arg Asn Asn Ile Leu
                210                 215                 220
Arg Thr Gln Glu Ser Glu Cys Ala Cys Val Asn Gly Ser Cys Phe Thr
225                 230                 235                 240
Ile Met Thr Asp Gly Pro Ser Asp Gly Gln Ala Ser Tyr Lys Ile Phe
                245                 250                 255
Arg Ile Glu Lys Gly Lys Ile Val Lys Ser Val Glu Met Asn Ala Pro
                260                 265                 270
Asn Tyr His Tyr Glu Glu Cys Ser Cys Tyr Pro Asp Ser Ser Glu Ile
                275                 280                 285
Thr Cys Val Cys Arg Asp Asn Trp His Gly Ser Asn Arg Pro Trp Val
290                 295                 300
Ser Phe Asn Gln Asn Leu Glu Tyr Gln Ile Gly Tyr Ile Cys Ser Gly
305                 310                 315                 320
Val Phe Gly Asp Asn Pro Arg Pro Asn Asp Lys Thr Gly Ser Cys Gly
                325                 330                 335
Pro Val Ser Ser Asn Gly Ala Asn Gly Val Lys Gly Phe Ser Phe Lys
                340                 345                 350
Tyr Gly Asn Gly Val Trp Ile Gly Arg Thr Lys Ser Ile Ser Ser Arg
                355                 360                 365
Lys Gly Phe Glu Met Ile Trp Asp Pro Asn Gly Trp Thr Gly Thr Asp
370                 375                 380
Asn Lys Phe Ser Ile Lys Gln Asp Ile Val Gly Ile Ser Glu Trp Ser
385                 390                 395                 400
Gly Tyr Ser Gly Ser Phe Val Gln His Pro Glu Leu Thr Gly Leu Asp
                405                 410                 415
Cys Ile Arg Pro Cys Phe Trp Val Glu Leu Ile Arg Gly Arg Pro Glu
```

Glu Asn Thr Ile Trp Thr Ser Gly Ser Ser Ile Ser Phe Cys Gly Val
            420                 425                 430

Asn Ser Asp Thr Val Gly Trp Ser Trp Pro Asp Gly Ala Glu Leu Pro
            435                 440                 445

Phe Thr Ile Asp Lys
465

<210> SEQ ID NO 5
<211> LENGTH: 1407
<212> TYPE: DNA
<213> ORGANISM: Artificial Sequence
<220> FEATURE:
<223> OTHER INFORMATION: Codon optimized swine influenza virus sequence

<400> SEQUENCE: 5

```
atgaatccaa accaaaagat aatcacaatt ggctctgttt ctctcactat tgccacaatg      60
tgcctcctta tgcaaattgc atcctgatt actaatgtca cattgcactc caatcagtac     120
gaatgcaact acccccaaa caaccagtg atactgtgtg aaccaactat catcaaaaga      180
acattactg agattgtgta tctggccaac accaccatag agaaggaaat ctgccccaag     240
ctggcagaat acagaaactg gtcgaagccg caatgtaaaa ttacagggtt tgcaccttt     300
tccaaggaca attcgattag ctttctgcg ggtggcgaca tttgggtaac gagagaacct    360
tatgtgtcat gcgatcctga taagtgttac cagtttgccc ttggacaagg aacaacgctc    420
aacaacagac attcaaacga caccgtgcat gataggaccc cttatcgaac cctattgatg    480
aatgagttgg gtattccatt ccatttgggg accaaacaag tgtgcatcgc atggtccagc    540
tcatcctgcc atgatggacg ggcttggctt catgtctgta ttactgggca tgacaacaat    600
gcaactgcca gcatcattta caatggacgc cttgtcgata gtattggttc atggtccaaa    660
agaatcctca ggacccagga gtcggaatgc gtgtgcatca atggaacttg taccgtggtc    720
atgactgatg gtccgcttc aggaatagct gacactaaaa tcctgttcat tgaagagggg    780
aaaatcgtgc acattagccc actgctgggg tccgctcagc acgtggagga gtgctcctgc    840
tatccccgat acccaggtgt cagatgcatc tgtagagaca ctggaaaagg ctccaacaga    900
cctgtcgtgg atattaatgt gaaggattat agcattgtgt cctcctacgt gtgctccgga    960
ctggtgggag acacccccag aaaagacgac agatccagct ccagcaattg tctgaatcct   1020
aacaacgaga aggggagca tggagtgaaa ggctgggcct tgatgatgg aaatgacgtg     1080
tggatgggga ggacaatcaa cgagacatta cgctcaggtt atgaaacctt caagtcatt    1140
gaaggctggt ccaaacctaa ttccaaattg cagataaatc gccaagtcat tgttgaaaga   1200
gatgataggt ccggttattc tggaattttc tctgtcgaag aaagagctg tatcaatcgg   1260
tgttttacg tggagctgat cagaggaagg aaacaggaaa ctgcagtgtg gtggacgtca    1320
aattccattg tggtgttttg tggcacctca ggtacctatg aaccggctc atggcctgat   1380
ggggcggaca tcaatctcat gcctgtg                                       1407
```

<210> SEQ ID NO 6
<211> LENGTH: 469
<212> TYPE: PRT
<213> ORGANISM: swine influenza virus

<400> SEQUENCE: 6

Met Asn Pro Asn Gln Lys Ile Ile Thr Ile Gly Ser Val Ser Leu Thr
1               5                   10                  15

```
Ile Ala Thr Met Cys Leu Leu Met Gln Ile Ala Ile Leu Ile Thr Asn
            20                  25                  30

Val Thr Leu His Ser Asn Gln Tyr Glu Cys Asn Tyr Pro Asn Asn
        35                  40                  45

Gln Val Ile Leu Cys Glu Pro Thr Ile Ile Lys Arg Asn Ile Thr Glu
 50                  55                  60

Ile Val Tyr Leu Ala Asn Thr Thr Ile Glu Lys Glu Ile Cys Pro Lys
65                  70                  75                  80

Leu Ala Glu Tyr Arg Asn Trp Ser Lys Pro Gln Cys Lys Ile Thr Gly
                85                  90                  95

Phe Ala Pro Phe Ser Lys Asp Asn Ser Ile Arg Leu Ser Ala Gly Gly
                100                 105                 110

Asp Ile Trp Val Thr Arg Glu Pro Tyr Val Ser Cys Asp Pro Asp Lys
            115                 120                 125

Cys Tyr Gln Phe Ala Leu Gly Gln Gly Thr Thr Leu Asn Asn Arg His
    130                 135                 140

Ser Asn Asp Thr Val His Asp Arg Thr Pro Tyr Arg Thr Leu Leu Met
145                 150                 155                 160

Asn Glu Leu Gly Ile Pro Phe His Leu Gly Thr Lys Gln Val Cys Ile
                165                 170                 175

Ala Trp Ser Ser Ser Ser Cys His Asp Gly Arg Ala Trp Leu His Val
                180                 185                 190

Cys Ile Thr Gly His Asp Asn Asn Ala Thr Ala Ser Ile Ile Tyr Asn
            195                 200                 205

Gly Arg Leu Val Asp Ser Ile Gly Ser Trp Ser Lys Arg Ile Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Ile Ala Asp Thr Lys Ile Leu Phe
                245                 250                 255

Ile Glu Glu Gly Lys Ile Val His Ile Ser Pro Leu Leu Gly Ser Ala
                260                 265                 270

Gln His Val Glu Glu Cys Ser Cys Tyr Pro Arg Tyr Pro Gly Val Arg
            275                 280                 285

Cys Ile Cys Arg Asp Asn Trp Lys Gly Ser Asn Arg Pro Val Val Asp
    290                 295                 300

Ile Asn Val Lys Asp Tyr Ser Ile Val Ser Ser Tyr Val Cys Ser Gly
305                 310                 315                 320

Leu Val Gly Asp Thr Pro Arg Lys Asp Asp Arg Ser Ser Ser Ser Asn
                325                 330                 335

Cys Leu Asn Pro Asn Asn Glu Lys Gly Glu His Gly Val Lys Gly Trp
                340                 345                 350

Ala Phe Asp Asp Gly Asn Asp Val Trp Met Gly Arg Thr Ile Asn Glu
            355                 360                 365

Thr Leu Arg Ser Gly Tyr Glu Thr Phe Lys Val Ile Glu Gly Trp Ser
    370                 375                 380

Lys Pro Asn Ser Lys Leu Gln Ile Asn Arg Gln Val Ile Val Glu Arg
385                 390                 395                 400

Asp Asp Arg Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Lys Gln
            420                 425                 430
```

```
Glu Thr Ala Val Trp Trp Thr Ser Asn Ser Ile Val Val Phe Cys Gly
            435                 440                 445

Thr Ser Gly Thr Tyr Gly Thr Gly Ser Trp Pro Asp Gly Ala Asp Ile
        450                 455                 460

Asn Leu Met Pro Val
465

<210> SEQ ID NO 7
<211> LENGTH: 1407
<212> TYPE: DNA
<213> ORGANISM: Artificial Sequence
<220> FEATURE:
<223> OTHER INFORMATION: Codon optimized swine influenza virus sequence

<400> SEQUENCE: 7
atgaatccaa atcaaaagat cattactatt ggatcagtct cactcatcat tgccacaatt        60
tgtttcctta tgcaaattgc aatccttgtc actactgtca cattgcattt caagcagcat       120
gactacaact cccccccaaa caaccaagct actctgtgtg aaccaacaat cattgaacgg       180
aaaacaactg aaattgtgta tcttactaac accaccattg agaagaagt ctgccccaaa        240 cttgcagagt accggaactg gtcaaagcct aatgtaaca ttactggatt tgcaccattt        300
tcgaaagaca attctattcg gttgtctgct ggtgggaca tctgggtgac tagggaacct        360
tatgtgtcat gcgatcctga caagtgttac aatttgccc ttggacaggg tacaactctt       420
aacaacggac attcgaataa cacagtccat gataggaccc cgtatcggac ccttcttatg       480
aatgagcttg gtgtcccttt tcatcttgga accagacaag tgtgcatggc ttggtctagc       540
tcatcttgtc acgatgggaa agcatggctg catgtctgtg tcactggaaa tgataacaat       600
gctactgcta gcttcatcta caatggtagg cttgtggatt ctattggttc gtggtcgaaa       660
aacattctcc ggacccaaga gtcagaatgc gtctgtatca tggaacatg tactgtcgtc        720 atgactgatg gatccgctag tggaaaagca gataccaaaa tcttgttcgt cgaagagggg        780
aagatcgtcc atatcagcac tctgttggga tctgcacagc acgtcgagga tgctcctgt        840 tatcctaggt ttccggggagt ccggtgtgtc tgccgggaca actggaaagg atctaataga       900
cccatcgtcg acatcaatgt caagaattac agcattgtct cttcgtatgt ctgcagtgga       960
cttgtcggtg atactcccag agagagcgac tcagtctcct catcttattg cttggatccg      1020
aacaatgaga agggtggtca tgggtgaaa gggtgggcct tgatgatgg taatgacgtg        1080 tggatgggaa gaacaatcaa cgagactttg cgcttgggat atgaaacctt caaagtcatt       1140
gaaggctggt ccacagctaa ctccaagtca cagacaaata gacaagtgat tgtcaaaaa        1200 ggagacaggt caggatattc tgggattttc tcagtcgagg gaaagaactg catcaatagg      1260
tgcttctatg tggagttgat tagggacgg aaagaggaga caaagtctg gtggaccagt        1320 aactcaattg tcgtgttttg tggcacctca gggacttatg gtactggctc ttggccggat      1380
ggtgctgaca tcaatctcat gccaatt                                          1407

<210> SEQ ID NO 8
<211> LENGTH: 469
<212> TYPE: PRT
<213> ORGANISM: swine influenza virus

<400> SEQUENCE: 8

Met Asn Pro Asn Gln Lys Ile Ile Thr Ile Gly Ser Val Ser Leu Ile
1               5                   10                  15

Ile Ala Thr Ile Cys Phe Leu Met Gln Ile Ala Ile Leu Val Thr Thr
```

```
                20              25              30
Val Thr Leu His Phe Lys Gln His Asp Tyr Asn Ser Pro Pro Asn Asn
            35              40              45
Gln Ala Thr Leu Cys Glu Pro Thr Ile Ile Glu Arg Lys Thr Thr Glu
            50              55              60
Ile Val Tyr Leu Thr Asn Thr Thr Ile Glu Lys Val Cys Pro Lys
65              70              75              80
Leu Ala Glu Tyr Arg Asn Trp Ser Lys Pro Gln Cys Asn Ile Thr Gly
                85              90              95
Phe Ala Pro Phe Ser Lys Asp Asn Ser Ile Arg Leu Ser Ala Gly Gly
            100             105             110
Asp Ile Trp Val Thr Arg Glu Pro Tyr Val Ser Cys Asp Pro Asp Lys
            115             120             125
Cys Tyr Gln Phe Ala Leu Gly Gln Gly Thr Thr Leu Asn Asn Gly His
            130             135             140
Ser Asn Asn Thr Val His Asp Arg Thr Pro Tyr Arg Thr Leu Leu Met
145             150             155             160
Asn Glu Leu Gly Val Pro Phe His Leu Gly Thr Arg Gln Val Cys Met
                165             170             175
Ala Trp Ser Ser Ser Cys His Asp Gly Lys Ala Trp Leu His Val
            180             185             190
Cys Val Thr Gly Asn Asp Asn Ala Thr Ala Ser Phe Ile Tyr Asn
            195             200             205
Gly Arg Leu Val Asp Ser Ile Gly Ser Trp Ser Lys Asn Ile Leu Arg
            210             215             220
Thr Gln Glu Ser Glu Cys Val Cys Ile Asn Gly Thr Cys Thr Val Val
225             230             235             240
Met Thr Asp Gly Ser Ala Ser Gly Lys Ala Asp Thr Lys Ile Leu Phe
                245             250             255
Val Glu Glu Gly Lys Ile Val His Ile Ser Thr Leu Leu Gly Ser Ala
            260             265             270
Gln His Val Glu Glu Cys Ser Cys Tyr Pro Arg Phe Pro Gly Val Arg
            275             280             285
Cys Val Cys Arg Asp Asn Trp Lys Gly Ser Asn Arg Pro Ile Val Asp
            290             295             300
Ile Asn Val Lys Asn Tyr Ser Ile Val Ser Ser Tyr Val Cys Ser Gly
305             310             315             320
Leu Val Gly Asp Thr Pro Arg Glu Ser Asp Ser Val Ser Ser Ser Tyr
                325             330             335
Cys Leu Asp Pro Asn Asn Glu Lys Gly Gly His Gly Val Lys Gly Trp
            340             345             350
Ala Phe Asp Asp Gly Asn Asp Val Trp Met Gly Arg Thr Ile Asn Glu
            355             360             365
Thr Leu Arg Leu Gly Tyr Glu Thr Phe Lys Val Ile Glu Gly Trp Ser
            370             375             380
Thr Ala Asn Ser Lys Ser Gln Thr Asn Arg Gln Val Ile Val Glu Lys
385             390             395             400
Gly Asp Arg Ser Gly Tyr Ser Gly Ile Phe Ser Val Glu Gly Lys Asn
                405             410             415
Cys Ile Asn Arg Cys Phe Tyr Val Glu Leu Ile Arg Gly Arg Lys Glu
            420             425             430
Glu Thr Lys Val Trp Trp Thr Ser Asn Ser Ile Val Val Phe Cys Gly
            435             440             445
```

```
Thr Ser Gly Thr Tyr Gly Thr Gly Ser Trp Pro Asp Gly Ala Asp Ile
    450                 455                 460

Asn Leu Met Pro Ile
465

<210> SEQ ID NO 9
<211> LENGTH: 13
<212> TYPE: DNA
<213> ORGANISM: Artificial Sequence
<220> FEATURE:
<223> OTHER INFORMATION: 5' flanking sequence

<400> SEQUENCE: 9
ggcgcgccgc acc                                                          13

<210> SEQ ID NO 10
<211> LENGTH: 8
<212> TYPE: DNA
<213> ORGANISM: Artificial Sequence
<220> FEATURE:
<223> OTHER INFORMATION: 3' flanking sequence

<400> SEQUENCE: 10 ttaattaa                                                                 8

<210> SEQ ID NO 11
<211> LENGTH: 1410
<212> TYPE: DNA
<213> ORGANISM: swine influenza virus

<400> SEQUENCE: 11
atgaatccaa accaaaagat aataaccatt ggttcggtct gtatgacaat tggaatggct     60
aacttaatat tacaaattgg aaacataatc tcaatatgga ttagccactc aattcaactt    120
gggaatcaaa gtcagattga aacatgcaat caaagcgtca ttacttatga aaacaacact    180
tgggtaaatc agacatatgt taacatcagc aacaccaact ttgctgctgg acagtcagtg    240
gtttccgcga aattagcggg caattcctcc ctctgccctg ttagtggatg ggctatatac    300
agtaaagaca acagtgtaag aatcggttcc aagggggatg tgtttgtcat aagggaacca    360
ttcatatcat gctccccctt agaatgcaga accttcttct tgactcaagg ggccttgcta    420
aatgacaaac attccaatgg aaccattaaa gataggagcc catatcgaac cctgatgagc    480
tgtcctattg gtgaagttcc ctctccatac aactcaagat ttgagtcggt cgcttggtca    540
gcaagtgctt gtcacgatgg catcaattgg ctaacaatcg gaatttctgg cccagacagt    600
ggggcagtgg ctgtattaaa gtacaatggc ataataacag acactatcaa gagttggaaa    660
aacaatatat tgagaacaca agagtctgaa tgtgcatgtg taaatggttc ttgctttacc    720
ataatgaccg atggaccaag tgatggacag gcctcataca agatcttcag aatagaaaag    780
ggaaagatag tcaaatcagt cgaaatgaat gcccctaatt atcactatga ggaatgctcc    840
tgttatcctg attctagtga aatcacatgt gtgtgcaggg ataactggca tggctcgaat    900
cgaccgtggg tgtctttcaa ccagaatctg gaatatcaga taggatacat atgcagtggg    960
attttcggag acaatccacg ccctaatgat aagacaggca gttgtggtcc agtatcgtct   1020
aatggagcaa atggagtaaa aggattttca ttcaaatatg gcaatggtgt ttggataggg   1080
agaactaaaa gcattagttc aagaaaaggt tttgagatga tttgggatcc aaatggatgg   1140
actgggacag acaaaaactt ctcaataaag caagatatca taggaataaa tgagtggtca   1200
```

-continued

```
ggatacagcg ggagttttgt tcagcatcca gaactaacag ggctgaattg tataagacct    1260
tgcttctggg ttgaactaat cagagggcga cccaaagaga acacaatctg gactagcggg    1320
agcagcatat cctttttgtgg tgtaaacagt gacactgtgg gttggtcttg gccagacggt    1380
gctgagttgc catttaccat tgacaagtaa                                      1410
```

<210> SEQ ID NO 12
<211> LENGTH: 469
<212> TYPE: PRT
<213> ORGANISM: swine influenza virus

<400> SEQUENCE: 12

```
Met Asn Pro Asn Gln Lys Ile Ile Thr Ile Gly Ser Val Cys Met Thr
1               5                   10                  15

Ile Gly Met Ala Asn Leu Ile Leu Gln Ile Gly Asn Ile Ile Ser Ile
            20                  25                  30

Trp Ile Ser His Ser Ile Gln Leu Gly Asn Gln Ser Gln Ile Glu Thr
        35                  40                  45

Cys Asn Gln Ser Val Ile Thr Tyr Glu Asn Asn Thr Trp Val Asn Gln
    50                  55                  60

Thr Tyr Val Asn Ile Ser Asn Thr Asn Phe Ala Ala Gly Gln Ser Val
65                  70                  75                  80

Val Ser Ala Lys Leu Ala Gly Asn Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser Pro Leu Glu
        115                 120                 125

Cys Arg Thr Phe Phe Leu Thr Gln Gly Ala Leu Leu Asn Asp Lys His
    130                 135                 140

Ser Asn Gly Thr Ile Lys Asp Arg Ser Pro Tyr Arg Thr Leu Met Ser
145                 150                 155                 160

Cys Pro Ile Gly Glu Val Pro Ser Pro Tyr Asn Ser Arg Phe Glu Ser
                165                 170                 175

Val Ala Trp Ser Ala Ser Ala Cys His Asp Gly Ile Asn Trp Leu Thr
            180                 185                 190

Ile Gly Ile Ser Gly Pro Asp Ser Gly Ala Val Ala Val Leu Lys Tyr
        195                 200                 205

Asn Gly Ile Ile Thr Asp Thr Ile Lys Ser Trp Lys Asn Asn Ile Leu
    210                 215                 220

Arg Thr Gln Glu Ser Glu Cys Ala Cys Val Asn Gly Ser Cys Phe Thr
225                 230                 235                 240

Ile Met Thr Asp Gly Pro Ser Asp Gly Gln Ala Ser Tyr Lys Ile Phe
                245                 250                 255

Arg Ile Glu Lys Gly Lys Ile Val Lys Ser Val Glu Met Asn Ala Pro
            260                 265                 270

Asn Tyr His Tyr Glu Glu Cys Ser Cys Tyr Pro Asp Ser Ser Glu Ile
        275                 280                 285

Thr Cys Val Cys Arg Asp Asn Trp His Gly Ser Asn Arg Pro Trp Val
    290                 295                 300

Ser Phe Asn Gln Asn Leu Glu Tyr Gln Ile Gly Tyr Ile Cys Ser Gly
305                 310                 315                 320

Ile Phe Gly Asp Asn Pro Arg Pro Asn Asp Lys Thr Gly Ser Cys Gly
                325                 330                 335
```

```
Pro Val Ser Ser Asn Gly Ala Asn Gly Val Lys Gly Phe Ser Phe Lys
            340                 345                 350

Tyr Gly Asn Gly Val Trp Ile Gly Arg Thr Lys Ser Ile Ser Ser Arg
        355                 360                 365

Lys Gly Phe Glu Met Ile Trp Asp Pro Asn Gly Trp Thr Gly Thr Asp
    370                 375                 380

Lys Asn Phe Ser Ile Lys Gln Asp Ile Ile Gly Ile Asn Glu Trp Ser
385                 390                 395                 400

Gly Tyr Ser Gly Ser Phe Val Gln His Pro Glu Leu Thr Gly Leu Asn
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465

<210> SEQ ID NO 13
<211> LENGTH: 1408
<212> TYPE: DNA
<213> ORGANISM: swine influenza virus

<400> SEQUENCE: 13
atgaacccaa atcagaagat aataatcatt agttcaatct gtatgacaaa tggaattgct      60
agcttgatat acaaattgg gaacataata tcaatatgga ttagccattc aattcaaatt     120
gagaacccaa accagaccga ccatgcaatc aaagcgttat tatttacgaa acaacacat     180 gggtaaatca acgtatgtt aacatcagca acaataattt tgttgttgaa cagacagtgg     240
tttcaatgaa attagcgggc agttcttctc tctgccctgt tagtggatgg gctatataca     300
gtaaagataa cagtgtaaga atcggttcca aaggggatgt gtttgtcata agagagccat     360
tcatctcatg ctcccatttg gaatgtgaa ccttcttctt aactcaaggg gccctactga     420
atgataaaca ttctaatgga accgttaaag acagaagccc ctatcgaacc ctgatgagct     480
gtcctattgg tgaagtcccc tctccataca actcaaaatt tgagtcagtt gcttggtcag     540
caagtgcttg ccatgatggc accagttggt tgacaattgg gatttctggt ccagacaatg     600
gagcagtggc tgtgttgaaa tacaatgaca taataacaga cactatcaag agttggaaaa     660
acaacatatt gagaacacaa gaatctgaat gtgcatgttt gaatggttct tgctttactg     720
taatgaccga tggaccaagt aatgggcagg cctcatacaa gatcttcaaa atagaaaagg     780
ggaaagtagt caaatcagtc gagttgaatg ctcctaatta tcactatgag gaatgttcct     840
gttatcctga ttctggtgaa atcatatgtg tatgcaggga caattggcat ggctcgaatc     900
gaccatgggt gtcttctcaat cagaatctgg agtatcagat aggatacata tgcagtgggg     960
ttctcggaga caatccgcgc cctaatgata gaacaggcag ttgtggtcca gtatcatctc    1020
atggagcaaa tggggtaaaa gggttttcgt ttaaatacgg caatggaatt tggataggga    1080
gaactaaaag cactattaca aggagtggtt ttgagatgat ttgggaccca aacggatgga    1140
ctggaacaga caataatttc tcagtgaagc aagatatcgt aggaataact aactggtcag    1200
gatacgcggg agttttgtcc aacatccaga attaaccgga ttggattgta ttagaccttg    1260
cttctgggtt gaactaatca gagggagacc caaagagaac acaatctgga ctagcggaag    1320
```

```
cagcatatcc ttttgtggtg taaatagtga cactgtgggt tggtcttggc cagacggtgc    1380
tgagttgcca tttaccattg acaagtaa                                      1408
```

<210> SEQ ID NO 14
<211> LENGTH: 469
<212> TYPE: PRT
<213> ORGANISM: swine influenza virus

<400> SEQUENCE: 14

```
Met Asn Pro Asn Gln Lys Ile Ile Ile Ser Ser Ile Cys Met Thr
1               5                   10                  15

Asn Gly Ile Ala Ser Leu Ile Leu Gln Ile Gly Asn Ile Ile Ser Ile
            20                  25                  30

Trp Ile Ser His Ser Ile Gln Ile Glu Asn Pro Asn Gln Thr Glu Pro
            35                  40                  45

Cys Asn Gln Ser Val Ile Ile Tyr Glu Asn Asn Thr Trp Val Asn Gln
        50                  55                  60

Thr Tyr Val Asn Ile Ser Asn Asn Asn Phe Val Val Glu Gln Thr Val
65                  70                  75                  80

Val Ser Met Lys Leu Ala Gly Ser Ser Leu Cys Pro Val Ser Gly
                85                  90                  95

Trp Ala Ile Tyr Ser Lys Asp Asn Ser Val Arg Ile Gly Ser Lys Gly
            100                 105                 110

Asp Val Phe Val Ile Arg Glu Pro Phe Ile Ser Cys Ser His Leu Glu
        115                 120                 125

Cys Arg Thr Phe Phe Leu Thr Gln Gly Ala Leu Leu Asn Asp Lys His
130                 135                 140

Ser Asn Gly Thr Val Lys Asp Arg Ser Pro Tyr Arg Thr Leu Met Ser
145                 150                 155                 160

Cys Pro Ile Gly Glu Val Pro Ser Pro Tyr Asn Ser Lys Phe Glu Ser
                165                 170                 175

Val Ala Trp Ser Ala Ser Ala Cys His Asp Gly Thr Ser Trp Leu Thr
            180                 185                 190

Ile Gly Ile Ser Gly Pro Asp Asn Gly Ala Val Ala Val Leu Lys Tyr
        195                 200                 205

Asn Asp Ile Ile Thr Asp Thr Ile Lys Ser Trp Lys Asn Asn Ile Leu
210                 215                 220

Arg Thr Gln Glu Ser Glu Cys Ala Cys Leu Asn Gly Ser Cys Phe Thr
225                 230                 235                 240

Val Met Thr Asp Gly Pro Ser Asn Gly Gln Ala Ser Tyr Lys Ile Phe
                245                 250                 255

Lys Ile Glu Lys Gly Lys Val Val Lys Ser Val Glu Leu Asn Ala Pro
            260                 265                 270

Asn Tyr His Tyr Glu Glu Cys Ser Cys Tyr Pro Asp Ser Gly Glu Ile
        275                 280                 285

Ile Cys Val Cys Arg Asp Asn Trp His Gly Ser Asn Arg Pro Trp Val
290                 295                 300

Ser Phe Asn Gln Asn Leu Glu Tyr Gln Ile Gly Tyr Ile Cys Ser Gly
305                 310                 315                 320

Val Leu Gly Asp Asn Pro Arg Pro Asn Asp Arg Thr Gly Ser Cys Gly
                325                 330                 335

Pro Val Ser Ser His Gly Ala Asn Gly Val Lys Gly Phe Ser Phe Lys
            340                 345                 350

Tyr Gly Asn Gly Ile Trp Ile Gly Arg Thr Lys Ser Thr Ile Thr Arg
```

-continued

```
        355                 360                 365

Ser Gly Phe Glu Met Ile Trp Asp Pro Asn Gly Trp Thr Gly Thr Asp
    370                 375                 380

Asn Asn Phe Ser Val Lys Gln Asp Ile Val Gly Ile Thr Asn Trp Ser
385                 390                 395                 400

Gly Tyr Ser Gly Ser Phe Val Gln His Pro Glu Leu Thr Gly Leu Asp
                405                 410                 415

Cys Ile Arg Pro Cys Phe Trp Val Glu Leu Ile Arg Gly Arg Pro Lys
            420                 425                 430

Glu Asn Thr Ile Trp Thr Ser Gly Ser Ser Ile Ser Phe Cys Gly Val
        435                 440                 445

Asn Ser Asp Thr Val Gly Trp Ser Trp Pro Asp Gly Ala Glu Leu Pro
    450                 455                 460

Phe Thr Ile Asp Lys
465

<210> SEQ ID NO 15
<211> LENGTH: 1410
<212> TYPE: DNA
<213> ORGANISM: swine influenza virus

<400> SEQUENCE: 15
atgaatccaa atcaaaagat aataacaatt ggttctgttt ctctcactat tacaacaatg      60
tgcctcttct tgcagattgc catcctagta actactataa cattgcattt caagcaatat     120
gaatgcgatt cccctgcaaa caaccaagta ataccgtgtg aaccaataat aatagaaaaa     180
aacataacaa aaatagtgta tttgaccaat accaccatag agaaagaggt atgcccaaaa     240
ttaggggaat acaggaattg gtcaaaacca caatgcaaga tcacaggatt tgcacctttt     300
tctaaggaca attcaattcg gctctctgcg ggtggggcca tttgggtcac gagagaacct     360
tatgtgtcat gcgaccctaa caagtgttat caatttgcat taggacaggg aaccacatta     420
gataacagac attcaaatga cacaatacat gatagaaccc cttttagaac cctgttgatg     480
agtgaattag gtgttccatt tcatttggga accagacaag tatgcatagc atggtccagt     540
tcaagttgtc acgatgggaa agcttggttg catgtttgtg tcactgggca tgataaaaat     600
gcaactgcta gtttcattta tgacggaaag cttgtagaca gcatcagttc atggtccaaa     660
aacatactcc ggactcagga atcagaatgt gtttgtatcg atggaatctg tacagtggtg     720
atgactgatg gaagtgcttc agggaaagct gatactaaga tactatttat tgaaaaaggg     780
aagatcattc atattagtcc attgttggga agtgctcagc atgtagaaga atgttcctgt     840
taccctagat accctgatgt caggtgtatt tgcagggata actggaaagg ttcaaatagg     900
cccatcgtag acataagaat gaaaaattat agcattggtt ccagttatat gtgctcagga     960
cttgttggcg acacacccag gaacaatgat gggtctagta atagcaattg tcggaatccc    1020
aataatgaaa gaggaaatca tggagtgaaa ggttgggcct ttgatgatgg aaatgacaca    1080
tggatgggaa gaactatcag caaggactca cgcttaggtt acgaaacctt caaagttgtt    1140
ggtggttggt cccaacccaa ttccaaatcc cagataaata gacaagttat tgttgacagc    1200
gataatagat caggttactc tggtattttc tctgttgagg ggaaagattg cattaatagg    1260
tgtttttatg tggaactaat aagaggaagg agacaggaaa ctagagtgtg gtggacttcg    1320
aacagtattg ttgtgttctg tggcacttct ggcacctatg ggtcaggctc atggcccgat    1380
ggagcaaaca tcaatttcat gcctgtataa                                     1410
```

<210> SEQ ID NO 16
<211> LENGTH: 469
<212> TYPE: PRT
<213> ORGANISM: swine influenza virus

<400> SEQUENCE: 16

Met Asn P

```
Gln Pro Asn Ser Lys Ser Gln Ile Asn Arg Gln Val Ile Val Asp Ser
385                 390                 395                 400

Asp Asn Arg Ser Gly Tyr Ser Gly Ile Phe Ser Val Glu Gly Lys Asp
                405                 410                 415

Cys Ile Asn Arg Cys Phe Tyr Val Glu Leu Ile Arg Gly Arg Arg Gln
            420                 425                 430

Glu Thr Arg Val Trp Trp Thr Ser Asn Ser Ile Val Val Phe Cys Gly
        435                 440                 445

Thr Ser Gly Thr Tyr Gly Ser Gly Ser Trp Pro Asp Gly Ala Asn Ile
    450                 455                 460

Asn Phe Met Pro Val
465
```

<210> SEQ ID NO 17
<211> LENGTH: 1410
<212> TYPE: DNA
<213> ORGANISM: swine influenza virus

<400> SEQUENCE: 17

```
atgaattcaa atcaaaagat aataacaatt ggctctgttt ctctcactat tgccacacta     60
tgcctcctta tgcaaattgc tatcatggta actactgtaa catttcattt caagcagtat    120
gaatacaact cccccccgaa caaccaagta atgttgtgtg aaccaacgat aattgaaaga    180
aacataacag agacagtgta catgaccaac accaccatag tgaaagaaat atgccccaaa    240
ctagcggaat acagaaattg gtcaaaaccg caatgcaaaa ttacaggatt tgcacctttt    300
tcaaaggaca actcaattcg gctttccgct ggtggggaca tctgggtgac aagagaacct    360
tatgtgtcat gcgatcctaa caagtgttat caatttgccc ttgggcaggg aacaacgtta    420
aacaacaggc attcaaatga cacagtacat gatagaaccc cttaccgaac cctgttgatg    480
aatgaattgg gtgttccatt tcatttagga accaagcagg tttgcatagc ttggtccagt    540
tcaagttgtc atgatggaaa agcatggttg catgtttgtg taactgggca tgatgaaaat    600
gcaactgcca gtttcattta caacgagaga cttgtagata gtattggttc atggtccaag    660
aaaatcctca gaacccagga gtcggaatgc gtttgcataa atgggacttg tacagtggtg    720
atgacagatg ggagtgcttc aggtagagct gatactaaaa tactattcat tgaggagggg    780
aaaatcgttc atgttagcca actgacagga agtgctcagc atgtagagga gtgctcctgt    840
tatccccggt atcctggtgt cagatgtgtt tgcagagata attggaaagg ctccaatagg    900
cccattgtag atataaatgt aaaggatcat agcattgttt ccagttatgt gtgctcagga    960
cttgtcggag acacacccag aaaaaacgac agctctagca gtagtaactg cctgaatcct   1020
aacaatgaag aagggggtca tggggtgaaa ggctgggcct ttgatgatga aaatgacttg   1080
tggatgggaa gaacgatcag cgaaaagtta cgattaggtt atgaaacctt caaggtcatt   1140
gaaggctggt ccaagcctaa ttccaaattg cagataaata ggcaagtaat agttgacaaa   1200
gataatagat ccggttattc tggtattttc tctgttgaaa gtaaaagttg catcaatcgg   1260
tgcttttatg tggagttgat aagaggaagg aaacaggaaa atgaagtatg gtggacctca   1320
aacagcattg ttgtattttg tggcacctca ggtacatatg gaacaggctc atggcctgat   1380
ggggcagaca tcaatctcat gcctatatga                                     1410
```

<210> SEQ ID NO 18
<211> LENGTH: 469
<212> TYPE: PRT

<213> ORGANISM: swine influenza virus

<400> SEQUENCE: 18

Met Asn Ser Asn Gln Lys Ile Ile Thr Ile Gly Ser Val Ser Leu Thr
1               5                   10                  15

Ile Ala Thr Leu Cys Leu Leu Met Gln Ile Ala Ile Met Val Thr Thr
            20                  25                  30

Val Thr Phe His Phe Lys Gln Tyr Glu Tyr Asn Ser Pro Pro Asn Asn
        35                  40                  45

Gln Val Met Leu Cys Glu Pro Thr Ile Ile Glu Arg Asn Ile Thr Glu
    50                  55                  60

Thr Val Tyr Met Thr Asn Thr Thr Ile Val Lys Glu Ile Cys Pro Lys
65                  70                  75                  80

Leu Ala Glu Tyr Arg Asn Trp Ser Lys Pro Gln Cys Lys Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Asn Lys
        115                 120                 125

Cys Tyr Gln Phe Ala Leu Gly Gln Gly Thr Thr Leu Asn Asn Arg His
130                 135                 140

Ser Asn Asp Thr Val His Asp Arg Thr Pro Tyr Arg Thr Leu Leu Met
145                 150                 155                 160

Asn Glu Leu Gly Val Pro Phe His Leu Gly Thr Lys Gln Val Cys Ile
                165                 170                 175

Ala Trp Ser Ser Ser Cys His Asp Gly Lys Ala Trp Leu His Val
            180                 185                 190

Cys Val Thr Gly His Asp Glu Asn Ala Thr Ala Ser Phe Ile Tyr Asn
        195                 200                 205

Glu Arg Leu Val Asp Ser Ile Gly Ser Trp Ser Lys Lys Ile Leu Arg
210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Lys Ile Leu Phe
                245                 250                 255

Ile Glu Glu Gly Lys Ile Val His Val Ser Gln Leu Thr Gly Ser Ala
            260                 265                 270

Gln His Val Glu Glu Cys Ser Cys Tyr Pro Arg Tyr Pro Gly Val Arg
        275                 280                 285

Cys Val Cys Arg Asp Asn Trp Lys Gly Ser Asn Arg Pro Ile Val Asp
290                 295                 300

Ile Asn Val Lys Asp His Ser Ile Val Ser Ser Tyr Val Cys Ser Gly
305                 310                 315                 320

Leu Val Gly Asp Thr Pro Arg Lys Asn Asp Ser Ser Ser Ser Ser Asn
                325                 330                 335

Cys Leu Asn Pro Asn Asn Glu Glu Gly Gly His Gly Val Lys Gly Trp
            340                 345                 350

Ala Phe Asp Asp Glu Asn Asp Leu Trp Met Gly Arg Thr Ile Ser Glu
        355                 360                 365

Lys Leu Arg Leu Gly Tyr Glu Thr Phe Lys Val Ile Glu Gly Trp Ser
370                 375                 380

Lys Pro Asn Ser Lys Leu Gln Ile Asn Arg Gln Val Ile Val Asp Lys
385                 390                 395                 400

-continued

```
Asp Asn Arg Ser Gly Tyr Ser Gly Ile Phe Ser Val Glu Ser Lys Ser
            405                 410                 415

Cys Ile Asn Arg Cys Phe Tyr Val Glu Leu Ile Arg Gly Arg Lys Gln
            420                 425                 430

Glu Asn Glu Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asp Ile
    450                 455                 460

Asn Leu Met Pro Ile
465
```

<210> SEQ ID NO 19
<211> LENGTH: 1410
<212> TYPE: DNA
<213> ORGANISM: swine influenza virus

<400> SEQUENCE: 19
```
atgaatccaa atcagaagat aataacaatt ggctctgttt ctctcgtcat tgcaacatta      60
tgcttcttaa tgcagatggc catcctaata actactgtaa aattacattt caaacaatat     120
gagtgcggct tccctgcgaa caaccaagta ataacatgtg agccaacagt aatagaaagg     180
aacacaacag agatagtgta cttaactaac accaccatag agaaagaaac atgccacaaa     240
acagtggaat acaggaattg gtcaaagcct caatgcaaaa taacaggctt tgcacctttt     300
tccaaggaca attcaattcg actttctgct ggtggggaca tatgggtgac gagggaacct     360
tacgtgtcat gcgagcctgg caaatgttat cagtttgcac tcgggcaagg gaccacacta     420
gacaataaac attcaaacga tacaatacat gacagaaccc cctatcgaac tctattgatg     480
aatgaattgg gtgtcccatt tcatttaggg acaagacaag tgtgtattgc atggtccagc     540
tcaagttgtt atgatgggaa agcatggttg catgtctgta tcactggaca tgataaaaat     600
gcaactgcca gtttcattta cgatggtaga cttgtagata gcattggttc atggtctaaa     660
aatatactta gaacccagga atcagaatgc gtttgcatca atggggtctg tacagtagta     720
atgactgatg gaagtgcttc gggaagagct gatactaaaa tactattcat tgaagaaggg     780
aaaattgttc atattagccc attagcgggg agtgcacagc atgtggagga gtgctcctgt     840
tatccccgat atcctggcgt aaggtgtatc tgcagagaca actggaaagg ctctaacaga     900
cccgttgtgg atataaatat agaagattat agcattgatt ccagttatgt gtgttcaggg     960
cttgttggcg acacacccag aatcaatgac ggatccagta gtagctactg ccgtgatcct    1020
aacaacgaaa aggaaatca cggagtgaag ggctgggctt ttgacgatgg aaatgatgtg    1080
tggatgggaa gaacgatcaa cgaagattca cgctcaggtt atgaaacatt caaagtcatt    1140
ggtggttggt ccactcctaa ttccaaattg cagataaata ggcaagtaat agttgatagc    1200
aacaataggt caggttattc tggtgttttc tccgttgaag gcaaaagctg catcaataga    1260
tgtttctacg tggagttgat aagaggaaga aggtcagaag cgcgagtatg gtggacctca    1320
aacagtattg ttgtattttg tggcacttca ggtacctatg gaacaggctc atggcctgat    1380
ggagcagaca tcaacctcat gcctatatga                                     1410
```

<210> SEQ ID NO 20
<211> LENGTH: 469
<212> TYPE: PRT
<213> ORGANISM: swine influenza virus

<400> SEQUENCE: 20

-continued

```
Met Asn Pro Asn Gln Lys Ile Ile Thr Ile Gly Ser Val Ser Leu Val
1               5                   10                  15

Ile Ala Thr Leu Cys Phe Leu Met Gln Met Ala Ile Leu Ile Thr Thr
            20                  25                  30

Val Lys Leu His Phe Lys Gln Tyr Glu Cys Gly Phe Pro Ala Asn Asn
            35                  40                  45

Gln Val Ile Thr Cys Glu Pro Thr Val Ile Glu Arg Asn Thr Thr Glu
            50                  55                  60

Ile Val Tyr Leu Thr Asn Thr Thr Ile Glu Lys Glu Thr Cys His Lys
65                  70                  75                  80

Thr Val Glu Tyr Arg Asn Trp Ser Lys Pro Gln Cys Lys Ile Thr Gly
                85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Glu Pro Gly Lys
            115                 120                 125

Cys Tyr Gln Phe Ala Leu Gly Gln Gly Thr Thr Leu Asp Asn Lys His
            130                 135                 140

Ser Asn Asp Thr Ile His Asp Arg Thr Pro Tyr Arg Thr Leu Leu Met
145                 150                 155                 160

Asn Glu Leu Gly Val Pro Phe His Leu Gly Thr Arg Gln Val Cys Ile
                165                 170                 175

Ala Trp Ser Ser Ser Ser Cys Tyr Asp Gly Lys Ala Trp Leu His Val
            180                 185                 190

Cys Ile Thr Gly His Asp Lys Asn Ala Thr Ala Ser Phe Ile Tyr Asp
            195                 200                 205

Gly Arg Leu Val Asp Ser Ile Gly Ser Trp Ser Lys Asn Ile Leu Arg
            210                 215                 220

Thr Gln Glu Ser Glu Cys Val Cys Ile Asn Gly Val Cys Thr Val Val
225                 230                 235                 240

Met Thr Asp Gly Ser Ala Ser Gly Arg Ala Asp Thr Lys Ile Leu Phe
                245                 250                 255

Ile Glu Glu Gly Lys Ile Val His Ile Ser Pro Leu Ala Gly Ser Ala
            260                 265                 270

Gln His Val Glu Glu Cys Ser Cys Tyr Pro Arg Tyr Pro Gly Val Arg
            275                 280                 285

Cys Ile Cys Arg Asp Asn Trp Lys Gly Ser Asn Arg Pro Val Val Asp
            290                 295                 300

Ile Asn Ile Glu Asp Tyr Ser Ile Asp Ser Ser Tyr Val Cys Ser Gly
305                 310                 315                 320

Leu Val Gly Asp Thr Pro Arg Ile Asn Asp Gly Ser Ser Ser Ser Tyr
                325                 330                 335

Cys Arg Asp Pro Asn Asn Glu Lys Gly Asn His Gly Val Lys Gly Trp
            340                 345                 350

Ala Phe Asp Asp Gly Asn Asp Val Trp Met Gly Arg Thr Ile Asn Glu
            355                 360                 365

Asp Ser Arg Ser Gly Tyr Glu Thr Phe Lys Val Ile Gly Gly Trp Ser
            370                 375                 380

Thr Pro Asn Ser Lys Leu Gln Ile Asn Arg Gln Val Ile Val Asp Ser
385                 390                 395                 400

Asn Asn Arg Ser Gly Tyr Ser Gly Val Phe Ser Val Glu Gly Lys Ser
                405                 410                 415

Cys Ile Asn Arg Cys Phe Tyr Val Glu Leu Ile Arg Gly Arg Arg Ser
```

```
              420                 425                 430
Glu Ala Arg Val Trp Trp Thr Ser Asn Ser Ile Val Val Phe Cys Gly
            435                 440                 445

Thr Ser Gly Thr Tyr Gly Thr Gly Ser Trp Pro Asp Gly Ala Asp Ile
    450                 455                 460

Asn Leu Met Pro Ile
465

<210> SEQ ID NO 21
<211> LENGTH: 1410
<212> TYPE: DNA
<213> ORGANISM: swine influenza virus

<400> SEQUENCE: 21
atgaatccaa accagaaaat aataacgatc ggttctgtct ccttgatcat tgcaacaatg      60
tgcttttca tgcaagttgc cattctggta actactgtaa cattgcattt caggcagtgc     120
gaatgcaact cctccgcaac caaccaaata atgccatgta aaccaacaaa aatagagaga     180
aacataactg aaattgtgta cttaaccaat accaccataa aaacagaggt atgccccaaa     240
ctagtgaaat acagggattg ggcaaaacca aatgtagaa tcacagggtt tgcacctttt     300
tccaaggaca attcgattcg gctttctgcc ggtgggggcca tttgggtaac gagagaaccc     360
tatgtatcat gcgatcttag caagtgttac cagtttgcgc tcggacaggg gactacacta     420
gacaacagac attcaaatga cacaatacat gatagaactc cttatcggac cctattgatg     480
aatgaattgg gtgttccatt tcatttagga accaggcaag tgtgtatagc ttggtccagt     540
tcaagttgtc acgatggaaa agcatggctg catgtttgtg tcactgggta tgataaaaat     600
gctactgcta gcctcattta tgacggaagg cttgtggaca gcatcggttc atggtcccaa     660
aacatcctcc ggacccagga atcggaatgt gtttgtataa atggtacttg cacagtggta     720
atgactgatg ggagtgcttc aggaaaaagct gataccagaa tactatttat tgaagaaggg     780
aagattattc acattagtcc attgacagga agtgcacagc atgttgaaga gtgttcttgt     840
tatcctcgat accccggtgt aagatgtgtt tgtagagaca actggaaggg ctctaacaga     900
cccgtcgtgg atataaatgt aaaagattat aaaattaact ccagttatgt atgctcaggc     960
cttgttggcg atacacccag aaacaacgat agatctagca atagcaactg ccaaaatcct    1020
aacaaccaga gagggaatca tggagtgaag ggctgggcct tgacgatgg aaatgacata    1080
tggatgggaa gaaccatcag caatgattca cgtttaggtt atgaaacttt caaagttatt    1140
ggtggttggt ccaaacccaa ctccaaagtt cagacaaata ggcaagtcat agttgacagc    1200
gataatagat caggttattc tggcgttttc tctgttgaag gcaaaagctg catcaatagg    1260
tgcttttatg tagagctaat aagaggaagg agacaggaag ctagagtatg gtggacttcg    1320
aacagtattg ttgtgttttg tggtacttcg ggtacatatg gttcaggctc atggcctgat    1380
ggggctgaca tcaatcttat gcctatataa                                    1410

<210> SEQ ID NO 22
<211> LENGTH: 469
<212> TYPE: PRT
<213> ORGANISM: swine influenza virus

<400> SEQUENCE: 22

Met Asn Pro Asn Gln Lys Ile Ile Thr Ile Gly Ser Val Ser Leu Ile
1               5                  10                  15

Ile Ala Thr Met Cys Phe Phe Met Gln Val Ala Ile Leu Val Thr Thr
```

```
                    20                  25                  30
Val Thr Leu His Phe Arg Gln Cys Glu Cys Asn Ser Ser Ala Thr Asn
                35                  40                  45

Gln Ile Met Pro Cys Lys Pro Thr Lys Ile Glu Arg Asn Ile Thr Glu
            50                  55                  60

Ile Val Tyr Leu Thr Asn Thr Thr Ile Lys Thr Glu Val Cys Pro Lys
65                  70                  75                  80

Leu Val Lys Tyr Arg Asp Trp Ala Lys Pro Gln Cys Arg Ile Thr Gly
                85                  90                  95

Phe Ala Pro Phe Ser Lys Asp Asn Ser Ile Arg Leu Ser Ala Gly Gly
                100                 105                 110

Ala Ile Trp Val Thr Arg Glu Pro Tyr Val Ser Cys Asp Leu Ser Lys
            115                 120                 125

Cys Tyr Gln Phe Ala Leu Gly Gln Gly Thr Thr Leu Asp Asn Arg His
            130                 135                 140

Ser Asn Asp Thr Ile His Asp Arg Thr Pro Tyr Arg Thr Leu Leu Met
145                 150                 155                 160

Asn Glu Leu Gly Val Pro Phe His Leu Gly Thr Arg Gln Val Cys Ile
                165                 170                 175

Ala Trp Ser Ser Ser Ser Cys His Asp Gly Lys Ala Trp Leu His Val
            180                 185                 190

Cys Val Thr Gly Tyr Asp Lys Asn Ala Thr Ala Ser Leu Ile Tyr Asp
            195                 200                 205

Gly Arg Leu Val Asp Ser Ile Gly Ser Trp Ser Gln Asn Ile Leu Arg
            210                 215                 220

Thr Gln Glu Ser Glu Cys Val Cys Ile Asn Gly Thr Cys Thr Val Val
225                 230                 235                 240

Met Thr Asp Gly Ser Ala Ser Gly Lys Ala Asp Thr Arg Ile Leu Phe
                245                 250                 255

Ile Glu Glu Gly Lys Ile Ile His Ile Ser Pro Leu Thr Gly Ser Ala
                260                 265                 270

Gln His Val Glu Glu Cys Ser Cys Tyr Pro Arg Tyr Pro Gly Val Arg
            275                 280                 285

Cys Val Cys Arg Asp Asn Trp Lys Gly Ser Asn Arg Pro Val Val Asp
            290                 295                 300

Ile Asn Val Lys Asp Tyr Lys Ile Asn Ser Ser Tyr Val Cys Ser Gly
305                 310                 315                 320

Leu Val Gly Asp Thr Pro Arg Asn Asn Asp Arg Ser Ser Asn Ser Asn
                325                 330                 335

Cys Gln Asn Pro Asn Asn Gln Arg Gly Asn His Gly Val Lys Gly Trp
            340                 345                 350

Ala Phe Asp Asp Gly Asn Asp Ile Trp Met Gly Arg Thr Ile Ser Asn
            355                 360                 365

Asp Ser Arg Leu Gly Tyr Glu Thr Phe Lys Val Ile Gly Gly Trp Ser
            370                 375                 380

Lys Pro Asn Ser Lys Val Gln Thr Asn Arg Gln Val Ile Val Asp Ser
385                 390                 395                 400

Asp Asn Arg Ser Gly Tyr Ser Gly Val Phe Ser Val Glu Gly Lys Ser
                405                 410                 415

Cys Ile Asn Arg Cys Phe Tyr Val Glu Leu Ile Arg Gly Arg Arg Gln
            420                 425                 430

Glu Ala Arg Val Trp Trp Thr Ser Asn Ser Ile Val Val Phe Cys Gly
            435                 440                 445
```

Thr Ser Gly Thr Tyr Gly Ser Gly Ser Trp Pro Asp Gly Ala Asp Ile
    450                 455                 460

Asn Leu Met Pro Ile
465

<210> SEQ ID NO 23
<211> LENGTH: 1410
<212> TYPE: DNA
<213> ORGANISM: Artificial Sequence
<220> FEATURE:
<223> OTHER INFORMATION: Codon optimized swine influenza virus sequence

<400> SEQUENCE: 23

```
atgaaccctaaccagaagatta ttaccatcggatccgtgtgcatgaccatcggaatggcc      60
aacctgatcctgcaaatcggaaacatcatctccatctggattagccatagcattcagctt     120
ggaaaccagagccagatcgagacttgtaaccagtccgtgatcacctacgaacaacacc       180
tgggtcaaccagacttacgtcaatatcagcaacaccaactcgctgcgggcagtccgtg       240
gtgtccgcaaagctggccggcaacagctccctgtgccccgtgtccggatgggcgatctac     300
tccaaggatacagcgtgcgcatcgggtccaaaggggacgtgttcgtcatccgcgaacca     360
ttcatttcttgctccccttggaatgtcggaccttcttcctgacccaagggggcgttgctc     420
aacgacaagcacagcaacggaaccatcaaagatcggtcgccctaccgcactctgatgtcg    480
tgccctatcggcgaagtgccatccccctacaactcacgcttcgagtccgtggcctggtcc    540
gcttccgcctgccacgatggaatcaactggctcacaatcgcatctccggcccggactcg    600
ggagccgtggccgtgctgaagtacaatggtattattactgacactatcaagtcgtggaag   660
aacaatattctccggactcagaatctgaatgcgcctgcgtgaacggttcctgcttcact    720
atcatgaccgacggcccttccgatggacaggcctcatacagatcttccgatcgagaag     780
ggaaagatcgtgaagtccgtcgagatgaacgcaccgaactaccattatgaggaatgctcg    840
tgctacccggactcctcggaaattacttgcgtgtgccgcgcaattggcacgggtccaac    900
aggccctgggtgtccttcaaccaaaacctgagtaccagatcggttacatctgctccggg    960
atttttggagacaaccctagacctaacgacaagaccggctcatgcggacctgtgtcctcc  1020
aacggagccaacggcgtgaagggattctcgttcaaatatgggaacggcgtctggataggt  1080
cggaccaagtccatctcgtcacggaaggggctttgaaatgatttgggacccgaacggttgg  1140
accggaaccgcacaagaacttcagcatcaagcaggacattacggcattaacgagtggagc  1200
ggatactcggcagcttcgtccagcacccgaacttacgggcctcaattgtattaggccc    1260
tgtttttgggtcgagctgatagagggcgccccaaggaaaacaccatctgaccagcggc    1320
tccagcatctcattctgcggagtgaactccgacaccgtgggctggtcgtggcccgacggt   1380
gccgagctgccgttcaccatcgataaatga                                 1410
```

<210> SEQ ID NO 24
<211> LENGTH: 1410
<212> TYPE: DNA
<213> ORGANISM: Artificial Sequence
<220> FEATURE:
<223> OTHER INFORMATION: Codon optimized swine influenza virus sequence

<400> SEQUENCE: 24

```
atgaatcctaaccaaaagatcatcaccatcggctccgtcagcctcactataccaccatg     60
tgcctgttccttcaaattgccatcctcgtgaccacgatcacctgcacttcaagcagtac   120
```

| | |
|---|---|
| gagtgcgact ccccggccaa caaccaggtc atcccgtgtg aaccgattat cattgagaag | 180 |
| aacatcacaa agattgtgta cctgactaac accaccatcg agaaggaagt ctgcccaaaa | 240 |
| ttgggagagt accggaactg gtccaagcct caatgcaaaa tcactggatt tgctccgttc | 300 |
| agcaaggata actcaatcag actgagcgcg ggtggcgcca tctgggtcac cagggaacct | 360 |
| tatgtgtcgt gcgatcccaa caagtgctac cagtttgcgc tgggccaggg caccacccctc | 420 |
| gacaaccgcc actccaacga caccatccat gatcgcaccc ctttccgaac cctgctgatg | 480 |
| agcgagcttg gcgtgcccctt ccacctcgga acgcgccaag tctgtattgc ctggagctcg | 540 |
| tcctcctgcc acgatggaaa ggcctggctg catgtctgtg tgactggtca cgacaagaac | 600 |
| gccaccgcta gcttcatcta tgacggaaaa ttggtggatt ccatctcctc ctggtctaag | 660 |
| aacattctgc ggacccagga atccgaatgc gtgtgcatcg atggcatctg cactgtggtc | 720 |
| atgactgacg gatccgcaag cggaaaggcg gacactaaga tcctgtttat cgaaaaggga | 780 |
| aagatcattc atatctcgcc gctgctgggg tccgcccagc acgtggaaga gtgcagctgt | 840 |
| taccccccggt accccgacgt gcggtgcatt tgtcgggaca ctggaagggg tagcaacagg | 900 |
| cccatcgtgg acattcgcat gaagaattac tcaatcggat cctcctacat gtgctcaggg | 960 |
| ctcgtgggag acacccccag gaacaacgac ggttcctcaa actccaactg tcggaacccg | 1020 |
| aacaatgagc gcgggaatca cggagtgaag ggatgggcat cgacgacgg aaacgacacc | 1080 |
| tggatgggtc ggactatcag caaggactcc cgcctgggtt acgaaacttt caaggtcgtg | 1140 |
| gggggctggt cgcagccaaa ctcgaagtcg cagattaaca gacaggtcat cgtggactcc | 1200 |
| gacaataggt ccggctactc cggaatcttc tcggtcgagg ggaaggattg cattaaccgg | 1260 |
| tgcttctacg tggagctgat cagaggcaga cgccaggaaa cccgcgtgtg gtggaccctcc | 1320 |
| aactcaatcg tggtgttctg cggaacatcc ggcacttacg gcagcggatc ctggcctgat | 1380 |
| ggcgccaaca taaacttcat gcccgtgtga | 1410 |

<210> SEQ ID NO 25
<211> LENGTH: 1410
<212> TYPE: DNA
<213> ORGANISM: Artificial Sequence
<220> FEATURE:
<223> OTHER INFORMATION: Codon optimized swine influenza virus sequence

<400> SEQUENCE: 25

| | |
|---|---|
| atgaaccccca accaaaagat cattacaatc ggatcagtgt cacttgtgat cgccaccttg | 60 |
| tgtttcctca tgcaaatggc cattctgatc accactgtga agctgcactt caaacagtat | 120 |
| gagtgcggat cccggcgaa caatcaggtc atcacctgtg aacctaccgt gatcgagcgg | 180 |
| aacaccaccg agatagtgta cctgaccaat acgactatcg aaaaggaaac ttgccataag | 240 |
| accgtcgagt accgaaactg gtcgaagccg cagtgcaaga tcactggggtt cgcaccgttc | 300 |
| agcaaggata acagcatccg gctgtccgcc gggggagaca tttgggtcac ccgcgaaccg | 360 |
| tacgtgtcgt gcgagcccgg aaagtgctac cagttcgccc tgggccaggg taccacccctg | 420 |
| gataacaagc acagcaacga taccatccac gataggaccc cctaccggac tctgctgatg | 480 |
| aacgaactgg gcgtgccttt tcacctcggc acgagacaag tctgcattgc ctggtcctca | 540 |
| tcgtcctgct acgacggaaa ggcctggctg cacgtctgca tcaccggcca tgacaaaaac | 600 |
| gccaccgcgt ccttcatcta cgacggtcgc ctggtggact ccattggatc ctggagcaag | 660 |
| aacattctgc ggacccagga atcggaatgc gtgtgtatca acggagtgtg caccgtcgtg | 720 |
| atgactgatg gctctgcttc cggccgggcc gacaccaaga tcttgtttat cgaagaaggg | 780 |

```
aagattgtcc acatttcccc gcttgctgga tccgcgcagc acgtggaaga gtgcagctgt     840
tacccccgct accctggcgt gcggtgcatt tgtcgggaca actggaaggg atccaatagg     900
cccgtggtgg acatcaacat cgaagattac tcgattgact ccagctacgt gtgctccggc     960
ctcgtcgggg acactccccg catcaacgac gggtcgagct cctcctattg ccgggatcca    1020
aacaacgaga aggggaacca cggcgtgaag ggctgggctt cgacgacgg aaacgacgtc    1080 tggatgggta gaactatcaa cgaggattcc cggagcggat acgagacttt caaggtcatc    1140
ggtggttggt caacccctaa tagcaaactc cagattaaca gacaggtcat cgtggactcg    1200
aacaatcgga gcggctactc cggagtgttc tccgtggaag aaagtcgtg catcaaccgg     1260 tgcttctacg tggagctgat taggggtcgc cgcagcgaag cccgcgtgtg gtggacttcc    1320
aactcaatcg tggtgttctg cggcacctcc gggacttacg gaaccggatc ctggccggat    1380
ggcgccgaca ttaacctgat gccaatttga                                      1410
```

<210> SEQ ID NO 26
<211> LENGTH: 1410
<212> TYPE: DNA
<213> ORGANISM: Artificial Sequence
<220> FEATURE:
<223> OTHER INFORMATION: Codon optimized swine influenza virus sequence

<400> SEQUENCE: 26

```
atgaacccca accaaaagat cattacaatc ggatcagtgt cacttgtgat cgccaccttg      60
tgtttcctca tgcaaatggc cattctgatc accactgtga agctgcactt caaacagtat     120
gagtgcggat tcccggcgaa caatcaggtc atcacctgtg aacctaccgt gatcgagcgg     180
aacaccaccg agatagtgta cctgaccaat cgactatcg aaaaggaaac ttgccataag     240
accgtcgagt accgaaactg gtcgaagccg cagtgcaaga tcactgggtt cgcaccgttc     300
agcaaggata acagcatccg gctgtccgcc ggggagaca tttgggtcac ccgcgaaccg     360
tacgtgtcgt gcgagcccgg aaagtgctac cagttcgccc tgggccaggg taccacctg     420 gataacaagc acagcaacga taccatccac gataggaccc cctaccggac tctgctgatg     480
aacgaactgg gcgtgccttt tcacctcggc acgagacaag tctgcattgc ctggtcctca    540
tcgtcctgct acgacggaaa ggcctggctg cacgtctgca tcaccggcca tgacaaaaac    600
gccaccgcgt ccttcatcta cgacggtcgc ctggtggact ccattggatc ctggagcaag    660
aacattctgc ggacccagga tcggaatgc gtgtgtatca acggagtgtg caccgtcgtg    720
atgactgatg gctctgcttc cggccgggcc gacaccaaga tcttgtttat cgaagaaggg    780
aagattgtcc acatttcccc gcttgctgga tccgcgcagc acgtggaaga gtgcagctgt     840
tacccccgct accctggcgt gcggtgcatt tgtcgggaca actggaaggg atccaatagg     900
cccgtggtgg acatcaacat cgaagattac tcgattgact ccagctacgt gtgctccggc     960
ctcgtcgggg acactccccg catcaacgac gggtcgagct cctcctattg ccgggatcca    1020
aacaacgaga aggggaacca cggcgtgaag ggctgggctt cgacgacgg aaacgacgtc    1080 tggatgggta gaactatcaa cgaggattcc cggagcggat acgagacttt caaggtcatc    1140
ggtggttggt caacccctaa tagcaaactc cagattaaca gacaggtcat cgtggactcg    1200
aacaatcgga gcggctactc cggagtgttc tccgtggaag aaagtcgtg catcaaccgg    1260 tgcttctacg tggagctgat taggggtcgc cgcagcgaag cccgcgtgtg gtggacttcc    1320
aactcaatcg tggtgttctg cggcacctcc gggacttacg gaaccggatc ctggccggat    1380
```

```
ggcgccgaca ttaacctgat gccaatttga                               1410
```

<210> SEQ ID NO 27
<211> LENGTH: 1410
<212> TYPE: DNA
<213> ORGANISM: Artificial Sequence
<220> FEATURE:
<223> OTHER INFORMATION: Codon optimized swine influenza virus sequence

<400> SEQUENCE: 27

```
atgaacccca accagaagat tatcaccatc ggatccgtgt ctctcatcat cgccaccatg   60
tgcttcttta tgcaagtggc cattctcgtc accactgtga ccctgcactt tcggcagtgc  120
gaatgcaact cctccgctac taaccaaatt atgccgtgca agcctactaa gatcgaacgg  180
aacatcaccg agatcgtgta cttgacgaac accaccatca agaccgaagt ctgcccgaag  240
cttgtgaaat atcgggactg ggcgaagcca caatgtcgca tcaccggttt cgccccgttc  300
agcaaagata cagcattcg gctgtccgcc gggggcgcga tctgggtcac cagggagccg  360
tacgtgtcgt gtgatctgtc caagtgctac caattcgcac tgggacaggg taccaccctc  420
gacaaccgcc actccaacga taccatacat gaccggaccc cttaccgcac tctcttgatg  480
aacgagctgg gagtgcccct tccacctggg accagacaag tctgcattgc ctggtcctca  540
tcctcctgcc atgacgggaa ggcctggctg catgtctgcg tgactggcta cgataagaac  600
gcgacggcct ccctgatcta cgacggtcgc ctggtggact ccattgggtc gtggagccag  660
aatatcctgc ggactcagga gtcagaatgc gtgtgcatca acggcacttg caccgtggtc  720
atgactgacg gatccgcctc ggggaaggcc gacaccagga tcctgttcat tgaggaggga  780
aagattatcc acatctcgcc tctgactgga tccgcccagc acgtggaaga gtgttcctgc  840
taccctcgat accccggcgt gcgctgtgtg tgtcgggata actggaaggg aagcaaccgg  900
cccgtggtgg acattaacgt gaaggactac aagattaact catcatacgt gtgctccgga  960
ctcgtgggcg atacaccaag aaacaacgac cgcagcagca cagcaattg tcagaaccc  1020
aacaaccagc gcggcaacca cggcgtgaag ggctgggcat tcgacgacgg aaatgacatc 1080
tggatgggga ggactatctc caacgattca cgcctgggct acgaaaacctt caaggtcatc 1140
ggcggctggt caaaaccgaa ctccaaggtc cagaccaaca gacaggtcat cgtggattcg 1200
gacaatagaa gcggatacag cggagtgttc agcgtggagg gaaagtcgtg catcaaccgc 1260
tgcttctacg tggaactgat caggggtcgg agacaggaag cgcgcgtgtg gtggacttcg 1320
aactcgattg tggtgttctg cggtacctcc ggaacctatg ggagcggatc ctggccggac 1380
ggcgctgaca ttaaccttat gccgatctga                                  1410
```